United States Patent
Kushalappa et al.

(10) Patent No.: US 8,946,514 B2
(45) Date of Patent: Feb. 3, 2015

(54) SORGHUM FERTILITY RESTORER GENOTYPES AND METHODS OF MARKER-ASSISTED SELECTION

(75) Inventors: Kumuda Kushalappa, Mississauga (CA); Valerio Primomo, Toronto (CA); Lomas Tulsieram, Mississauga (CA); Zenglu Li, Ankeny, IA (US); Kay Porter, Plainview, TX (US); Yilma Kebede, Renton, WA (US); Roger Monk, Portland, TX (US); Rex DeLong, Canyon, TX (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 1043 days.

(21) Appl. No.: 12/978,576

(22) Filed: Dec. 26, 2010

(65) Prior Publication Data

US 2011/0162100 A1    Jun. 30, 2011

Related U.S. Application Data

(60) Provisional application No. 61/290,283, filed on Dec. 28, 2009.

(51) Int. Cl.
| | |
|---|---|
| *A01H 1/02* | (2006.01) |
| *A01H 5/12* | (2006.01) |
| *C12Q 1/68* | (2006.01) |
| *A01H 1/04* | (2006.01) |
| *C07K 14/415* | (2006.01) |
| *C12N 15/82* | (2006.01) |

(52) U.S. Cl.
CPC ............. *C12Q 1/6895* (2013.01); *A01H 1/02* (2013.01); *A01H 1/04* (2013.01); *C07K 14/415* (2013.01); *C12N 15/8287* (2013.01); *C12N 15/8289* (2013.01)
USPC ........... 800/303; 800/274; 800/266; 800/267; 800/320

(58) Field of Classification Search
None
See application file for complete search history.

(56) References Cited

PUBLICATIONS

Cregan et al. (Theor. Appl. Genet. (1999) 99: pp. 811-818).*
International Search Report (PCT/US2010/062112) dated Dec. 26, 2010.
Database accession No. AL844530, XP002627239, Jul. 22, 2002.
Bedll J. A., et al., Sorghum Genome Sequencing by Methylation Filtration PLOS Biology, Public Library of Science, US, vol. 3, No. 1, Jan. 1, 2005.
Klein, et al., Fertility restorer locus Rf1 of sorghum (*Sorghum bicolor* L.) encodes a pentatricopeptide . . . , Theor Appl Cenet, vol. 111, No. 6, Oct. 1, 2005.
Akagi, H., et al., "Positional cloning of the rice Rf-1 gene, a restorer of BT-type cytoplasmic male sterility . . . ", Theor. Appl. Genet., vol. 108, pp. 1449-1457 (2004).
Bentotila, et al., "A pentatricopeptide repeat-containing gene restores fertility to cytoplasmic male-sterile plants", PNAS, vol. 99, pp. 10887-1089 (2002).
Bhattramakki, D., et al., "An integrated SSR and RFLP linkage map of *Sorghum bicolor* (L.) Moench", Genome, vol. 43, pp. 988-1002 (2000).
Brown, G., et al., "The radish Rfo restorer gene of Ogura cytoplasmic male sterility encodes a protein with multiple pentatrico . . . ", Plant J., vol. 35, pp. 262-272 (2003).
Klein, R.R., et al., "Molecular Mapping of the rf1 Gene for Pollen Fertility Restoration in Sorghum (*Sorghum bicolor* L.)", Theor. Appl. Genet., vol. 102, pp. 1206-1212 (2001).
Kong, et al., "Characteristics, linkage-map positions, and allelic differentiation of *Sorghum bicolor* (L.) Moench . . . ", Theor. App. Genet., vol. 101, pp. 438-448 (2000).
Menz, M.A., et al., "A high-density genetic map of *Sorghum bicolor* (L.) Moench based on 2926 AFLP, RFLP and SSR markers", Plant Molec. Biol., vol. 48, pp. 483-499 (2002).
Paterson, et al., "The *Sorghum bicolor* genome and the diversification of grasses", Nature, vol. 457, pp. 551-556 (2009).
Tang, H.V., et al., "Transcript processing internal to a mitochondrial open reading frame is correlated with fertility restoration . . . ", Plant J., vol. 10, pp. 123-133 (1996).
Tang, H.V., et al., "Cosegregation of Single Genes Associated with Fertility Restoration and Transcript Processing of Sorghum . . . ", Genetics, vol. 150, pp. 383-391 (1998).
Waxman, S., et al., "History of the development of arsenic derivatives in cancer therapy", The Oncologist, vol. 6 (suppl 2), pp. 3-10 (2001).
Wen, L., et al., "Development and mapping of AFLP markers linked to the sorghum fertility restorer gene rf4", Theor. Appl. Genet., vol. 104, pp. 577-585 (2002).

* cited by examiner

*Primary Examiner* — Brent T Page
*Assistant Examiner* — Jared Shapiro

(57) ABSTRACT

Markers tightly associated with a *sorghum* (*Sorghum bicolor*) cms fertility restorer gene are identified, as well as genes containing the pentatrico peptide repeat (PPR) motif. Methods for marker assisted selection of restorer and non-restorer *sorghum* lines are provided. The markers can be used to facilitate development of the maintainer, restorer and cms *sorghum* lines used to make hybrids.

2 Claims, 19 Drawing Sheets

Alignment of PPR 1, 3, 4 and 5 genes

```
                    1                                                50
sPPR1         (1)   ATGTCGACCCGGGCGCGGCCCGCTTGGTTGAACAAGCTAAAGCGGATCAT
sPPR4         (1)   --------------------------------------------------
SPPR3         (1)   ---------ATGTCGAGCCGGACGTGCCTGAAGAAGCTGAAGCGGATCAT
sPPR5         (1)   --------------------------------------------------

51                                               100
sPPR1         (51)  TGGACGGCGCATCCGCTCGGGAAGCCTCAGTGCTGAGGCCGCGCGCCAAC
sPPR4         (1)   --------------------------------------------------
SPPR3         (42)  TGGACGGCGCATCCGCTCGGGAAGCCTCAGCGCTGAGGCCGCGCGCCAAC
sPPR5         (1)   --------------------------------------------------

101                                              150
sPPR1         (101) TCTGCGACGAGGTGCTCCCATCGATCCAAAGTCGTTCCCCACCACCGGCC
sPPR4         (1)   --------------------------------------------------
SPPR3         (92)  TCTGGAACGAGGTGCTCCCATCGATCCAATATCGTTCCCCACCACCGGCC
sPPR5         (1)   ---------ATGTTCTAC-A-----CCAGAACTCTTCAAGGCAGCCGGCC 151                                              200
sPPR1         (151) GCTTCAGCAGCCGCGCGCCGGTGGAGGGCCGACCGCCGCCCTTCCTGGGA
sPPR4         (1)   --------------------------------------------------
SPPR3         (142) GCTTCAGCAGCCGCGCGCCGGTGGAGAGCCGACCGCCGCCGTTCCTGGGA
sPPR5         (36)  GGTTCGGCAGCGGGGTC-----GGAGGTACGAAAACCGCCCGTCCTGCGA 201                                              250
sPPR1         (201) GCTGGAGCAGTTCATCGGACAGTGTTACCGCTCGGGTGACCTCGCCCCCG
sPPR4         (1)   --------------------------------------------------
SPPR3         (192) GCTGGAGCAGTTCATCGGAGAGTGTTACCGCTCGGGGGACCTCGGCCCCG
sPPR5         (81)  GCTGGAGCGCTTCATCGGAGAGTGTTTCCGCTCGGGAGACCTTGACCCCG 251                                              300
sPPR1         (251) AGGACGCAGTCGATCTGTTCGACGAATTGCTTCACCAAGCGAGGCCCGGC
sPPR4         (1)   --------------------------------------------------
SPPR3         (242) AGGACGCACTCGATCTGTTCGACGAATTGCTTCAGCGAGCGAGGCCCGGC
sPPR5         (131) AGGACGCACTCGATCTGTTCGACGAGCTGCTTCCCCAAGCGAGGCAAGGC 301                                              350
sPPR1         (301) TCCATTTACGCCCTCAACCAGCTGCTCACCACGGTCGCTCGCGCCCCGGT
sPPR4         (1)   --------------------------------------------------
SPPR3         (292) TCCATTTACGCCCTCAACCAGCTGCTCACCACGGTCGCTCGCGCCCCCGT
sPPR5         (181) TCCGTTTATGCCCTCACCCGGCTCCTCACCACTGTCGCTCGCGCCCCAGT 351                                              400
sPPR1         (351) CTCCTCCACTGTGCGCGATGGCCCTGCTCGCGCCGTGTCCATGTTCAACC
sPPR4         (1)   --------------------------------------------------
SPPR3         (342) CTCCTCCTTCTGTGCGCGATGGCCCTGCGCTCGCCGTGTCCATGTTCAACC
sPPR5         (231) CTCCTCCGCCGTGCCCAACGGCCCTGCCCTCCGTGTCCATGTTCAACC 401                                              450
sPPR1         (401) GTATGGCCCGAGCGGGCGCCAAGAAGGTGGCTCCAGACATAGCTACCTTC
sPPR4         (1)   --ATGGCCCGAGCGGGCGCCAAGAAGGTGGCTCCAGACATAGCTACCTTC
SPPR3         (392) GTATGGCCCGAGCGGGCGCCAAGAAGGTGGCTCCAGACATAGCTACCTTC
sPPR5         (281) GCATGGCCCGAGCGGGCTCCAAGAAGGTTGCTCCGACCACAGTTACCTAC
```

Figure 4A

```
                    451                                               500
sPPR1     (451)  GGCATCCTCATCAGCTGCTGTTGCAACGCGGGCTGTTTGAACCTCGGCTT
sPPR4      (49)  GGCATCCTCATCAGCTGCTGTTGCGACGCGGGCTGTTTGAACCTCGGCTT
SPPR3     (442)  GGCATCCTCATCAGCTGCTGTTGCGACGCGGGCTGTTTGAACCTCGGCTT
sPPR5     (331)  ACCATCCTCATCAGCTGCTGCTGCTATGTAGGCTGCTTGAACCTCGCCTT 501                                               550
sPPR1     (501)  CGCTGCATTGGGCCAAATCATTAAGACGGGAGTGAGGGCACATGCCGTCA
sPPR4      (99)  CGCTGCATTGGGGCAAATAATTAAGACGGGACTGAGGGCAGATGCCGTCG
SPPR3     (492)  CGCTGCATTGGGGCAAATCATTAAGACGGGACTGAGGGCACAGGCCGTCA
sPPR5     (381)  TGCCGCATTGGGCCAAATCATTAAGACGGGACTGAGGGCAAATGCCATCA 551                                               600
sPPR1     (551)  CCTTCACGCCCCTGCTCAGGACCCTCTGCGCCGAGAAGAGGACAAGCGAT
sPPR4     (149)  CCTTCACGCCCCTGCTCAGGACCCTCTGCGCCAAGAAAAGGACGAGTGAC
SPPR3     (542)  CCTTCACGCCCCTGCTCAGGACCCTCTGCGCCGAGAAGAGGACGAGTGAC
sPPR5     (431)  GTTTCACGCCTATACTTACGACCCTCTGTGCTGAGAAGAGGACGAGTGAT 601                                               650
sPPR1     (601)  GCAATGAATATTGTGCTCAGGCGGATGCCTGAGCTCGGCTGCACCCCCGA
sPPR4     (199)  GCAATGAATATTGTGCTCAGGCGGATGCCTGAACTTGGCTGCACCCCCGA
SPPR3     (592)  GCAATGAATATTGTGCTCAGGCGGATGCCTGAGCTCGGCTGCACCCCCGA
sPPR5     (481)  GCAATGAATATTGTGATCAGATGGACGCCTAAGCTTGGCTGCACCCCGGA 651                                               700
sPPR1     (651)  TGTCTTCTCCTACACCACACTTCTCAAAGGGCTTTGTGCTGAGAAGAAAT
sPPR4     (249)  TGTCTTCTCCTACAGCACACTTCTCAAAGGGCTTTGTGCTGAGAAGAAAT
SPPR3     (642)  TGTCTTCTCCTACACCACACTTCTCAAAGGGCTTTGTGCTGAGAAGAAAT
sPPR5     (531)  TGTCTTCTCCTACACCGTACTTCTCAAAGGGCTATGTGACGAGAAGAAAT 701                                               750
sPPR1     (701)  GTGAAGAGGCTGCCGAGCTGATCCACATGATGGCTGAAGATGGAGACAAC
sPPR4     (299)  GTGAAGAGGCTGCCGAGCTGATCCACATGATGGCTGAAGATGGAGACAAC
SPPR3     (692)  GTGAAGAGGCTGCCGAGCTGATCCACATGATGGCTGAAGATGGAGACAAC
sPPR5     (581)  GTGAAGAGGCTGTTGACCTGATCCACATGATGGCTGAGGATGGAGATCAC 751                                               800
sPPR1     (751)  TGCCCACCTAATGTGGTGTCCTATAGCACTGTAATCCATGGATTCTTTAA
sPPR4     (349)  TGCCCACCTGATGTGGTGTCTTATAGCACTGTAATCCATGGGTTCTTTAA
SPPR3     (742)  TGCCCACCTAATGTGGTGTCTTATACCACTGTAATCCATGGATTCTTTAA
sPPR5     (631)  TGCCCACCTAATGTGGTGTCTTATACCACCGTAATCCATGGCTTCTTTAA 801                                               850
sPPR1     (801)  AGAGGGAGAGGTAGGGAAAGCTTACACCCTGTTTTGCAAAATGCTTGATC
sPPR4     (399)  AGAGGGAGATGTAGGGAAAGCTTACACCCTGTTTTGCAAAATGCTTGATC
SPPR3     (792)  AGAGGGAGATGTAGGGAAAGCTTACACCCTGTTTTGCAAAATGCTTGATC
sPPR5     (681)  AGAGGATGAGGTGGGGAAAGCTTACACCCTGTTTTGTGAAATGCTTGATC 851                                               900
sPPR1     (851)  ATGGGATCCCGCCAGATGTTGTGACCTGCAATTCAGTCATTGATGGCCTA
sPPR4     (449)  ATGGGATCCCTCCAAATGTTGTGACCTGCAATTCAGTCATTGATGGCCTA
SPPR3     (842)  ATGGGATCCCGCCAAATGTTGTGACCTGCAATTCAGTCATTGATGGCCTA
sPPR5     (731)  GTGGGATCCCGCCGGATGTTGTGACTTGCAACTCAATCATTGATGGCCTA 901                                               950
sPPR1     (901)  TGCAAGGCTCAAGCAATGGACAAGGCCGAGGAGGTCCTTCAGCAGATGAT
sPPR4     (499)  TGCAAGGTTCAAGCAATGGACAAGGCCGAGGCAGTCCTTCAGCAGATGAT
SPPR3     (892)  TGCAAGGTTCAAGCAATGGACAAGGCCGAGGCAGTCCTTCAGCAGATGAT
sPPR5     (781)  TGCAAGGTTCAAGCAATGGACAAGGCTGAGGAGGTCCTTCGACAGATGTT
```

Figure 4B

```
              951                                              1000
sPPR1  (951)  TGACGAACATATTATGCCTGATTGTACTACATATAACAGTCTGATCCATG
sPPR4  (549)  TGACGAGCATATTATGCCTAATTGTACTACATATAACAGTCTGATCCATG
SPPR3  (942)  TGACGAGCATATTATGCCTAATTGTACTACATATAACAGTCTGATCCATG
sPPR5  (831)  TGACAAACATATTATGCCTGACTGCACTACATATAACAGTCTGGTCCATG 1001                                             1050
sPPR1  (1001) GATACCTCTCTCTGGGACAGTGGAAAGAGGCAGTCCAAATTCTCAAAGAA
sPPR4  (599)  GATACCTCTCTTCAGGACAGTGGACGGAGGCAGTCAGAATTCTCAAAGAA
SPPR3  (992)  GATACCTCTCTTCAGGACAGTGGACGGAGGCAGTCAGAATTCTCAAAGAA
sPPR5  (881)  GATACCTCTCTTCGGGACAACTGAAAGAGGCGGTCAGAATTCTCAAACAA 1051                                             1100
sPPR1  (1051) ATGTCTAGAGATGGGCAGGGGCCAAATGTTGTTACTTACAGTATGCTGAT
sPPR4  (649)  ATGTCTAGAGATGGGCAACGGCCAAATGTTGTTACTTACAATATGCTGAT
SPPR3  (1042) ATGTCTAGAGATGGGCAACGGCCAAATGTTGTTACTTACAGTATGCTCAT
sPPR5  (931)  ATGTCAAGACATGGGCAACCACCAAATGGTGTTACTTACAGCATGCTGAT 1101                                             1150
sPPR1  (1101) AAACTGTCTTTGTAAATCTGGATTGCGCGCAGAAGCTAGAGAGATCTTTA
sPPR4  (699)  AGACTGTCTTTGTAAATCTGGATTTCACGCAGAAGCTAGAGAGATCTTTA
SPPR3  (1092) AGACTGTCTTTGTAAATCTGGATTGCACGCAGAAGCTAGAGAGATCTTTA
sPPR5  (981)  AGACTGTCTTTGCAAATTTGGAGGGCACACAGAAGCTAGAGAAATTTTGA 1151                                             1200
sPPR1  (1151) ATTCTATGATTCAGAGTGGTCAAAAACCCAATGCCGCCACTTATCGAAGT
sPPR4  (749)  ATTCTATGATTCAGAGCGGTCCAAAGCCCGATGCCACCACTTATGGAAGT
SPPR3  (1142) ATTCTATGATTCAGAGCGGTCAAAAACCCAATGCCTCCACTTATGGCAGT
sPPR5  (1031) ATTCTATGATTCAGAGCCGTGGAAACCCCAATGTTGCCACCTACGGAGGT 1201                                             1250
sPPR1  (1201) CTGCTTCATGGGTATGCTACCGAAGGCAATCTTGTTGATATGAACAATGT
sPPR4  (799)  CTGCTTCATGGGTATGCTACCGAAGGCAATCTAGTTGAAATGAACAATGT
SPPR3  (1192) CTGCTTCATGGGTATGCTACCGAAGGCAATCTTGTTGATATGAACAATGT
sPPR5  (1081) CTGCTTCATGGGTACGCTACCAAAGGAGATCTTGTTGAAATGAATAATCT 1251                                             1300
sPPR1  (1251) CAAAGATCTAATGGTACAAAATGGAATGCGACCTGACCGTCATGTCTTCA
sPPR4  (849)  CAAAGATTTGATGGTACAGAATGGAATGCGATCTAATCATCATACCTTCA
SPPR3  (1242) CAAAGATCTAATGGTACAAAATGGAATGCGACCTGGCCGTCATGTCTTCA
sPPR5  (1131) CATAGATTTGATGGTACAGAACGGAGTGCGACCTGATCATCATATCTTCA 1301                                             1350
sPPR1  (1301) ACATAGAAATCTATGCATACTGTAAATGTGGAAGGCTAGATGAGGCAAGC
sPPR4  (899)  GCATAGAGATCTATGCATACTGTAAATGTGGAAGGTTAGATGAGGCCAGC
SPPR3  (1292) ACATAGAAATCTATGCATACTGTAAATGTGGAAGGCTAGATGAGGCAAGC
sPPR5  (1181) ACATACAGATTTATGCATACGTCAAATGTGGAAGGTTAGATGAGGCAATG 1351                                             1400
sPPR1  (1351) CTTACTTTTAACAAAATGCAGCAGCTAGGATTCATGCCAGACATAGTCAC
sPPR4  (949)  CTTACTTTTATCAAAATGCAGCAGCTTGGATTCATGCCAGACATAGTCAC
SPPR3  (1342) CTTACTTTTAACAAAATGCAGCAGCAAGGATTCATGCCAGACATAGTCGC
sPPR5  (1231) CTTACTTTTAACAAAATGCGGCAGCAAGGATTGATGCCAGACATAATCAG 1401                                             1450
sPPR1  (1401) CTACACCACGGTTATAGATGGGCTTTGCAAGATAGGCCGGCTGGACGATG
sPPR4  (999)  CTACACCACAGTTATAGATGGGCTTTGCAAGATAGGCCGGCTGGACGATG
SPPR3  (1392) CTACACCACAGTTATAGATGGGCTTTGCAAGATAGGCCGGCTGGACGATG
sPPR5  (1281) CTATGGGACGATGATAGATGGGCTTTGCAAGATAGGCCGGCTGGACGCTG
```

Figure 4C

```
                   1451                                                1500
sPPR1    (1451)    CAATGTCCCGATTCTGTCAGATGATTGATGATGGATTGTCTCCCAATATC
sPPR4    (1049)    CAATGTCCCGATTCTGTCAGATGATTGATGATGGATTGTCTCCCAATATC
SPPR3    (1442)    CAATGTCCCGATTCTGTCAGATGATTGATGATGGATTGTCTCCCGATATC
sPPR5    (1331)    CAATGTCCCAATTCTGTCAGATGATTGATGATGGATTGTCTCCAGATATT 1501                                                1550
sPPR1    (1501)    ATAACATTTACGACCCTGATTCATGGGTTTTCTATGTATGGCAAATGGGA
sPPR4    (1099)    ATAACATTTACGACCCTAATTCATGGGTTTTCTATGTATGGCAAATGGGA
SPPR3    (1492)    ATAACATTCAATACTCTAATTCATGGTTTTGCTTTGCATGGCAAATGGGA
sPPR5    (1381)    GTAGTATTTACTAATCTAATACATGGTTTTCTATGTACGGCAAATGGGA 1551                                                1600
sPPR1    (1551)    GAAGGCTGAGGAACTATTTTATGAGATGATGGATAGAGGCATTCCTCCTA
sPPR4    (1149)    AAAGGCTGAGGAACTATTTTATGAGATGATGGATAGAGGCATTCCTCCTG
SPPR3    (1542)    GAAGGCCGAGGAATTATTTTATGAGATGATGGATAGAGGCATTCCTCCTA
sPPR5    (1431)    GAAGGCTGAGGAACTATTTTATGAGATGATGGATAGAGGCATTCGTCCTA 1601                                                1650
sPPR1    (1601)    ATGTCAATACGTTCAATTCAATGATAGATAGGCTATTCAAAGAAGGAAAG
sPPR4    (1199)    ATGTCACTATCTTCACTGCAATGATAGATAGGCTATTCAAAGAAGGAAAG
SPPR3    (1592)    ATGTCAATACGTTCAATTCAATGATAGACAAGCTATTCAAAGAAGGAAAG
sPPR5    (1481)    CTGTCGTTGTCTTCACTACAATGATAGACAAGCTATTCAAAGAAGGAAAG 1651                                                1700
sPPR1    (1651)    GTTACGGAGGCCCGAAAACTCTTTGATTTGATGCCACGTGCAGGAGCTAA
sPPR4    (1249)    GTTACGGAGGCCCAAAAACTCTTTGATTTGATGCCACGTGCAGGAGCTAA
SPPR3    (1642)    GTTACAGAGGCCCGAAAACTCTTTGATTTGATGCCACGTGCAGGAGCTAA
sPPR5    (1531)    GTTACCGAGGCCAAAACACTCTTTGATTTGATGCCAATTGCTAGTGTAAA 1701                                                1750
sPPR1    (1701)    ACCTAATGTTGTTTCTTATAATACAATGATTCATGGGTATTTCATAGCTG
sPPR4    (1299)    ACCTAATGTTGTTTCTTATAATACAATGATCATGGGTATTTCATAGCTG
SPPR3    (1692)    ACCTAATGTTGTTTCTTATAATACAATGATTCATGGGTATTTCATAGCTG
sPPR5    (1581)    ACCTAATGTGGTTTCCTACAATGCAATCATTCATGGATATTTCTTGGCTG 1751                                                1800
sPPR1    (1751)    GTGAAGTGGGCGAAGTGATGAAGCTCCTTGATGATATGCTCTTGATTGGC
sPPR4    (1349)    GTGAAGTGGGCGAAGTGATGAAGCTCCTTGATGATATGCTCTTGATTGGC
SPPR3    (1742)    GTGAAGTGGGCGAAGTGATGAAGCTCCTTGATGATATGCTCTTGATTGGC
sPPR5    (1631)    GTAAACTGGATGAAGTGCTGAAGCTCCTTGATGATATGCTCTCAGTTGGC 1801                                                1850
sPPR1    (1801)    TTGAAACCCAATGCTGTTAACCTTAATACTTTACTTGATGGCATGCTCTC
sPPR4    (1399)    TTGAAACCCACTGCTGTTACCTTTAATACTTTACTTGATGGCATGGTCTC
SPPR3    (1792)    TTGAAACCCACTGCTGTTACCTTTAATACTTTACTTGATGGCATGGTCTC
sPPR5    (1681)    TTGAAACCCAATGCTGTTACTTTTAATACTTTACTTGATGACATGCTTTC 1851                                                1900
sPPR1    (1851)    TATTGGCTTGAAACCAAATGTTGACACATGTAAGACTTTGATTGATAGCT
sPPR4    (1449)    TATGGGATTGAAACCTGATGTTGACACCTGTAAGACTTTAATTGATAGCT
SPPR3    (1842)    TATGGGATTGAAACCTGATGTTGTTACCTGTAAGACTTTGATTGATAGCT
sPPR5    (1731)    TATGGGCTTGAAACCCGATGTTGCTACCTGTAACACTTTGATTGATAGCT 1901                                                1950
sPPR1    (1901)    GCTGTGAAGATGACAGGATAGAGGATATATTAACTCTGTTCCGAGAAATG
sPPR4    (1499)    GCTGTGAAGATGGCAGGATAGAGGATATATTAACTCTGTTCCGAGAAATG
SPPR3    (1892)    GCTGTGAAGATGGCAGGATAGAGGATATATTAACTCTGTTCCGAGAAATG
sPPR5    (1781)    GCTGTGAAGACGGTAGGATAGAAGATGTATTGACTCTTTTCAGAGAAATG
```

Figure 4D

```
              1951                                              2000
sPPR1  (1951) TTGAGCAAGGCTGATAAGACTGACACTATCACGGAAAATATAAAACTCAA
sPPR4  (1549) TTGGGCAAGGCTGATAAGACTGACACTATCACGGAAAATATAAAACTGTG
SPPR3  (1942) TTGGGCAAGGCTGATAAGACTGACACTATCACGGAAAATATAAAACTACG
sPPR5  (1831) TTGAGCAAGGCAGCTAAGACTGACACTGTCACGGAAAATATAATTTCCTG 2001                                              2050
sPPR1  (2001) ATGCATGAAAAAAAAAAACAAGGTATGGTTGAACAAGCTGAAGCGGATCA
sPPR4  (1599) A-------------------------------------------------
SPPR3  (1992) AGGTGT-AACCGTGAAAGCTTCTTATCACTGTTCCAGTGTGGTAATTTCG
sPPR5  (1881) A-------------------------------------------------

2051                                              2100
sPPR1  (2051) TTGGACGGCGCATCCGCTCGGGAAGCCTCAGCGCTGAGGCCGCGCGCCAA
sPPR4  (1600) --------------------------------------------------
SPPR3  (2041) CTCAAAGCTTTAGAAGTTGTTACACAAGCAGGAGCTATTTCATGCATTTG
sPPR5  (1882) --------------------------------------------------
```

Figure 4E

|            |      | 1                                                  50 |
|------------|------|-------------------------------------------------------|
| HAP1-M029  | (1)  | GAAGGCTAGATGAGGCAAGCCTTACTTTTAACAAAATGCAGCAGCTAGGA    |
| HAP1-M221  | (1)  | GAAGGCTAGATGAGGCAAGCCTTACTTTTAACAAAATGCAGCAGCTAGGA    |
| HAP1-M250  | (1)  | GAAGGCTAGATGAGGCAAGCCTTACTTTTAACAAAATGCAGCAGCTAGGA    |
| HAP1-M279  | (1)  | GAAGGCTAGATGAGGCAAGCCTTACTTTTAACAAAATGCAGCAGCTAGGA    |
| HAP1-M536  | (1)  | GAAGGCTAGATGAGGCAAGCCTTACTTTTAACAAAATGCAGCAGCTAGGA    |
| HAP1-M928  | (1)  | GAAGGCTAGATGAGGCAAGCCTTACTTTTAACAAAATGCAGCAGCTAGGA    |
| HAP1-M1400 | (1)  | GAAGGCTAGATGAGGCAAGCCTTACTTTTAACAAAATGCAGCAGCTAGGA    |
| HAP1-M1425 | (1)  | GAAGGCTAGATGAGGCAAGCCTTACTTTTAACAAAATGCAGCAGCTAGGA    |
| HAP1-M1498 | (1)  | GAAGGCTAGATGAGGCAAGCCTTACTTTTAACAAAATGCAGCAGCTAGGA    |
| HAP2-R158  | (1)  | GAAGGCTAGATGAGGCAAGCCTTACTTTTAACAAAATGCAGCAGCTAGGA    |
| HAP2-R159  | (1)  | GAAGGCTAGATGAGGCAAGCCTTACTTTTAACAAAATGCAGCAGCTAGGA    |
| HAP2-R162  | (1)  | GAAGGCTAGATGAGGCAAGCCTTACTTTTAACAAAATGCAGCAGCTAGGA    |
| HAP2-R163  | (1)  | GAAGGCTAGATGAGGCAAGCCTTACTTTTAACAAAATGCAGCAGCTAGGA    |
| HAP2-R166  | (1)  | GAAGGCTAGATGAGGCAAGCCTTACTTTTAACAAAATGCAGCAGCTAGGA    |
| HAP2-R174  | (1)  | GAAGGCTAGATGAGGCAAGCCTTACTTTTAACAAAATGCAGCAGCTAGGA    |
| HAP2-R396  | (1)  | GAAGGCTAGATGAGGCAAGCCTTACTTTTAACAAAATGCAGCAGCTAGGA    |
| HAP2-R424  | (1)  | GAAGGCTAGATGAGGCAAGCCTTACTTTTAACAAAATGCAGCAGCTAGGA    |
| HAP3-M144  | (1)  | GAAGGCTAGATGAGGCAAGCCTTACTTTTAACAAAATGCAGCAGCTAGGA    |
| HAP3-M172  | (1)  | GAAGGCTAGATGAGGCAAGCCTTACTTTTAACAAAATGCAGCAGCTAGGA    |
| HAP3-M187  | (1)  | GAAGGCTAGATGAGGCAAGCCTTACTTTTAACAAAATGCAGCAGCTAGGA    |
| HAP3-M331  | (1)  | GAAGGCTAGATGAGGCAAGCCTTACTTTTAACAAAATGCAGCAGCTAGGA    |
| HAP3-M682  | (1)  | GAAGGCTAGATGAGGCAAGCCTTACTTTTAACAAAATGCAGCAGCTAGGA    |
| HAP3-M687  | (1)  | GAAGGCTAGATGAGGCAAGCCTTACTTTTAACAAAATGCAGCAGCTAGGA    |
| HAP3-R633  | (1)  | GAAGGCTAGATGAGGCAAGCCTTACTTTTAACAAAATGCAGCAGCTAGGA    |
| HAP3-M1423 | (1)  | GAAGGCTAGATGAGGCAAGCCTTACTTTTAACAAAATGCAGCAGCTAGGA    |
| HAP4-M048  | (1)  | GAAGGCTAGATGAGGCAAGCCTTACTTTTAACAAAATGCAGCAGCTAGGA    |
| HAP4-R179  | (1)  | GAAGGCTAGATGAGGCAAGCCTTACTTTTAACAAAATGCAGCAGCTAGGA    |

|            |      | 51                                                 100 |
|------------|------|-------------------------------------------------------|
| HAP1-M029  | (51) | TTCATGCCAGACATAGTCACCTACACCACGGTTATAGATGGGCTTTGCAA    |
| HAP1-M221  | (51) | TTCATGCCAGACATAGTCACCTACACCACGGTTATAGATGGGCTTTGCAA    |
| HAP1-M250  | (51) | TTCATGCCAGACATAGTCACCTACACCACGGTTATAGATGGGCTTTGCAA    |
| HAP1-M279  | (51) | TTCATGCCAGACATAGTCACCTACACCACGGTTATAGATGGGCTTTGCAA    |
| HAP1-M536  | (51) | TTCATGCCAGACATAGTCACCTACACCACGGTTATAGATGGGCTTTGCAA    |
| HAP1-M928  | (51) | TTCATGCCAGACATAGTCACCTACACCACGGTTATAGATGGGCTTTGCAA    |
| HAP1-M1400 | (51) | TTCATGCCAGACATAGTCACCTACACCACGGTTATAGATGGGCTTTGCAA    |
| HAP1-M1425 | (51) | TTCATGCCAGACATAGTCACCTACACCACGGTTATAGATGGGCTTTGCAA    |
| HAP1-M1498 | (51) | TTCATGCCAGACATAGTCACCTACACCACGGTTATAGATGGGCTTTGCAA    |
| HAP2-R158  | (51) | TTCATGCCAGACATAGTCACCTACACCACGGTTATAGATGGGCTTTGCAA    |
| HAP2-R159  | (51) | TTCATGCCAGACATAGTCACCTACACCACGGTTATAGATGGGCTTTGCAA    |
| HAP2-R162  | (51) | TTCATGCCAGACATAGTCACCTACACCACGGTTATAGATGGGCTTTGCAA    |
| HAP2-R163  | (51) | TTCATGCCAGACATAGTCACCTACACCACGGTTATAGATGGGCTTTGCAA    |
| HAP2-R166  | (51) | TTCATGCCAGACATAGTCACCTACACCACGGTTATAGATGGGCTTTGCAA    |
| HAP2-R174  | (51) | TTCATGCCAGACATAGTCACCTACACCACGGTTATAGATGGGCTTTGCAA    |
| HAP2-R396  | (51) | TTCATGCCAGACATAGTCACCTACACCACGGTTATAGATGGGCTTTGCAA    |
| HAP2-R424  | (51) | TTCATGCCAGACATAGTCACCTACACCACGGTTATAGATGGGCTTTGCAA    |
| HAP3-M144  | (51) | TTCATGCCAGACATAGTCACCTACACCACGGTTATAGATGGGCTTTGCAA    |
| HAP3-M172  | (51) | TTCATGCCAGACATAGTCACCTACACCACGGTTATAGATGGGCTTTGCAA    |
| HAP3-M187  | (51) | TTCATGCCAGACATAGTCACCTACACCACGGTTATAGATGGGCTTTGCAA    |
| HAP3-M331  | (51) | TTCATGCCAGACATAGTCACCTACACCACGGTTATAGATGGGCTTTGCAA    |
| HAP3-M682  | (51) | TTCATGCCAGACATAGTCACCTACACCACGGTTATAGATGGGCTTTGCAA    |
| HAP3-M687  | (51) | TTCATGCCAGACATAGTCACCTACACCACGGTTATAGATGGGCTTTGCAA    |
| HAP3-R633  | (51) | TTCATGCCAGACATAGTCACCTACACCACGGTTATAGATGGGCTTTGCAA    |
| HAP3-M1423 | (51) | TTCATGCCAGACATAGTCACCTACACCACGGTTATAGATGGGCTTTGCAA    |
| HAP4-M048  | (51) | TTCATGCCAGACATAGTCACCTACACCACGGTTATAGATGGGCTTTGCAA    |
| HAP4-R179  | (51) | TTCATGCCAGACATAGTCACCTACACCACGGTTATAGATGGGCTTTGCAA    |

Figure 5A

```
                        101                                               150
HAP1-M029    (101) GATAGGCCGGCTGGACGATGCAATGTCCCGATTCTGTCAGATGATTGATG
HAP1-M221    (101) GATAGGCCGGCTGGACGATGCAATGTCCCGATTCTGTCAGATGATTGATG
HAP1-M250    (101) GATAGGCCGGCTGGACGATGCAATGTCCCGATTCTGTCAGATGATTGATG
HAP1-M279    (101) GATAGGCCGGCTGGACGATGCAATGTCCCGATTCTGTCAGATGATTGATG
HAP1-M536    (101) GATAGGCCGGCTGGACGATGCAATGTCCCGATTCTGTCAGATGATTGATG
HAP1-M928    (101) GATAGGCCGGCTGGACGATGCAATGTCCCGATTCTGTCAGATGATTGATG
HAP1-M1400   (101) GATAGGCCGGCTGGACGATGCAATGTCCCGATTCTGTCAGATGATTGATG
HAP1-M1425   (101) GATAGGCCGGCTGGACGATGCAATGTCCCGATTCTGTCAGATGATTGATG
HAP1-M1498   (101) GATAGGCCGGCTGGACGATGCAATGTCCCGATTCTGTCAGATGATTGATG
HAP2-R158    (101) GATAGGCCGGCTGGACGATGCAATGTCCCGATTCTGTCAGATGATTGATG
HAP2-R159    (101) GATAGGCCGGCTGGACGATGCAATGTCCCGATTCTGTCAGATGATTGATG
HAP2-R162    (101) GATAGGCCGGCTGGACGATGCAATGTCCCGATTCTGTCAGATGATTGATG
HAP2-R163    (101) GATAGGCCGGCTGGACGATGCAATGTCCCGATTCTGTCAGATGATTGATG
HAP2-R166    (101) GATAGGCCGGCTGGACGATGCAATGTCCCGATTCTGTCAGATGATTGATG
HAP2-R174    (101) GATAGGCCGGCTGGACGATGCAATGTCCCGATTCTGTCAGATGATTGATG
HAP2-R396    (101) GATAGGCCGGCTGGACGATGCAATGTCCCGATTCTGTCAGATGATTGATG
HAP2-R424    (101) GATAGGCCGGCTGGACGATGCAATGTCCCGATTCTGTCAGATGATTGATG
HAP3-M144    (101) GATAGGCCGGCTGGACGATGCAATGTCCCGATTCTGTCAGATGATTGATG
HAP3-M172    (101) GATAGGCCGGCTGGACGATGCAATGTCCCGATTCTGTCAGATGATTGATG
HAP3-M187    (101) GATAGGCCGGCTGGACGATGCAATGTCCCGATTCTGTCAGATGATTGATG
HAP3-M331    (101) GATAGGCCGGCTGGACGATGCAATGTCCCGATTCTGTCAGATGATTGATG
HAP3-M682    (101) GATAGGCCGGCTGGACGATGCAATGTCCCGATTCTGTCAGATGATTGATG
HAP3-M687    (101) GATAGGCCGGCTGGACGATGCAATGTCCCGATTCTGTCAGATGATTGATG
HAP3-R633    (101) GATAGGCCGGCTGGACGATGCAATGTCCCGATTCTGTCAGATGATTGATG
HAP3-M1423   (101) GATAGGCCGGCTGGACGATGCAATGTCCCGATTCTGTCAGATGATTGATG
HAP4-M048    (101) GATAGGCCGGCTGGACGATGCAATGTCCCGATTCTGTCAGATGATTGATG
HAP4-R179    (101) GATAGGCCGGCTGGACGATGCAATGTCCCGATTCTGTCAGATGATTGATG 151                                               200
HAP1-M029    (151) ATGGATTGTCTCCCAATATCATAACATTTACGACCCTGATTCATGGGTTT
HAP1-M221    (151) ATGGATTGTCTCCCAATATCATAACATTTACGACCCTGATTCATGGGTTT
HAP1-M250    (151) ATGGATTGTCTCCCAATATCATAACATTTACGACCCTGATTCATGGGTTT
HAP1-M279    (151) ATGGATTGTCTCCCAATATCATAACATTTACGACCCTGATTCATGGGTTT
HAP1-M536    (151) ATGGATTGTCTCCCAATATCATAACATTTACGACCCTGATTCATGGGTTT
HAP1-M928    (151) ATGGATTGTCTCCCAATATCATAACATTTACGACCCTGATTCATGGGTTT
HAP1-M1400   (151) ATGGATTGTCTCCCAATATCATAACATTTACGACCCTGATTCATGGGTTT
HAP1-M1425   (151) ATGGATTGTCTCCCAATATCATAACATTTACGACCCTGATTCATGGGTTT
HAP1-M1498   (151) ATGGATTGTCTCCCAATATCATAACATTTACGACCCTGATTCATGGGTTT
HAP2-R158    (151) ATGGATTGTCTCCCAATATCATAACATTTACGACCCTGATTCATGGGTTT
HAP2-R159    (151) ATGGATTGTCTCCCAATATCATAACATTTACGACCCTGATTCATGGGTTT
HAP2-R162    (151) ATGGATTGTCTCCCAATATCATAACATTTACGACCCTGATTCATGGGTTT
HAP2-R163    (151) ATGGATTGTCTCCCAATATCATAACATTTACGACCCTGATTCATGGGTTT
HAP2-R166    (151) ATGGATTGTCTCCCAATATCATAACATTTACGACCCTGATTCATGGGTTT
HAP2-R174    (151) ATGGATTGTCTCCCAATATCATAACATTTACGACCCTGATTCATGGGTTT
HAP2-R396    (151) ATGGATTGTCTCCCAATATCATAACATTTACGACCCTGATTCATGGGTTT
HAP2-R424    (151) ATGGATTGTCTCCCAATATCATAACATTTACGACCCTGATTCATGGGTTT
HAP3-M144    (151) ATGGATTGTCTCCCAATATCATAACATTTACGACCCTGATTCATGGGTTT
HAP3-M172    (151) ATGGATTGTCTCCCAATATCATAACATTTACGACCCTGATTCATGGGTTT
HAP3-M187    (151) ATGGATTGTCTCCCAATATCATAACATTTACGACCCTGATTCATGGGTTT
HAP3-M331    (151) ATGGATTGTCTCCCAATATCATAACATTTACGACCCTGATTCATGGGTTT
HAP3-M682    (151) ATGGATTGTCTCCCAATATCATAACATTTACGACCCTGATTCATGGGTTT
HAP3-M687    (151) ATGGATTGTCTCCCAATATCATAACATTTACGACCCTGATTCATGGGTTT
HAP3-R633    (151) ATGGATTGTCTCCCAATATCATAACATTTACGACCCTGATTCATGGGTTT
HAP3-M1423   (151) ATGGATTGTCTCCCAATATCATAACATTTACGACCCTGATTCATGGGTTT
HAP4-M048    (151) ATGGATTGTCTCCCAATATCATAACATTTACGACCCTGATTCATGGGTTT
HAP4-R179    (151) ATGGATTGTCTCCCAATATCATAACATTTACGACCCTGATTCATGGGTTT
```

Figure 5B

```
                    201                                                  250
HAP1-M029   (201)   TCTATGTATGGCAAATGGGAGAAGGCTGAGGAACTATTTTATGAGATGAT
HAP1-M221   (201)   TCTATGTATGGCAAATGGGAGAAGGCTGAGGAACTATTTTATGAGATGAT
HAP1-M250   (201)   TCTATGTATGGCAAATGGGAGAAGGCTGAGGAACTATTTTATGAGATGAT
HAP1-M279   (201)   TCTATGTATGGCAAATGGGAGAAGGCTGAGGAACTATTTTATGAGATGAT
HAP1-M536   (201)   TCTATGTATGGCAAATGGGAGAAGGCTGAGGAACTATTTTATGAGATGAT
HAP1-M928   (201)   TCTATGTATGGCAAATGGGAGAAGGCTGAGGAACTATTTTATGAGATGAT
HAP1-M1400  (201)   TCTATGTATGGCAAATGGGAGAAGGCTGAGGAACTATTTTATGAGATGAT
HAP1-M1425  (201)   TCTATGTATGGCAAATGGGAGAAGGCTGAGGAACTATTTTATGAGATGAT
HAP1-M1498  (201)   TCTATGTATGGCAAATGGGAGAAGGCTGAGGAACTATTTTATGAGATGAT
HAP2-R158   (201)   TCTATGTATGGCAAATGGGAGAAGGCTGAGGAACTATTTTATGAGATGAT
HAP2-R159   (201)   TCTATGTATGGCAAATGGGAGAAGGCTGAGGAACTATTTTATGAGATGAT
HAP2-R162   (201)   TCTATGTATGGCAAATGGGAGAAGGCTGAGGAACTATTTTATGAGATGAT
HAP2-R163   (201)   TCTATGTATGGCAAATGGGAGAAGGCTGAGGAACTATTTTATGAGATGAT
HAP2-R166   (201)   TCTATGTATGGCAAATGGGAGAAGGCTGAGGAACTATTTTATGAGATGAT
HAP2-R174   (201)   TCTATGTATGGCAAATGGGAGAAGGCTGAGGAACTATTTTATGAGATGAT
HAP2-R396   (201)   TCTATGTATGGCAAATGGGAGAAGGCTGAGGAACTATTTTATGAGATGAT
HAP2-R424   (201)   TCTATGTATGGCAAATGGGAGAAGGCTGAGGAACTATTTTATGAGATGAT
HAP3-M144   (201)   TCTATGTATGGCAAATGGGAGAAGGCTGAGGAACTATTTTATGAGATGAT
HAP3-M172   (201)   TCTATGTATGGCAAATGGGAGAAGGCTGAGGAACTATTTTATGAGATGAT
HAP3-M187   (201)   TCTATGTATGGCAAATGGGAGAAGGCTGAGGAACTATTTTATGAGATGAT
HAP3-M331   (201)   TCTATGTATGGCAAATGGGAGAAGGCTGAGGAACTATTTTATGAGATGAT
HAP3-M682   (201)   TCTATGTATGGCAAATGGGAGAAGGCTGAGGAACTATTTTATGAGATGAT
HAP3-M687   (201)   TCTATGTATGGCAAATGGGAGAAGGCTGAGGAACTATTTTATGAGATGAT
HAP3-R633   (201)   TCTATGTATGGCAAATGGGAGAAGGCTGAGGAACTATTTTATGAGATGAT
HAP3-M1423  (201)   TCTATGTATGGCAAATGGGAGAAGGCTGAGGAACTATTTTATGAGATGAT
HAP4-M048   (201)   TCTATGTATGGCAAATGGGAGAAGGCTGAGGAACTATTTTATGAGATGAT
HAP4-R179   (201)   TCTATGTATGGCAAATGGGAGAAGGCTGAGGAACTATTTTATGAGATGAT 251                                                  300
HAP1-M029   (251)   GGATAGAGGCATTCCTCCTGATGTCACTATCTTCAGTGCAATGATAGATA
HAP1-M221   (251)   GGATAGAGGCATTCCTCCTGATGTCACTATCTTCAGTGCAATGATAGATA
HAP1-M250   (251)   GGATAGAGGCATTCCTCCTGATGTCACTATCTTCAGTGCAATGATAGATA
HAP1-M279   (251)   GGATAGAGGCATTCCTCCTGATGTCACTATCTTCAGTGCAATGATAGATA
HAP1-M536   (251)   GGATAGAGGCATTCCTCCTGATGTCACTATCTTCAGTGCAATGATAGATA
HAP1-M928   (251)   GGATAGAGGCATTCCTCCTGATGTCACTATCTTCAGTGCAATGATAGATA
HAP1-M1400  (251)   GGATAGAGGCATTCCTCCTGATGTCACTATCTTCAGTGCAATGATAGATA
HAP1-M1425  (251)   GGATAGAGGCATTCCTCCTGATGTCACTATCTTCAGTGCAATGATAGATA
HAP1-M1498  (251)   GGATAGAGGCATTCCTCCTGATGTCACTATCTTCAGTGCAATGATAGATA
HAP2-R158   (251)   GGATAGAGGCATTCCTCCTGATGTCACTATCTTCAGTGCAATGATAGATA
HAP2-R159   (251)   GGATAGAGGCATTCCTCCTGATGTCACTATCTTCAGTGCAATGATAGATA
HAP2-R162   (251)   GGATAGAGGCATTCCTCCTGATGTCACTATCTTCAGTGCAATGATAGATA
HAP2-R163   (251)   GGATAGAGGCATTCCTCCTGATGTCACTATCTTCAGTGCAATGATAGATA
HAP2-R166   (251)   GGATAGAGGCATTCCTCCTGATGTCACTATCTTCAGTGCAATGATAGATA
HAP2-R174   (251)   GGATAGAGGCATTCCTCCTGATGTCACTATCTTCAGTGCAATGATAGATA
HAP2-R396   (251)   GGATAGAGGCATTCCTCCTGATGTCACTATCTTCAGTGCAATGATAGATA
HAP2-R424   (251)   GGATAGAGGCATTCCTCCTGATGTCACTATCTTCAGTGCAATGATAGATA
HAP3-M144   (251)   GGATAGAGGCATTCCTCCTAATGTCAATACGTTCAATTCAATGATAGATA
HAP3-M172   (251)   GGATAGAGGCATTCCTCCTAATGTCAATACGTTCAATTCAATGATAGATA
HAP3-M187   (251)   GGATAGAGGCATTCCTCCTAATGTCAATACGTTCAATTCAATGATAGATA
HAP3-M331   (251)   GGATAGAGGCATTCCTCCTAATGTCAATACGTTCAATTCAATGATAGATA
HAP3-M682   (251)   GGATAGAGGCATTCCTCCTAATGTCAATACGTTCAATTCAATGATAGATA
HAP3-M687   (251)   GGATAGAGGCATTCCTCCTAATGTCAATACGTTCAATTCAATGATAGATA
HAP3-R633   (251)   GGATAGAGGCATTCCTCCTAATGTCAATACGTTCAATTCAATGATAGATA
HAP3-M1423  (251)   GGATAGAGGCATTCCTCCTAATGTCAATACGTTCAATTCAATGATAGATA
HAP4-M048   (251)   GGATAGAGGCATTCCTCCTGATGTCACTATCTTCAGTGCAATGATAGATA
HAP4-R179   (251)   GGATAGAGGCATTCCTCCTGATGTCACTATCTTCAGTGCAATGATAGATA
                                       *       *  **    *  *
```

Figure 5C

```
                    301                                                   350
HAP1-M029   (301)   GGCTATTCAAAGAAGGAAAGGTTACAGAGGCCCAAAAACTCTTTGATTTG
HAP1-M221   (301)   GGCTATTCAAAGAAGGAAAGGTTACAGAGGCCCAAAAACTCTTTGATTTG
HAP1-M250   (301)   GGCTATTCAAAGAAGGAAAGGTTACAGAGGCCCAAAAACTCTTTGATTTG
HAP1-M279   (301)   GGCTATTCAAAGAAGGAAAGGTTACAGAGGCCCAAAAACTCTTTGATTTG
HAP1-M536   (301)   GGCTATTCAAAGAAGGAAAGGTTACAGAGGCCCAAAAACTCTTTGATTTG
HAP1-M928   (301)   GGCTATTCAAAGAAGGAAAGGTTACAGAGGCCCAAAAACTCTTTGATTTG
HAP1-M1400  (301)   GGCTATTCAAAGAAGGAAAGGTTACAGAGGCCCAAAAACTCTTTGATTTG
HAP1-M1425  (301)   GGCTATTCAAAGAAGGAAAGGTTACAGAGGCCCAAAAACTCTTTGATTTG
HAP1-M1498  (301)   GGCTATTCAAAGAAGGAAAGGTTACAGAGGCCCAAAAACTCTTTGATTTG
HAP2-R158   (301)   GGCTATTCAAAGAAGGAAAGGTTACGGAGGCCCGAAAACTCTTTGATTTG
HAP2-R159   (301)   GGCTATTCAAAGAAGGAAAGGTTACGGAGGCCCGAAAACTCTTTGATTTG
HAP2-R162   (301)   GGCTATTCAAAGAAGGAAAGGTTACGGAGGCCCGAAAACTCTTTGATTTG
HAP2-R163   (301)   GGCTATTCAAAGAAGGAAAGGTTACGGAGGCCCGAAAACTCTTTGATTTG
HAP2-R166   (301)   GGCTATTCAAAGAAGGAAAGGTTACGGAGGCCCGAAAACTCTTTGATTTG
HAP2-R174   (301)   GGCTATTCAAAGAAGGAAAGGTTACGGAGGCCCGAAAACTCTTTGATTTG
HAP2-R396   (301)   GGCTATTCAAAGAAGGAAAGGTTACGGAGGCCCGAAAACTCTTTGATTTG
HAP2-R424   (301)   GGCTATTCAAAGAAGGAAAGGTTACGGAGGCCCGAAAACTCTTTGATTTG
HAP3-M144   (301)   GGCTATTCAAAGAAGGAAAGGTTACGGAGGCCCGAAAACTCTTTGATTTG
HAP3-M172   (301)   GGCTATTCAAAGAAGGAAAGGTTACGGAGGCCCGAAAACTCTTTGATTTG
HAP3-M187   (301)   GGCTATTCAAAGAAGGAAAGGTTACGGAGGCCCGAAAACTCTTTGATTTG
HAP3-M331   (301)   GGCTATTCAAAGAAGGAAAGGTTACGGAGGCCCGAAAACTCTTTGATTTG
HAP3-M682   (301)   GGCTATTCAAAGAAGGAAAGGTTACGGAGGCCCGAAAACTCTTTGATTTG
HAP3-M687   (301)   GGCTATTCAAAGAAGGAAAGGTTACGGAGGCCCGAAAACTCTTTGATTTG
HAP3-R633   (301)   GGCTATTCAAAGAAGGAAAGGTTACGGAGGCCCGAAAACTCTTTGATTTG
HAP3-M1423  (301)   GGCTATTCAAAGAAGGAAAGGTTACGGAGGCCCGAAAACTCTTTGATTTG
HAP4-M048   (301)   GGCTATTCAAAGAAGGAAAGGTTACAGAGGCCCAAAAACTCTTTTATTTG
HAP4-R179   (301)   GGCTATTCAAAGAAGGAAAGGTTACAGAGGCCCAAAAACTCTTTTATTTG
                                                 *        *            *

351                                                   400
HAP1-M029   (351)   ATGCCACGTGCAGGAGCTAAACCTGATGTTGTTTCTTATAATATAATGAT
HAP1-M221   (351)   ATGCCACGTGCAGGAGCTAAACCTGATGTTGTTTCTTATAATATAATGAT
HAP1-M250   (351)   ATGCCACGTGCAGGAGCTAAACCTGATGTTGTTTCTTATAATATAATGAT
HAP1-M279   (351)   ATGCCACGTGCAGGAGCTAAACCTGATGTTGTTTCTTATAATATAATGAT
HAP1-M536   (351)   ATGCCACGTGCAGGAGCTAAACCTGATGTTGTTTCTTATAATATAATGAT
HAP1-M928   (351)   ATGCCACGTGCAGGAGCTAAACCTGATGTTGTTTCTTATAATATAATGAT
HAP1-M1400  (351)   ATGCCACGTGCAGGAGCTAAACCTGATGTTGTTTCTTATAATATAATGAT
HAP1-M1425  (351)   ATGCCACGTGCAGGAGCTAAACCTGATGTTGTTTCTTATAATATAATGAT
HAP1-M1498  (351)   ATGCCACGTGCAGGAGCTAAACCTGATGTTGTTTCTTATAATATAATGAT
HAP2-R158   (351)   ATGCCACGTGCAGGAGCTAAACCTAATGTTGTTTCTTATAATACAATGAT
HAP2-R159   (351)   ATGCCACGTGCAGGAGCTAAACCTAATGTTGTTTCTTATAATACAATGAT
HAP2-R162   (351)   ATGCCACGTGCAGGAGCTAAACCTAATGTTGTTTCTTATAATACAATGAT
HAP2-R163   (351)   ATGCCACGTGCAGGAGCTAAACCTAATGTTGTTTCTTATAATACAATGAT
HAP2-R166   (351)   ATGCCACGTGCAGGAGCTAAACCTAATGTTGTTTCTTATAATACAATGAT
HAP2-R174   (351)   ATGCCACGTGCAGGAGCTAAACCTAATGTTGTTTCTTATAATACAATGAT
HAP2-R396   (351)   ATGCCACGTGCAGGAGCTAAACCTAATGTTGTTTCTTATAATACAATGAT
HAP2-R424   (351)   ATGCCACGTGCAGGAGCTAAACCTAATGTTGTTTCTTATAATACAATGAT
HAP3-M144   (351)   ATGCCACGTGCAGGAGCTAAACCTAATGTTGTTTCTTATAATACAATGAT
HAP3-M172   (351)   ATGCCACGTGCAGGAGCTAAACCTAATGTTGTTTCTTATAATACAATGAT
HAP3-M187   (351)   ATGCCACGTGCAGGAGCTAAACCTAATGTTGTTTCTTATAATACAATGAT
HAP3-M331   (351)   ATGCCACGTGCAGGAGCTAAACCTAATGTTGTTTCTTATAATACAATGAT
HAP3-M682   (351)   ATGCCACGTGCAGGAGCTAAACCTAATGTTGTTTCTTATAATACAATGAT
HAP3-M687   (351)   ATGCCACGTGCAGGAGCTAAACCTAATGTTGTTTCTTATAATACAATGAT
HAP3-R633   (351)   ATGCCACGTGCAGGAGCTAAACCTAATGTTGTTTCTTATAATACAATGAT
HAP3-M1423  (351)   ATGCCACGTGCAGGAGCTAAACCTAATGTTGTTTCTTATAATACAATGAT
HAP4-M048   (351)   ATGCCACGTGCAGGAGCTAAACCTAATGTTGTTTCTTATAATACAATGAT
HAP4-R179   (351)   ATGCCACGTGCAGGAGCTAAACCTAATGTTGTTTCTTATAATACAATGAT
                                            *                  *
```

Figure 5D

```
                      401                                                450
HAP1-M029    (401)    TCATGGGTATTTCATAGCTGGTGAAGTGGGCGAAGTGATGAAGCTCCTTG
HAP1-M221    (401)    TCATGGGTATTTCATAGCTGGTGAAGTGGGCGAAGTGATGAAGCTCCTTG
HAP1-M250    (401)    TCATGGGTATTTCATAGCTGGTGAAGTGGGCGAAGTGATGAAGCTCCTTG
HAP1-M279    (401)    TCATGGGTATTTCATAGCTGGTGAAGTGGGCGAAGTGATGAAGCTCCTTG
HAP1-M536    (401)    TCATGGGTATTTCATAGCTGGTGAAGTGGGCGAAGTGATGAAGCTCCTTG
HAP1-M928    (401)    TCATGGGTATTTCATAGCTGGTGAAGTGGGCGAAGTGATGAAGCTCCTTG
HAP1-M1400   (401)    TCATGGGTATTTCATAGCTGGTGAAGTGGGCGAAGTGATGAAGCTCCTTG
HAP1-M1425   (401)    TCATGGGTATTTCATAGCTGGTGAAGTGGGCGAAGTGATGAAGCTCCTTG
HAP1-M1498   (401)    TCATGGGTATTTCATAGCTGGTGAAGTGGGCGAAGTGATGAAGCTCCTTG
HAP2-R158    (401)    TCATGGGTATTTCATAGCTGGTGAAGTGGGCGAAGTGATGAAGCTCCTTG
HAP2-R159    (401)    TCATGGGTATTTCATAGCTGGTGAAGTGGGCGAAGTGATGAAGCTCCTTG
HAP2-R162    (401)    TCATGGGTATTTCATAGCTGGTGAAGTGGGCGAAGTGATGAAGCTCCTTG
HAP2-R163    (401)    TCATGGGTATTTCATAGCTGGTGAAGTGGGCGAAGTGATGAAGCTCCTTG
HAP2-R166    (401)    TCATGGGTATTTCATAGCTGGTGAAGTGGGCGAAGTGATGAAGCTCCTTG
HAP2-R174    (401)    TCATGGGTATTTCATAGCTGGTGAAGTGGGCGAAGTGATGAAGCTCCTTG
HAP2-R396    (401)    TCATGGGTATTTCATAGCTGGTGAAGTGGGCGAAGTGATGAAGCTCCTTG
HAP2-R424    (401)    TCATGGGTATTTCATAGCTGGTGAAGTGGGCGAAGTGATGAAGCTCCTTG
HAP3-M144    (401)    TCATGGGTATTTCATAGCTGGTGAAGTGGGCGAAGTGATGAAGCTCCTTG
HAP3-M172    (401)    TCATGGGTATTTCATAGCTGGTGAAGTGGGCGAAGTGATGAAGCTCCTTG
HAP3-M187    (401)    TCATGGGTATTTCATAGCTGGTGAAGTGGGCGAAGTGATGAAGCTCCTTG
HAP3-M331    (401)    TCATGGGTATTTCATAGCTGGTGAAGTGGGCGAAGTGATGAAGCTCCTTG
HAP3-M682    (401)    TCATGGGTATTTCATAGCTGGTGAAGTGGGCGAAGTGATGAAGCTCCTTG
HAP3-M687    (401)    TCATGGGTATTTCATAGCTGGTGAAGTGGGCGAAGTGATGAAGCTCCTTG
HAP3-R633    (401)    TCATGGGTATTTCATAGCTGGTGAAGTGGGCGAAGTGATGAAGCTCCTTG
HAP3-M1423   (401)    TCATGGGTATTTCATAGCTGGTGAAGTGGGCGAAGTGATGAAGCTCCTTG
HAP4-M048    (401)    TCATGGGTATTTCATAGCTGGTGAAGTGGGCGAAGTGATGAAGCTCCTTG
HAP4-R179    (401)    TCATGGGTATTTCATAGCTGGTGAAGTGGGCGAAGTGATGAAGCTCCTTG 451                                                500
HAP1-M029    (451)    ATGAGATGCTCTTGATTGGCTTGAAACCCGATGCTGTTATTTTTGCTACT
HAP1-M221    (451)    ATGAGATGCTCTTGATTGGCTTGAAACCCGATGCTGTTATTTTTGCTACT
HAP1-M250    (451)    ATGAGATGCTCTTGATTGGCTTGAAACCCGATGCTGTTATTTTTGCTACT
HAP1-M279    (451)    ATGAGATGCTCTTGATTGGCTTGAAACCCGATGCTGTTATTTTTGCTACT
HAP1-M536    (451)    ATGAGATGCTCTTGATTGGCTTGAAACCCGATGCTGTTATTTTTGCTACT
HAP1-M928    (451)    ATGAGATGCTCTTGATTGGCTTGAAACCCGATGCTGTTATTTTTGCTACT
HAP1-M1400   (451)    ATGAGATGCTCTTGATTGGCTTGAAACCCGATGCTGTTATTTTTGCTACT
HAP1-M1425   (451)    ATGAGATGCTCTTGATTGGCTTGAAACCCGATGCTGTTATTTTTGCTACT
HAP1-M1498   (451)    ATGAGATGCTCTTGATTGGCTTGAAACCCGATGCTGTTATTTTTGCTACT
HAP2-R158    (451)    ATGAGATGCTCTTGATTGGCTTGAAACCCGATGCTGTTTTTTTTGCTACT
HAP2-R159    (451)    ATGAGATGCTCTTGATTGGCTTGAAACCCGATGCTGTTTTTTTTGCTACT
HAP2-R162    (451)    ATGAGATGCTCTTGATTGGCTTGAAACCCGATGCTGTTTTTTTTGCTACT
HAP2-R163    (451)    ATGAGATGCTCTTGATTGGCTTGAAACCCGATGCTGTTTTTTTTGCTACT
HAP2-R166    (451)    ATGAGATGCTCTTGATTGGCTTGAAACCCGATGCTGTTTTTTTTGCTACT
HAP2-R174    (451)    ATGAGATGCTCTTGATTGGCTTGAAACCCGATGCTGTTTTTTTTGCTACT
HAP2-R396    (451)    ATGAGATGCTCTTGATTGGCTTGAAACCCGATGCTGTTTTTTTTGCTACT
HAP2-R424    (451)    ATGAGATGCTCTTGATTGGCTTGAAACCCGATGCTGTTTTTTTTGCTACT
HAP3-M144    (451)    ATGATATGCTCTTGATTGGCTTGAAACCCAATGCTGTTAACCTTAATACT
HAP3-M172    (451)    ATGATATGCTCTTGATTGGCTTGAAACCCAATGCTGTTAACCTTAATACT
HAP3-M187    (451)    ATGATATGCTCTTGATTGGCTTGAAACCCAATGCTGTTAACCTTAATACT
HAP3-M331    (451)    ATGATATGCTCTTGATTGGCTTGAAACCCAATGCTGTTAACCTTAATACT
HAP3-M682    (451)    ATGATATGCTCTTGATTGGCTTGAAACCCAATGCTGTTAACCTTAATACT
HAP3-M687    (451)    ATGATATGCTCTTGATTGGCTTGAAACCCAATGCTGTTAACCTTAATACT
HAP3-R633    (451)    ATGATATGCTCTTGATTGGCTTGAAACCCAATGCTGTTAACCTTAATACT
HAP3-M1423   (451)    ATGATATGCTCTTGATTGGCTTGAAACCCAATGCTGTTAACCTTAATACT
HAP4-M048    (451)    ATGAGATGCTCTTGATTGGCTTGAAACCCGATGCTGTTTTTTTTGCTACT
HAP4-R179    (451)    ATGAGATGCTCTTGATTGGCTTGAAACCCGATGCTGTTTTTTTTGCTACT
                          *                            *         ****  **
```

Figure 5E

```
                    501                                                   550
HAP1-M029   (501)  TTATTTGATGGCATGGTCTCTAAGGGATTGAATCCTGATGTTGACACATG
HAP1-M221   (501)  TTATTTGATGGCATGGTCTCTAAGGGATTGAATCCTGATGTTGACACATG
HAP1-M250   (501)  TTATTTGATGGCATGGTCTCTAAGGGATTGAATCCTGATGTTGACACATG
HAP1-M279   (501)  TTATTTGATGGCATGGTCTCTAAGGGATTGAATCCTGATGTTGACACATG
HAP1-M536   (501)  TTATTTGATGGCATGGTCTCTAAGGGATTGAATCCTGATGTTGACACATG
HAP1-M928   (501)  TTATTTGATGGCATGGTCTCTAAGGGATTGAATCCTGATGTTGACACATG
HAP1-M1400  (501)  TTATTTGATGGCATGGTCTCTAAGGGATTGAATCCTGATGTTGACACATG
HAP1-M1425  (501)  TTATTTGATGGCATGGTCTCTAAGGGATTGAATCCTGATGTTGACACATG
HAP1-M1498  (501)  TTATTTGATGGCATGGTCTCTAAGGGATTGAATCCTGATGTTGACACATG
HAP2-R158   (501)  TTATTTGATGGCATGGTCTCTAAGGGATTGAATCCTGATGTTGACACATG
HAP2-R159   (501)  TTATTTGATGGCATGGTCTCTAAGGGATTGAATCCTGATGTTGACACATG
HAP2-R162   (501)  TTATTTGATGGCATGGTCTCTAAGGGATTGAATCCTGATGTTGACACATG
HAP2-R163   (501)  TTATTTGATGGCATGGTCTCTAAGGGATTGAATCCTGATGTTGACACATG
HAP2-R166   (501)  TTATTTGATGGCATGGTCTCTAAGGGATTGAATCCTGATGTTGACACATG
HAP2-R174   (501)  TTATTTGATGGCATGGTCTCTAAGGGATTGAATCCTGATGTTGACACATG
HAP2-R396   (501)  TTATTTGATGGCATGGTCTCTAAGGGATTGAATCCTGATGTTGACACATG
HAP2-R424   (501)  TTATTTGATGGCATGGTCTCTAAGGGATTGAATCCTGATGTTGACACATG
HAP3-M144   (501)  TTACTTGATGGCATGCTCTCTATTGGCTTGAAACCAATGTTGACACATG
HAP3-M172   (501)  TTACTTGATGGCATGCTCTCTATTGGCTTGAAACCAAATGTTGACACATG
HAP3-M187   (501)  TTACTTGATGGCATGCTCTCTATTGGCTTGAAACCAAATGTTGACACATG
HAP3-M331   (501)  TTACTTGATGGCATGCTCTCTATTGGCTTGAAACCAAATGTTGACACATG
HAP3-M682   (501)  TTACTTGATGGCATGCTCTCTATTGGCTTGAAACCAAATGTTGACACATG
HAP3-M687   (501)  TTACTTGATGGCATGCTCTCTATTGGCTTGAAACCAAATGTTGACACATG
HAP3-R633   (501)  TTACTTGATGGCATGCTCTCTATTGGCTTGAAACCAAATGTTGACACATG
HAP3-M1423  (501)  TTACTTGATGGCATGCTCTCTATTGGCTTGAAACCAAATGTTGACACATG
HAP4-M048   (501)  TTATTTGATGGCATGGTCTCTAAGGGATTGAATCCTGATGTTGACACATG
HAP4-R179   (501)  TTATTTGATGGCATGGTCTCTAAGGGATTGAATCCTGATGTTGACACATG
                          *              *      **  *       *    **

551                                                   600
HAP1-M029   (551)  TAAGACTTTGATTGATAGCTGCTGTGAAGATGACAGGATAGAGGATATAT
HAP1-M221   (551)  TAAGACTTTGATTGATAGCTGCTGTGAAGATGACAGGATAGAGGATATAT
HAP1-M250   (551)  TAAGACTTTGATTGATAGCTGCTGTGAAGATGACAGGATAGAGGATATAT
HAP1-M279   (551)  TAAGACTTTGATTGATAGCTGCTGTGAAGATGACAGGATAGAGGATATAT
HAP1-M536   (551)  TAAGACTTTGATTGATAGCTGCTGTGAAGATGACAGGATAGAGGATATAT
HAP1-M928   (551)  TAAGACTTTGATTGATAGCTGCTGTGAAGATGACAGGATAGAGGATATAT
HAP1-M1400  (551)  TAAGACTTTGATTGATAGCTGCTGTGAAGATGACAGGATAGAGGATATAT
HAP1-M1425  (551)  TAAGACTTTGATTGATAGCTGCTGTGAAGATGACAGGATAGAGGATATAT
HAP1-M1498  (551)  TAAGACTTTGATTGATAGCTGCTGTGAAGATGACAGGATAGAGGATATAT
HAP2-R158   (551)  TAAGACTTTGATTGATAGCTGCTGTGAAGATGACAGGATAGAGGATATAT
HAP2-R159   (551)  TAAGACTTTGATTGATAGCTGCTGTGAAGATGACAGGATAGAGGATATAT
HAP2-R162   (551)  TAAGACTTTGATTGATAGCTGCTGTGAAGATGACAGGATAGAGGATATAT
HAP2-R163   (551)  TAAGACTTTGATTGATAGCTGCTGTGAAGATGACAGGATAGAGGATATAT
HAP2-R166   (551)  TAAGACTTTGATTGATAGCTGCTGTGAAGATGACAGGATAGAGGATATAT
HAP2-R174   (551)  TAAGACTTTGATTGATAGCTGCTGTGAAGATGACAGGATAGAGGATATAT
HAP2-R396   (551)  TAAGACTTTGATTGATAGCTGCTGTGAAGATGACAGGATAGAGGATATAT
HAP2-R424   (551)  TAAGACTTTGATTGATAGCTGCTGTGAAGATGACAGGATAGAGGATATAT
HAP3-M144   (551)  TAAGACTTTGATTGATAGCTGCTGTGAAGATGACAGGATAGAGGATATAT
HAP3-M172   (551)  TAAGACTTTGATTGATAGCTGCTGTGAAGATGACAGGATAGAGGATATAT
HAP3-M187   (551)  TAAGACTTTGATTGATAGCTGCTGTGAAGATGACAGGATAGAGGATATAT
HAP3-M331   (551)  TAAGACTTTGATTGATAGCTGCTGTGAAGATGACAGGATAGAGGATATAT
HAP3-M682   (551)  TAAGACTTTGATTGATAGCTGCTGTGAAGATGACAGGATAGAGGATATAT
HAP3-M687   (551)  TAAGACTTTGATTGATAGCTGCTGTGAAGATGACAGGATAGAGGATATAT
HAP3-R633   (551)  TAAGACTTTGATTGATAGCTGCTGTGAAGATGACAGGATAGAGGATATAT
HAP3-M1423  (551)  TAAGACTTTGATTGATAGCTGCTGTGAAGATGACAGGATAGAGGATATAT
HAP4-M048   (551)  TAAGACTTTGATTGATAGCTGCTGTGAAGATGACAGGATAGAGGATATAT
HAP4-R179   (551)  TAAGACTTTGATTGATAGCTGCTGTGAAGATGACAGGATAGAGGATATAT
```

Figure 5F

```
                        601                                              650
HAP1-M029    (601) TAACTCTGTTCCGAGAAATGTTGAGCAAGGCTGATAAGACTGACACTATC
HAP1-M221    (601) TAACTCTGTTCCGAGAAATGTTGAGCAAGGCTGATAAGACTGACACTATC
HAP1-M250    (601) TAACTCTGTTCCGAGAAATGTTGAGCAAGGCTGATAAGACTGACACTATC
HAP1-M279    (601) TAACTCTGTTCCGAGAAATGTTGAGCAAGGCTGATAAGACTGACACTATC
HAP1-M536    (601) TAACTCTGTTCCGAGAAATGTTGAGCAAGGCTGATAAGACTGACACTATC
HAP1-M928    (601) TAACTCTGTTCCGAGAAATGTTGAGCAAGGCTGATAAGACTGACACTATC
HAP1-M1400   (601) TAACTCTGTTCCGAGAAATGTTGAGCAAGGCTGATAAGACTGACACTATC
HAP1-M1425   (601) TAACTCTGTTCCGAGAAATGTTGAGCAAGGCTGATAAGACTGACACTATC
HAP1-M1498   (601) TAACTCTGTTCCGAGAAATGTTGAGCAAGGCTGATAAGACTGACACTATC
HAP2-R158    (601) TAACTCTGTTCCGAGAAATGTTGAGCAAGGCTGATAAGACTGACACTATC
HAP2-R159    (601) TAACTCTGTTCCGAGAAATGTTGAGCAAGGCTGATAAGACTGACACTATC
HAP2-R162    (601) TAACTCTGTTCCGAGAAATGTTGAGCAAGGCTGATAAGACTGACACTATC
HAP2-R163    (601) TAACTCTGTTCCGAGAAATGTTGAGCAAGGCTGATAAGACTGACACTATC
HAP2-R166    (601) TAACTCTGTTCCGAGAAATGTTGAGCAAGGCTGATAAGACTGACACTATC
HAP2-R174    (601) TAACTCTGTTCCGAGAAATGTTGAGCAAGGCTGATAAGACTGACACTATC
HAP2-R396    (601) TAACTCTGTTCCGAGAAATGTTGAGCAAGGCTGATAAGACTGACACTATC
HAP2-R424    (601) TAACTCTGTTCCGAGAAATGTTGAGCAAGGCTGATAAGACTGACACTATC
HAP3-M144    (601) TAACTCTGTTCCGAGAAATGTTGAGCAAGGCTGATAAGACTGACACTATC
HAP3-M172    (601) TAACTCTGTTCCGAGAAATGTTGAGCAAGGCTGATAAGACTGACACTATC
HAP3-M187    (601) TAACTCTGTTCCGAGAAATGTTGAGCAAGGCTGATAAGACTGACACTATC
HAP3-M331    (601) TAACTCTGTTCCGAGAAATGTTGAGCAAGGCTGATAAGACTGACACTATC
HAP3-M682    (601) TAACTCTGTTCCGAGAAATGTTGAGCAAGGCTGATAAGACTGACACTATC
HAP3-M687    (601) TAACTCTGTTCCGAGAAATGTTGAGCAAGGCTGATAAGACTGACACTATC
HAP3-R633    (601) TAACTCTGTTCCGAGAAATGTTGAGCAAGGCTGATAAGACTGACACTATC
HAP3-M1423   (601) TAACTCTGTTCCGAGAAATGTTGAGCAAGGCTGATAAGACTGACACTATC
HAP4-M048    (601) TAACTCTGTTCCGAGAAATGTTGAGCAAGGCTGATAAGACTGACACTATC
HAP4-R179    (601) TAACTCTGTTCCGAGAAATGTTGAGCAAGGCTGATAAGACTGACACTATC
```

SORGHUM FERTILITY RESTORER GENOTYPES AND METHODS OF MARKER-ASSISTED SELECTION

FIELD OF THE INVENTION

The invention relates to a *sorghum* (*Sorghum bicolor*) cms fertility restorer gene for the A1 cytoplasm and molecular markers, in particular simple sequence repeat markers (SSR markers) and single nucleotide polymorphisms (SNPs), linked to the restorer gene. The markers can be used to facilitate breeding in *sorghum*, for example to facilitate development of maintainer, restorer and cms *sorghum* lines used to make hybrids.

BACKGROUND OF THE INVENTION

*Sorghum* is a genus of about 20 species of grasses native to tropical and subtropical regions of Eastern Africa, with one species native to Mexico. *Sorghum* is cultivated in Southern Europe, Central and North America and Southern Asia. *Sorghum* is also known as Durra, Egyptian Millet, Feterita, Guinea Corn, Jowar, Juwar, Kaffircorn, Milo and Shallu. *Sorghum* is used for food, fodder and the production of alcoholic beverages. It is an important food crop in Africa, Central America and South Asia, especially for subsistence farmers. It is used to make such foods as couscous, *sorghum* flour, porridge and molasses. The leading producer of *sorghum* is the United States where it is primarily used as a maize substitute for livestock feed because the nutritional content of *sorghum* and maize is similar. *Sorghum* is usually used as a lower cost substitute for maize in livestock rations. *Sorghum* is also used to make ethanol and other industrial products.

*Sorghum* is in the same family as maize and has a similar growth habit, but with more tillers and a more extensively branched root system. *Sorghum* is more drought-resistant and heat-tolerant than maize. It requires an average temperature of at least 25° C. to produce maximum yields. *Sorghum*'s ability to thrive with less water than maize may be due to its ability to hold water in its foliage better than maize. *Sorghum* has a waxy coating on its leaves and stems which helps to keep water in the plant even in intense heat. Wild species of *sorghum* tend to grow to a height of 1.5 to 2 meters, however in order to improve harvestability, dwarfing genes have been selected in cultivated varieties and hybrids such that most cultivated varieties and hybrids grow to between 60 and 120 cm tall. It is commonly accepted that there are four dwarfing genes in *sorghum*.

Hybrid production in *sorghum* is accomplished by crossing a female line (cytoplasmic male sterile line derived from non-restorer germplasm) with a male line containing a restorer gene. Several *sorghum* restorer genes have been identified through mapping. Klein, et al., (2001) *Theor. Appl. Genet.* 102:1206-1212 have mapped Rf1 gene on LG-H (LG-08) for A1 type cytoplasm. Wen, et al., (2002) *Theor. Appl. Genet.* 104:577-585 have mapped Rf4 gene in A3 type cytoplasm. Tang, et al., (1996) *Plant J.* 10:123-133 and Tang, et al., (1998) *Genetics* 150:383-391 have mapped the Rf3 gene in A3 type cytoplasm.

Germplasm carrying a restorer gene is numerous and diverse. Developing males (restorers) takes relatively less effort than developing females. As a result, both private and public breeding programs have focused on development of male lines that carry a restorer gene. The pool of available non-restorer (female) germplasm is less diverse and receives less attention in the public sectors. Within private industry, considerable resources are devoted to developing non-restorer germplasm but this activity is limited by both the pool of available non-restorer germplasm and the need for confirming non-restorers by test-crossing with restorer lines and evaluating subsequent hybrids. Currently, breeders confine themselves to making largely restorer-by-restorer or non-restorer by non-restorer crosses and rarely make non-restorer by restorer crosses because of the tedious procedure of separating restorers and non-restorers in subsequent generations as well as the unpredictability of the results. Facilitating such crosses using a marker associated with a restorer gene would enhance the breeders' ability to diversify the germplasm base of the non-restorer population leading to enhanced genetic progress and improved inbreds and hybrids. A marker for a restorer gene would also allow breeders to use marker-assisted selection and to more rapidly phenotype germplasm with unknown restoration reaction allowing new germplasm to efficiently flow into the restorer and non-restorer germplasm pools.

SUMMARY OF THE INVENTION

An aspect of the invention is the identification of molecular markers for a restorer gene in *sorghum*.

First, a typical mapping approach was used to identify simple sequence repeat (SSR) markers for a restorer gene. The SSRs were mapped to chromosome 2 of the *sorghum* genome. A restorer gene is found in the region of two SSR markers, TS304T and TS050, as shown in FIG. 3.

Second, the nucleotide sequence between TS304T and TS050 was translated and searched for pentatrico peptide repeat (PPR) motifs. The PPR motif is found in many restorer genes, for example, it is found in the canola, *Arabidopsis*, petunia, rice and corn restorer genes. Five possible genes having the PPR motif were identified in the vicinity of the TS304T and TS050 markers. One of these genes, sPPR1, contains single nucleotide polymorphisms (SNPs) that segregate with either restorer lines or non-restorer (maintainer) lines.

Third, primers and probes specific for the SNPs in sPPR1 were identified. These were used to screen restorer and non-restorer lines. The SSR markers and the SNP markers can be used to screen restorer and non-restorer lines by marker assisted selection (MAS).

An aspect of the invention is to provide a use of an isolated or recombinant nucleic acid for detecting a *sorghum* restorer gene, wherein the nucleic acid comprises: (a) a polynucleotide sequence that is at least about 80% identical to any of the markers TS0304T, TS050, TS297T, TS080, TS391, CS060, TS298T, TS019N, CS050, TS055 as set forth in SEQ ID NO: 5, SEQ ID NO: 6, SEQ ID NO: 44, SEQ ID NO: 38, SEQ ID NO: 57, SEQ ID NO: 62, SEQ ID NO: 65 and SEQ ID NO: 54; (b) a polynucleotide sequence set forth in SEQ ID NO: 5, SEQ ID NO: 6, SEQ ID NO: 44, SEQ ID NO: 38, SEQ ID NO: 57, SEQ ID NO: 62, SEQ ID NO: 65 or SEQ ID NO: 54; (c) a fragment of (a) or (b) or (d) a complement of (a), (b) or (c).

Another aspect of the invention is to provide a use of a nucleic acid for identifying a *sorghum* fertility restorer wherein the nucleic acid localizes to a chromosome interval flanked on each side by loci having at least about 80% sequence identity to the marker pair of TS304T and TS050 having sequences set forth in SEQ ID NO: 5 and SEQ ID NO: 6, respectively. The loci can have at least about 90% sequence identity to the marker pair or the loci can have the same sequence identity as the marker pair.

Another aspect of the invention is to provide an isolated or recombinant nucleic acid comprising: (a) a polynucleotide sequence that is at least about 80% identical to the sequence set forth in SEQ ID NO: 1, SEQ ID NO: 2, SEQ ID NO: 3, SEQ ID NO: 4, SEQ ID NO: 36, SEQ ID NO: 37, SEQ ID NO: 42, SEQ ID NO: 43, SEQ ID NO: 45, SEQ ID NO: 46, SEQ ID NO: 55, SEQ ID NO: 56, SEQ ID NO: 58, SEQ ID NO: 59, SEQ ID NO: 60, SEQ ID NO: 61, SEQ ID NO: 63, SEQ ID NO: 64, SEQ ID NO: 52 or SEQ ID NO: 53 or (b) a polynucleotide sequence set forth in SEQ ID NO: 1, SEQ ID NO: 2, SEQ ID NO: 3, SEQ ID NO: 4, SEQ ID NO: 36, SEQ ID NO: 37, SEQ ID NO: 42, SEQ ID NO: 43, SEQ ID NO: 45, SEQ ID NO: 46, SEQ ID NO: 55, SEQ ID NO: 56, SEQ ID NO: 58, SEQ ID NO: 59, SEQ ID NO: 60, SEQ ID NO: 61, SEQ ID NO: 63, SEQ ID NO: 64, SEQ ID NO: 52 or SEQ ID NO: 53.

Another aspect of the invention is to provide an isolated or recombinant sPPR-containing nucleic acid comprising; (a) a polynucleotide sequence that is at least about 80% identical to the sequence set forth in SEQ ID NO: 7, SEQ ID NO: 8, SEQ ID NO: 9, SEQ ID NO: 10, SEQ ID NO: 11, SEQ ID NO: 12, SEQ ID NO: 13. SEQ ID NO: 14, SEQ ID NO: 15, SEQ ID NO: 16, SEQ ID NO: 22, SEQ ID NO: 23, SEQ ID NO: 24 or SEQ ID NO: 25 or (b) a polynucleotide sequence set forth in SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 22, SEQ ID NO: 23, SEQ ID NO: 24 or SEQ ID NO: 25.

Another aspect of the invention is to provide an isolated or recombinant nucleic acid comprising: (a) a polynucleotide sequence that is at least about 80% identical to the sequence set forth in SEQ ID NO: 26 or SEQ ID NO: 27 or (b) a polynucleotide sequence set forth in SEQ ID NO: 26 or SEQ ID NO: 27.

Another aspect of the invention is to provide an isolated or recombinant nucleic acid comprising: (a) a polynucleotide sequence that is at least about 80% identical to the sequence set forth in SEQ ID NO: 28, SEQ ID NO: 29, SEQ ID NO: 32 or SEQ ID NO: 33 or (b) a polynucleotide sequence set forth in SEQ ID NO: 28, SEQ ID NO: 29, SEQ ID NO: 32 or SEQ ID NO: 33.

Another aspect of the invention is to provide an isolated or recombinant nucleic acid comprising: (a) a polynucleotide sequence that is at least about 80% identical to the sequence set forth in SEQ ID NO: 30, SEQ ID NO: 31, SEQ ID NO: 34 or SEQ ID NO: 35 or (b) a polynucleotide sequence set forth in SEQ ID NO: 30, SEQ ID NO: 31, SEQ ID NO: 34 or SEQ ID NO: 35.

Another aspect of the invention is to provide an isolated or recombinant polypeptide comprising: (a) an amino acid sequence that is at least about 80% identical to the sequence set forth in SEQ ID NO: 17, SEQ ID NO: 18, SEQ ID NO: 19, SEQ ID NO: 20 or SEQ ID NO: 21 or (b) an amino acid sequence set forth in SEQ ID NO: 17, SEQ ID NO: 18, SEQ ID NO: 19, SEQ ID NO: 20 or SEQ ID NO: 21.

Another aspect of the invention is to provide a method of identifying a *sorghum* restorer plant by identifying an allele associated with a restorer gene, the method comprising: (a) detecting at least one nucleic acid from the *sorghum*, wherein the nucleic acid localizes to a chromosome interval flanked on each side by loci having at least about 80% sequence identity to the marker pair of TS304T and TS050 as set out in SEQ ID NO: 5 and SEQ ID NO: 6 respectively and (b) identifying the *sorghum* comprising the nucleic acid, thereby identifying the *sorghum* restorer plant. The loci can have at least about 90% sequence identity to the marker pair or the loci can have the same sequence identity as the marker pair. The *sorghum* can be a whole plant, a plant organ, a plant seed or a plant cell.

Another aspect of the invention is to provide a method of identifying a *sorghum* restorer by identifying an allele associated with a restorer gene, the method comprising; (a) detecting an allele from *sorghum*, wherein the allele is genetically linked to the markers of TS304T, TS050 or TS297T having the sequences set forth in SEQ ID NO:5 or SEQ ID NO: 6 or sequences having at least 80% identity thereto and (b) identifying the *sorghum* comprising the allele, thereby identifying the *sorghum* restorer for A1 cytoplasm plant. The markers can have at least about 90% sequence identity to SEQ ID NO:5 or SEQ ID NO: 6. The markers can have the same sequence identity as SEQ ID NO:5 or SEQ ID NO: 6. The *sorghum* can be a whole plant, a plant organ, a plant seed or a plant cell.

Another aspect of the invention is to provide a method for screening *sorghum* for presence or absence of a fertility restorer gene, the method comprising: (a) providing a DNA sample from *sorghum* and (b) amplifying DNA from the sample using primers comprising the sequences set forth in SEQ ID NO: 1 and SEQ ID NO: 2 or sequences having at least about 80% sequence identity thereto, as forward and reverse primers respectively for the marker TS304T. The method can further comprise: (c) identifying an allele at marker locus TS304T wherein the allele is selected from the group consisting of b, c, e, f, g, h, i, j, k, l, m, n, o, p, r, s, t, u, v, w or x, y, z, aa or bb, as set forth in Table 3, wherein the presence of allele b, c, e, f, g, h, i, j, y, z, aa or bb signifies presence of the restorer gene and wherein the presence of allele k, l, m, n, a, p, r, s, t, u, v, w or x signifies absence of the restorer gene.

Another aspect of the invention is to provide a method for screening *sorghum* for presence or absence of a fertility restorer gene, the method comprising: (a) providing a DNA sample from *sorghum* and (b) amplifying DNA from the sample using primers comprising the sequences set forth in SEQ ID NO: 3 and SEQ ID NO: 4 or sequences having at least about 80% sequence identity thereto, as forward and reverse primers respectively for the marker TS050. The method can further comprise: (c) identifying an allele at marker locus TS050 wherein the allele is selected from the group consisting of a, b, h, i or j as set forth in Table 3; wherein the presence of allele a or j signifies presence of the restorer gene and wherein the presence of allele b, h or i signifies absence of the restorer gene.

Another aspect of the invention is to provide a method for screening *sorghum* for presence or absence of a fertility restorer gene comprising: (a) providing a DNA sample from *sorghum* and (b) screening the DNA for a nucleic acid having the sequence set forth in sPPR1 gene or a sequence with at least about 80% identity thereto. The step of screening the DNA for the sPPR1 gene can comprise screening for nucleotides comprising the sequences set forth in SEQ ID NO: 7, SEQ ID NO: 8, SEQ ID NO: 22, SEQ ID NO: 23, SEQ ID NO: 24 or SEQ ID NO: 25. The step of screening the DNA for the sPPR1 gene can comprise amplification with nucleotides comprising the sequences set forth in SEQ ID NO: 30 and SEQ ID NO: 31 or sequences having at least about 80% sequence identity thereto, as forward and reverse primers and probing with nucleotides comprising the sequences set forth in SEQ ID NO: 28 and SEQ ID NO: 29 or sequences having at least about 80% sequence identity thereto. The step of screening the DNA for the sPPR1 gene can comprise amplification with nucleotides comprising the sequences set forth in SEQ ID NO: 34 and SEQ ID NO: 35 or sequences having at least about 80% sequence identity thereto, as forward and reverse primers and probing with nucleotides comprising the sequences set forth in SEQ ID NO: 32 and SEQ ID NO: 33 or sequences having at least about 80% sequence identity thereto. The fertility restorer gene can be present or absent.

In the methods described above, the *sorghum* can be a whole plant, a plant organ, a plant seed, a plant part or a plant cell.

Another aspect of the invention is to provide a method of introgressing a restorer gene into at least one progeny *sorghum*, the method comprising: (a) cross-pollinating the plant identified by the methods described above with a second *sorghum* plant that lacks the restorer detected in the identified plant and (b) identifying a progeny *sorghum* comprising the restorer gene.

Another aspect of the invention is to provide a method for breeding an F1 hybrid *sorghum* progeny plant by marker assisted selection (MAS), comprising: (a) crossing a first *sorghum* plant with a second *sorghum* plant, wherein the first *sorghum* plant comprises a fertility restorer gene; (b) harvesting seed from the first *sorghum* plant, the second *sorghum* plant or both the first *sorghum* plant and the second *sorghum* plant; (c) growing an F1 progeny plant from the seed from (b) and (d) determining whether the F1 progeny plant comprises the fertility restorer gene by screening for a restorer gene by the methods described above. The method can be used for breeding F1 progeny restorers or for breeding F1 progeny non-restorers (maintainers).

Another aspect of the invention is to provide a kit for screening *sorghum* for the fertility restorer gene, comprising: (a) probes to screen for the restorer allele and (b) optionally primers to amplify the restorer allele locus. The probes can be nucleotides comprising sequences set forth in SEQ ID NO: 28, SEQ ID NO: 29, SEQ ID NO: 32 or SEQ ID NO: 33. The primers can be nucleotides comprising sequences set forth in SEQ ID NO: 30, SEQ ID NO: 31, SEQ ID NO: 34 or SEQ ID NO: 35.

Another aspect of the invention is to provide a method of positional cloning of a nucleic acid, the method comprising: (a) providing a nucleic acid from a *sorghum*, which nucleic acid localizes to a chromosome interval flanked on each side by loci having at least about 80% sequence identity to the marker pair of TS304T and TS050 as set forth in SEQ ID NO: 5 and SEQ ID NO: 6 and (b) cloning the nucleic acid. The nucleic acid can comprise a subsequence of a chromosome interval defined by loci having at least about 80% sequence identity to the marker pairs of TS304T and TS050, as set forth in SEQ ID NO: 5 and SEQ ID NO: 6. The loci can have at least about 90% sequence identity to the marker pair or can have the same sequence as the marker pair.

Another aspect of the invention is to provide a method of identifying a candidate chromosome interval comprising a restorer gene from a monocot, the method comprising: (a) providing a nucleic acid cloned according to the method described above and (b) identifying a homologue of the nucleic acid in the monocot. The method can further compriseisolating the homologue. A nucleic acid from the isolated or recombinant nucleic acid is obtained and the homologue is identified in silica or in vitro under selective hybridization conditions. The monocot can be *sorghum*.

BRIEF DESCRIPTION OF THE FIGURES

FIG. 4 shows the alignment of the sPPR1, sPPR3, sPPR4 and sPPR5 genes.

FIG. 5 shows the alignment of sPPR1 haplotypes in restorer and non-restorer (maintainer) lines and shows with asterisks the single nucleotide polymorphisms associated with these lines.

DEFINITIONS

Figure 1:
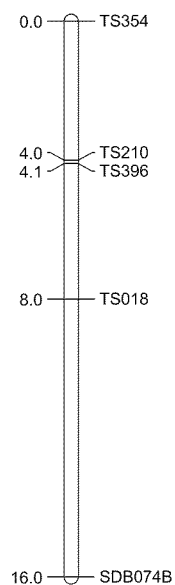
FIG. 1 is a representative diagram of LG-08 showing the SSR markers from the prior art of Klein, et al., 2001.
Figure 2:
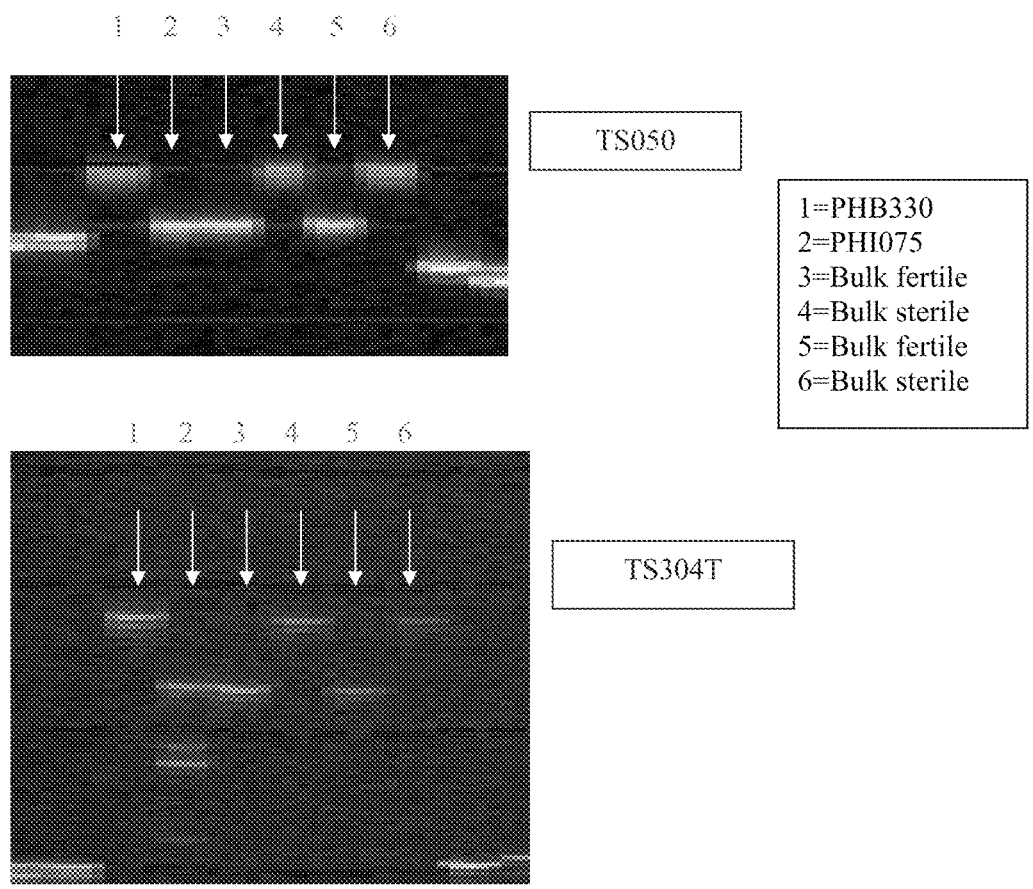
FIG. 2 is a photograph of the gel images of the TS050 and TS304T band patterns between parents and bulk populations.

Units, prefixes and symbols are denoted in their International System of Units (SI) accepted form. Unless otherwise indicated, nucleic acids are written left to right in 5' to 3' orientation and amino acid sequences are written left to right in amino to carboxy orientation. Numeric ranges recited within the specification are inclusive of the numbers defining the range and include each integer within the defined range. Nucleotides may be referred to herein by their one-letter symbols recommended by the IUPAC-IUBMB Nomenclature Commission. The terms defined below are more fully defined by reference to the specification as a whole. Section headings provided throughout the specification are provided for convenience and are not limited to the various objects and embodiments of the present invention.

The term "quantitative trait locus" or "QTL" refers to a polymorphic genetic locus with at least two alleles that reflect differential expression of a continuously distributed phenotypic trait.

The term "associated with" or "associated" in the context of this invention refers to, for example, a nucleic acid and a phenotypic trait, that are in linkage disequilibrium, i.e., the nucleic acid and the trait are found together in progeny plants more often than if the nucleic acid and phenotype segregated independently.

The term "linkage disequilibrium" refers to a non-random segregation of genetic loci. This implies that such loci are in sufficient physical proximity along a length of a chromosome that they tend to segregate together with greater than random frequency.

The term "genetically linked" refers to genetic loci that are in linkage disequilibrium and statistically determined not to assort independently. Genetically linked loci assort dependently from 51% to 99% of the time or any value there between, such as at least 60%, 70%, 80%, 90%, 95% or 99%.

The terms "proximal" or "distal" refer to a genetically linked marker being either closer (proximal) or further away (distal) to the marker region in reference.

The term "centiMorgan" means a unit of measure of recombination frequency. One centimorgan is equal to a 1% chance that a marker at one genetic locus will be separated from a marker at a second locus due to crossing over in a single generation. In human beings, 1 centiMorgan is equivalent, on average, to 1 million base pairs. It is a unit of crossover frequency in linkage maps of chromosomes equal to one hundredth of a morgan.

The term "marker" or "molecular marker" or "genetic marker" refers to a genetic locus (a "marker focus") used as a point of reference when identifying genetically linked loci such as a quantitative trait locus (QTL). The term may also refer to nucleic acid sequences complementary to the genomic sequences, such as nucleic acids used as probes or primers. The primers may be complementary to sequences upstream or downstream of the marker sequences. The term can also refer to amplification products associated with the marker. The term can also refer to alleles associated with the markers. Allelic variation associated with a phenotype allows use of the marker to distinguish germplasm on the basis of the sequence.

The term "interval" refers to a continuous linear span of chromosomal DNA with termini defined by and including molecular markers.

The term "simple sequence repeats" or "SSR" (also known as microsatellite) refers to a type of molecular marker that is based on short sequences of nucleotides (1-6 units in length) that are repeated in tandem. For example, a di-nucleotide repeat would be GAGAGAGA and a tri-nucleotide repeat would be ATGATGATGATG. It is believed that when DNA is being replicated, errors occur in the process and extra sets of these repeated sequences are added to the strand. Over time, these repeated sequences vary in length between one cultivar and another. An example of an allelic variation in SSRs would be: Allele A: GAGAGAGA (4 repeats of the GA sequence) and Allele B: GAGAGAGAGAGA (6 repeats of the GA sequence). These variations in length are easy to trace in the lab and allow tracking of genotypic variation in breeding programs.

The term "microsatellite" is an alternative term for SSR.

The term "single nucleotide polymorphism" or "SNP" is a DNA sequence variation occurring when a single nucleotide—A, T, C or G—in the genome (or other shared sequence) differs between members of a species (or between paired chromosomes in an individual). For example, two sequenced DNA fragments from different individuals, AAGCCTA to AAGCTTA, contain a difference in a single nucleotide. In this case we say that there are two alleles: C and T. Almost all common SNPs have only two alleles.

The term "cms" or "cytoplasmic male sterility" means a genetic condition due to faulty functioning of mitochondria in pollen development, preventing the formation of pollen. It is commonly found or inducible in many plant species and exploited for some $F_1$ hybrid seed programs.

The term "restorer" means the gene that restores fertility to a cms plant. The term "restorer" may also mean the plant or line carrying a restorer gene.

The term "maintainer" refers to a plant that when crossed with the cms plant does not restore fertility, and maintains sterility. The maintainer is used to propagate the cms line. It can also be referred to as a non-restorer line The terms "nucleic acid," "polynucleotide," "polynucleotide sequence" and "nucleic acid sequence" refer to single-stranded or double-stranded deoxyribonucleotide or ribonucleotide polymers, or chimeras thereof. As used herein, the terms can additionally or alternatively include analogs of naturally occurring nucleotides having the essential nature of natural nucleotides in that they hybridize to single-stranded nucleic acids in a manner similar to naturally occurring nucleotides (e.g., peptide nucleic acids). Unless otherwise indicated, a particular nucleic acid sequence of this invention optionally encompasses complementary sequences, in addition to the sequence explicitly indicated. The term "gene" is used to refer to, e.g., a cDNA and an mRNA encoded by the genomic sequence, as well as to that genomic sequence.

The term "homologous" refers to nucleic acid sequences that are derived from a common ancestral gene through natural or artificial processes (e.g., are members of the same gene family) and thus, typically, share sequence similarity. Typically, homologous nucleic acids have sufficient sequence identity that one of the sequences or its complement is able to selectively hybridize to the other under selective hybridization conditions. The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences have about at least 80% sequence identity, often at least 90% sequence identity and may have 95%, 97%, 99% or 100% sequence identity with each other. A nucleic acid that exhibits at least some degree of homology to a reference nucleic acid can be unique or identical to the reference nucleic acid or its complementary sequence.

The term "isolated" refers to material, such as a nucleic acid or a protein, which is substantially free from components that normally accompany or interact with it in its naturally occurring environment. The isolated material optionally comprises material not found with the material in its natural environment, e.g., a cell. In addition, if the material is in its natural environment, such as a cell, the material has been placed at a location in the cell (e.g., genome or subcellular organelle) not native to a material found in that environment. For example, a naturally occurring nucleic acid (e.g., a promoter) is considered to be isolated if it is introduced by non-naturally occurring means to a locus of the genome not native to that nucleic acid. Nucleic acids which are "isolated" as defined herein, are also referred to as "heterologous" nucleic acids.

The term "recombinant" indicates that the material (e.g., a nucleic acid or protein) has been synthetically (non-naturally) altered by human intervention. The alteration to yield the synthetic material can be performed on the material within or removed from its natural environment or state. For example, a naturally occurring nucleic acid is considered a recombinant nucleic acid if it is altered, or if it is transcribed from DNA which has been altered, by means of human intervention performed within the cell from which it originates. See, e.g., "Compounds and Methods for Site Directed Mutagenesis in Eukaryotic Cells", Kmiec, U.S. Pat. No. 5,565,350; "in Vivo Homologous Sequence Targeting in Eukaryotic Cells". Zarling, et al., PCT/US93/03868.

The term "introduced" when referring to a heterologous or isolated nucleic acid refers to the incorporation of a nucleic acid into a eukaryotic or prokaryotic cell where the nucleic acid can be incorporated into the genome of the cell (e.g., chromosome, plasmid, plastid or mitochondrial DNA), converted into an autonomous replicon or transiently expressed (e.g., transfected mRNA). The term includes such nucleic acid introduction means as "transfection," "transformation" and "transduction."

The term "host cell" means a cell which contains a heterologous nucleic acid, such as a vector and supports the replication and/or expression of the nucleic acid. Host cells may be prokaryotic cells such as *E. coli* or eukaryotic cells such as plant, yeast, insect, amphibian or mammalian cells. Preferably, host cells are monocotyledonous or dicotyledonous plant cells. In the context of the invention, one particularly preferred monocotyledonous host cell is a *sorghum* host cell.

The term "transgenic plant" refers to a plant which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to refer to any cell, cell line, callus, tissue, plant part or plant, the genotype of which has been altered by the presence of heterologous nucleic acid including those transgenic organisms or cells initially so altered, as well as those created by crosses or asexual propagation from the initial transgenic organism or cell. The term "transgenic" as used herein does not encompass the alteration of the genome (chromosomal or extra-chromosomal) by conventional plant breeding methods (i.e., crosses) or by naturally occurring events such as random cross-fertilization, non-recombinant viral infection, non-recombinant bacterial transformation, non-recombinant transposition or spontaneous mutation.

The term "crossed" or "cross" in the context of this invention means the fusion of gametes via pollination to produce progeny (i.e., cells, seeds or plants). The term encompasses both sexual crosses (the pollination of one plant by another) and selfing (self-pollination, i.e., when the pollen and ovule are from the same plant or from genetically identical plants).

The term "introgression" refers to the transmission of a desired allele of a genetic locus from one genetic background to another. For example, introgression of a desired allele at a specified locus can be transmitted to at least one progeny plant via a sexual cross between two parent plants, where at least one of the parent plants has the desired allele within its genome. Alternatively, for example, transmission of an allele can occur by recombination between two donor genomes, e.g., in a fused protoplast, where at least one of the donor protoplasts has the desired allele in its genome. The desired allele can be, e.g., a transgene or a selected allele of a marker or quantitative trait locus.

DESCRIPTION OF THE INVENTION

The invention relates to the identification of genetic markers for a restorer gene in *sorghum*. The invention also relates to the identification of genes comprising PPR motifs that segregate with the restorer phenotype. The genes comprising the PPR motif were identified by first identifying the genetic markers, e.g., marker loci and nucleic acids corresponding to (or derived from) these marker loci, such as probes and amplification products useful for genotyping plants, that correlate with a restorer gene in *sorghum*. The markers and PPR genes of the present invention are used to identify plants, particularly *sorghum* plants that have a restorer gene. The PPR genes themselves can serve as markers for a restorer gene. Accordingly, the term 'marker' as used in the present invention, may include the PPR genes themselves. One could also use these markers and PPR genes to find homologous markers and PPR genes in corn or other species. Accordingly, the PPR genes, and/or the markers associated with a restorer gene, are useful for identification, selection and breeding of restorer plants and non-restorer plants.

Markers

The present invention provides molecular markers, (i.e. including marker loci and nucleic acids corresponding to (or derived from) these marker loci, such as probes and amplification products) useful for genotyping plants, correlated with a restorer gene in *Sorghum*, for example TS050, TS304T and the sPPR genes described below. Such molecular markers are useful for selecting plants that carry a restorer gene or that do not carry a restorer gene. Accordingly, these markers are useful for marker assisted selection (MAS) and breeding of restorer lines and identification of non-restorer lines. The markers of the invention are also used to identify and define chromosome intervals corresponding to a restorer gene. A restorer gene can be isolated by positional cloning, e.g. of the genetic interval defined by a pair of markers described herein or subsequences of an interval defined by and including such markers. In addition, a restorer gene isolated from one organism, e.g. *sorghum*, can, in turn, serve to isolate homologues of a restorer gene in other organisms, including a variety of commercially important monocots, such as maize.

As is known to those skilled in the art, there are many kinds of molecular markers. For example, molecular markers can include restriction fragment length polymorphisms (RFLP), random amplified polymorphic DNA (RAPD), amplified fragment length polymorphisms (AFLP), single nucleotide polymorphisms (SNP) or simple sequence repeats (SSR).

Simple sequence repeats (SSR) or microsatellites are regions of DNA where one to a few bases are tandemly repeated for few to hundreds of times. For example, a di-nucleotide repeat would resemble CACACACA and a tri-nucleotide repeat would resemble ATGATGATGATG. Simple sequence repeats are thought to be generated due to slippage mediated errors during DNA replication, repair and recombination. Over time, these repeated sequences vary in length between one cultivar and another. An example of allelic variation in SSRs would be: Allele A being GAGAGAGA (4 repeats of the GA sequence) and allele B being GAGAGAGAGA (6 repeats of the GA sequence). When SSRs occur in a coding region, their survival depends on their impact on structure and function of the encoded protein. Since repeat tracks are prone to DNA-slippage mediated expansions/deletions, their occurrences in coding regions are limited by non-perturbation of the reading frame and tolerance of expanding amino acid stretches in the encoded proteins. Among all possible SSRs, tri-nucleotide repeats or multiples thereof are more common in coding regions.

A single nucleotide polymorphism (SNP) is a DNA sequence variation occurring when a single nucleotide—A, T, C or G—differs between members of a species (or between paired chromosomes in an individual). For example, two sequenced DNA fragments from two individuals, AAGCCTA to AAGCTTA, contain a difference in a single nucleotide. In this case, there are two alleles: C and T.

There are approximately 3000 molecular markers identified in *sorghum* and a genetic linkage map corresponding to the 10 *sorghum* chromosomes has been developed. (Menz, et al., (2002) *Plant Molecular Biology* 48:483-499). Recently, the *sorghum* genome has been sequenced (Paterson, et al., (January 2009) *Nature* 457:551-556, details also found in the U.S. Department of Energy's Joint Genome Institute website at genome.jgi-psf.org/Sorbi1/Sorbi1.info.html).

It will be noted that, regardless of their molecular nature, e.g., whether the marker is an SSR, AFLP, RFLP, etc., markers are typically strain specific. That is, a particular marker, such as the exemplary markers of the invention described above, is defined relative to the parental lines of interest. For each marker locus, restorer-associated, and conversely, non-restorer associated alleles are identified for each pair of parental lines. Following correlation of specific alleles with restoration or non-restoration in parents of a cross, the marker can be utilized to identify progeny with genotypes that correspond to the desired phenotype.

Linked Markers

Figure 3:
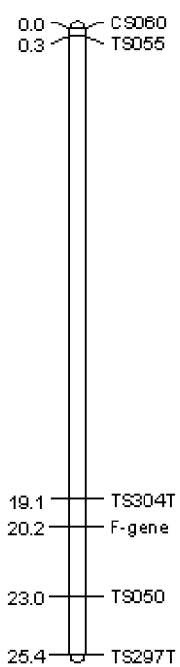
FIG. 3 is a linkage map showing the location of the restorer gene on LG-02 mapped with recombinant inbred line (RIL) population derived from PHB330×PH1075.
Figure 7:
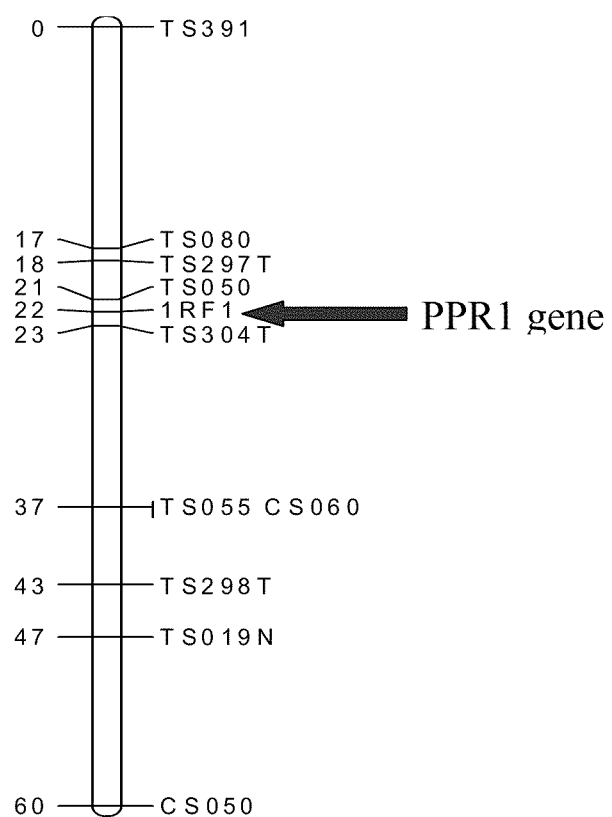
FIG. 7 is the linkage map of *sorghum* chromosome 2 (LG_02 (LG_B)) and the position of the sPPR1 gene.

FIG. 3 and FIG. 7 provide linked markers that can be used in addition to, or in place of, TS050 and TS304T for the purpose of mapping and isolating a restorer gene. Those of skill in the art will recognize that additional molecular markers can be identified within the intervals defined by the above described pair of markers. Such markers are also genetically linked to a restorer gene, and are within the scope of the present invention. Markers can be identified by any of a variety of genetic or physical mapping techniques. Methods of determining whether markers are genetically linked to a restorer gene are known to those of skill in the art and include, for example, interval mapping (Lander and Botstein, (1989) *Genetics* 121:185), regression mapping (Haley and Knott, (1992) *Heredity* 69:315) or MQM mapping (Jansen, (1994) *Genetics* 138:871). In addition, such physical mapping techniques as chromosome walking, contig mapping and assembly, and the like, can be employed to identify and isolate additional sequences useful as markers in the context of the present invention.

Homologous Markers

In addition, the markers disclosed herein (including TS304T, TS050, other SSRs, SNPs and the sPPR sequences disclosed herein) and other markers linked to a restorer gene are useful for the identification of homologous marker sequences with utility in identifying a restorer gene in different lines, varieties or species of monocots. Such homologous markers are also a feature of the invention.

Homologous markers can be identified by selective hybridization to a reference sequence. The reference sequence is typically a unique sequence, such as unique oligonucleotide primer sequences, ESTs, amplified fragments (e.g., corresponding to AFLP markers) and the like, derived from the marker loci, TS304T, TS050 and other marker loci linked to a restorer gene or its complement. In the case of markers of the present invention, (for example, but not limited to, TS304T, TS050, other SSRs, SNPs and sPPR primer sequences that hybridize to homologous reference sequences and amplify corresponding markers), are encompassed in the invention.

Two single-stranded nucleic acids "hybridize" when they form a double-stranded duplex. The double stranded region can include the full-length of one or both of the single-stranded nucleic acids or all of one single stranded nucleic acid and a subsequence of the other single-stranded nucleic acid or the double stranded region can include a subsequence of each nucleic acid. Selective hybridization conditions distinguish between nucleic acids that are related, e.g., share significant sequence identity with the reference sequence (or its complement) and those that associate with the reference sequence in a non-specific manner. Generally, selective hybridization conditions are those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Selective hybridization conditions may also be achieved with the addition of destabilizing agents such as formamide. Selectivity can be achieved by varying the stringency of the hybridization and/or wash conditions. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C. and a wash in 0.5× to 1×SSC at 55 to 60° C. Exemplary high stringency conditions include hybridization in 50% formamide, 1 M NaCl, 1% SDS at 37° C. and a wash in 0.1×SSC at 60 to 65° C.

Specificity is typically a function of post-hybridization washes, with the critical factors being ionic strength and temperature of the final wash solution. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3 or 4° C. lower than the thermal melting point ($T_m$); moderately stringent conditions can utilize a hybridization and/or wash at 6, 7, 8, 9 or 10° C. lower than the thermal melting point ($T_m$); low stringency conditions can utilize a hybridization and/or wash at 11, 12, 13, 14, 15 or 20° C. lower than the thermal melting point ($T_m$).

The $T_m$ is the temperature (under defined ionic strength and pH) at which 50% of a complementary target sequence hybridizes to a perfectly matched probe. For DNA-DNA hybrids, the $T_m$ can be approximated from the equation of Meinkoth and Wahl, (1984) *Anal. Biochem.* 138:267-284: $T_m$=81.5° C.+16.6 (log M)+0.41 (% GC)−0.61 (% form)−500/L, where M is the molarity of monovalent cations, % GC is the percentage of guanosine and cytosine nucleotides in the DNA, % form is the percentage of formamide in the hybridization solution and L is the length of the hybrid in base pairs. $T_m$ is reduced by about 1° C. for each 1% of mismatching; thus, $T_m$, hybridization and/or wash conditions can be adjusted to hybridize to sequences of the desired identity. For example, if sequences with ≥90% identity are sought, the $T_m$ can be decreased 10° C.

Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. Hybridization and/or wash conditions can be applied for at least 10, 30, 60, 90, 120 or 240 minutes. An extensive guide to the hybridization of nucleic acids is found in Tijssen, (1993) *Laboratory Techniques in Biochemistry and Molecular Biology—Hybridization with Nucleic Acid Probes* Part I, Chapter 2 "Overview of principles of hybridization and the strategy of nucleic acid probe assays" Elsevier, New York. General Texts which discuss considerations relevant to nucleic acid hybridization, the selection of probes and buffer and incubation conditions, and the like, as well as numerous other topics of interest in the context of the present invention (e.g., cloning of nucleic acids which correspond to markers, sequencing of cloned markers, the use of promoters, vectors, etc.) can be found in Berger and Kimmel, (1987) *Guide to Molecular Cloning Techniques, Methods in Enzymology* vol. 152, Academic Press, Inc., San Diego ("Berger"); Sambrook, et al., (2001) *Molecular Cloning—A Laboratory Manual*, 3$^{rd}$ ed. Vols. 1-3, Cold Spring Harbor Laboratory, Cold Spring Harbor ("Sambrook") and Ausubel, et al., (eds) (supplemented through 2001) *Current Protocols in Molecular Biology*, John Wiley and Sons, Inc., ("Ausubel").

In addition to hybridization methods described above, homologs of the markers of the invention can be identified in silica using any of a variety of sequence alignment and comparison protocols. For the purposes of the ensuing discussion, the following terms are used to describe the sequence relationships between a marker nucleotide sequence and a reference polynucleotide sequence:

A "reference sequence" is a defined sequence used as a basis for sequence comparison with a test sequence, e.g., a candidate marker homolog, of the present invention. A reference sequence may be a subsequence or the entirety of a specified sequence; for example, a segment of a full-length cDNA or gene sequence or the complete cDNA or gene sequence.

As used herein, a "comparison window" is a contiguous and specified segment, (e.g., a subsequence) of a polynucleotide/polypeptide sequence to be compared to a reference sequence. The segment of the polynucleotide/polypeptide sequence in the comparison window can include one or more additions or deletions (i.e., gaps) with respect to the reference sequence, which (by definition) does not comprise addition(s) or deletion(s), for optimal alignment of the two sequences. An optimal alignment of two sequences yields the fewest number of unlike nucleotide/amino acid residues in a comparison window. Generally, the comparison window is at least 20 contiguous nucleotide/amino acid residues in length, and optionally can be 30, 40, 50, 100 or longer. Those of skill in the art understand that to avoid a falsely high similarity between two sequences, due to inclusion of gaps in the polynucleotide/polypeptide sequence, a gap penalty is typically assessed and is subtracted from the number of matches.

"Sequence identity" or "identity" in the context of two nucleic acid or polypeptide sequences refers to residues that are the same in both sequences when aligned for maximum correspondence over a specified comparison window.

"Percentage sequence identity" refers to the value determined by comparing two optimally aligned sequences over a comparison window. The percentage is calculated by determining the number of positions at which both sequences have the same nucleotide or amino acid residue (matched positions), dividing the number of matched positions by the total number of positions in the comparison window and multiplying the result by 100 to yield the percentage of sequence identity.

When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ by conservative substitutions, the percent sequence identity may be adjusted upwards to correct for the conservative nature of the substitution. Sequences which differ by such conservative substitutions are said to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, (1988) *Computer Applic. Biol. Sci* 4:11-17, e.g., as implemented in the program PC/GENE (Intelligenetics, Mountain View, Calif., USA).

Methods of alignment of sequences for comparison are well-known in the art. Optimal alignment of sequences for comparison may be conducted by the local homology algorithm of Smith and Waterman, (1981) *Adv. Appl. Math.* 2:482; by the homology alignment algorithm of Needleman and Wunsch, (1970) *J. Mol. Biol.* 48:443; by the search for similarity method of Pearson and Lipman, (1988) *Proc. Natl. Acad. Sci. USA* 85:2444; by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package®, GCG® programs (Accelrys, Inc., San Diego, Calif.; the CLUSTAL program is well described by Higgins and Sharp, (1988) *Gene* 73:237-244; Higgins and Sharp, (1989) *CABIOS* 5:151-153; Corpet, et al., (1988) *Nucleic Acids Research* 16:10881-90; Huang, et al., (1992) *Computer Applications in the Biosciences* 8:155-65 and Pearson, et al., (1994) *Methods in Molecular Biology* 24:307-331.

The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences and TBLASTX for nucleotide query sequences against nucleotide database sequences, with translation of both to protein. See, e.g., *Current Protocols in Molecular Biology*, Chapter 19, Ausubel, et al., Eds., (1995) Greene Publishing and Wiley-Interscience, New York; Altschul, et al., (1990) *J. Mol. Biol.* 215:403-410 and Altschul, et al., (1997) *Nucleic Acids Res.* 25:3389-3402.

Software for performing BLAST analyses is publicly available, e.g., through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=-4, and a comparison of both strands. For amino acid sequences, the BLASTP program uses as defaults a wordlength (W) of 3, an expectation (E) of 10, and the BLOSUM62 scoring matrix (see, e.g., Henikoff and Henikoff, (1989) *Proc. Natl. Acad. Sci. USA* 89:10915).

In addition to calculating percent sequence identity, the BLAST algorithm also performs a statistical analysis of the similarity between two sequences (see, e.g., Karlin and Altschul, (1993) *Proc. Nall Acad. ScL USA* 90:5873-5877). One measure of similarity provided by the BLAST algorithm is the smallest sum probability (P(N)), which provides an indication of the probability that a match between two nucleotide or amino acid sequences would occur by chance.

BLAST searches assume that proteins can be modeled as random sequences. However, many real proteins comprise regions of nonrandom sequences which may be homopolymeric tracts, short-period repeats or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, (1993) *Comput. Chem.* 17:149-163) and XNU (Claverie and States, (1993) *Comput. Chem.* 17:191-201) low-complexity filters can be employed alone or in combination.

Unless otherwise stated, nucleotide and protein identity/similarity values provided herein are calculated using GAP (GCG Version 10) under default values.

GAP (Global Alignment Program) can also be used to compare a polynucleotide or polypeptide of the present invention with a reference sequence. GAP uses the algorithm of Needleman and Wunsch, (1970) *J. Mol. Biol.* 48:443-453, that has been shown to be equivalent to Sellers (Siam, (1974) *Applied Math* 26:787-793). GAP considers all possible alignments and gap positions between two sequences and creates a global alignment that maximizes the number of matched residues and minimizes the number of size of gaps. A scoring matrix is used to assign values for symbol matches. In addition, a gap creation penalty and a gap extension penalty are required to limit the insertion of gaps into the alignment. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package® for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 100. Thus, for example, the gap creation and gap extension penalties can each independently be: 0, 1, 2, 3, 4, 5, 6, 7, 8, 9, 10, 15, 20, 30, 40, 50, 60 or greater.

GAP presents one member of the family of best alignments. There may be many members of this family, but no other member has a better quality. GAP displays four figures of merit for alignments: Quality, Ratio, Identity and Similarity. The Quality is the metric maximized in order to align the sequences. Ratio is the quality divided by the number of bases in the shorter segment Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package® is BLOSUM62 (see, e.g., Henikoff and Henikoff, (1989) *Proc. Natl. Acad. Sci. USA* 89:10915).

Multiple alignment of the sequences can be performed using the CLUSTAL method of alignment (Higgins and Sharp, (1989) *CABIOS* 5:151-153) with the default parameters (GAP PENALTY=10, GAP LENGTH PENALTY=10). Default parameters for pairwise alignments using the CLUSTAL method are KTUPLE 1, GAP PENALTY=3, WINDOW=5 and DIAGONALS SAVED=5.

The percentage sequence identity of a homologous marker to its reference marker (e.g., any one of TS304T, TS050, sPP genes and other linked markers) is typically at least 80% and, rounded upwards to the nearest integer, can be expressed as an integer selected from the group of integers between 80 and 99. Thus, for example, the percentage sequence identity to a reference sequence can be at least 80%, 85%, 90%, 95%, 97% or 99%. Sequence identity can be calculated using, for example, the BLAST, CLUSTALW or GAP algorithms under default conditions.

Detection of Marker Loci

Markers corresponding to genetic polymorphisms between members of a population can be detected by numerous methods, well-established in the art (e.g., restriction fragment length polymorphisms, isozyme markers, allele specific hybridization (ASH), amplified variable sequences of the plant genome, self-sustained sequence replication, simple sequence repeat (SSR), single nucleotide polymorphism (SNP) or amplified fragment length polymorphisms (AFLP)).

The majority of genetic markers rely on one or more property of nucleic acids for their detection. For example, some techniques for detecting genetic markers utilize hybridization of a probe nucleic acid to nucleic acids corresponding to the genetic marker. Hybridization formats include but are not limited to, solution phase, solid phase, mixed phase or in situ hybridization assays. Markers which are restriction fragment length polymorphisms (RFLP), are detected by hybridizing a probe (which is typically a sub-fragment or a synthetic oligonucleotide corresponding to a sub-fragment of the nucleic acid to be detected) to restriction digested genomic DNA. The restriction enzyme is selected to provide restriction fragments of at least two alternative (or polymorphic) lengths in different individuals and will often vary from line to line. Determining a (one or more) restriction enzyme that produces informative fragments for each cross is a simple procedure, well known in the art. After separation by length in an appropriate matrix (e.g., agarose) and transfer to a membrane (e.g., nitrocellulose, nylon), the labeled probe is hybridized under conditions which result in equilibrium binding of the probe to the target followed by removal of excess probe by washing.

Nucleic acid probes to the marker loci can be cloned and/or synthesized. Detectable labels suitable for use with nucleic acid probes include any composition detectable by spectroscopic, radioisotopic, photochemical, biochemical, immunochemical, electrical, optical or chemical means. Useful labels include biotin for staining with labeled streptavidin conjugate, magnetic beads, fluorescent dyes, radiolabels, enzymes and colorimetric labels. Other labels include ligands which bind to antibodies labeled with fluorophores, chemiluminescent agents and enzymes. Labeling markers is readily achieved such as by the use of labeled PCR primers to marker loci.

The hybridized probe is then detected using, most typically, autoradiography or other similar detection technique (e.g., fluorography, liquid scintillation counter, etc.). Examples of specific hybridization protocols are widely available in the art, see, e.g., Berger, Sambrook, Ausubel, all supra.

Amplified variable sequences refer to amplified sequences of the plant genome which exhibit high nucleic acid residue variability between members of the same species. All organisms have variable genomic sequences and each organism (with the exception of a clone) has a different set of variable sequences. Once identified, the presence of specific variable sequence can be used to predict phenotypic traits. Preferably, DNA from the plant serves as a template for amplification with primers that flank a variable sequence of DNA. The variable sequence is amplified and then sequenced.

In vitro amplification techniques are well known in the art. Examples of techniques sufficient to direct persons of skill through such in vitro methods, including the polymerase chain reaction (PCR), the ligase chain reaction (LCR), Qβ-replicase amplification and other RNA polymerase mediated techniques (e.g., NASBA), are found in Berger, Sambrook and Ausubel (all supra) as well as Mullis, et al., (1987) U.S. Pat. No. 4,683,202; *PCR Protocols, A Guide to Methods and Applications* (Innis, et al., eds.) Academic Press Inc., San Diego Academic Press Inc. San Diego, Calif. (1990) (Innis); Arnheim and Levinson, (Oct. 1, 1990) *C&EN* 36-47; *The Journal Of NIH Research* (1991) 3:81-94; (Kwoh, et al., (1989) *Proc. Natl. Acad. Sci. USA* 86:1173; Guatelli, et al., (1990) *Proc. Natl. Acad. Sci. USA* 87:1874; Lomeli, et al., (1989) *J. Clin. Chem* 35:1826; Landegren, et al., (1988) *Science* 241:1077-1080; Van Brunt, (1990) *Biotechnology* 8:291-294; Wu and Wallace, (1989) *Gene* 4:560; Barringer, at al., (1990) *Gene* 89:117 and Sooknanan and Malek, (1995) *Biotechnology* 13:563-564. Improved methods of cloning in vitro amplified nucleic acids are described in Wallace, et al., U.S. Pat. No. 5,426,039. Improved methods of amplifying large nucleic acids by PCR are summarized in Cheng, et al., (1994) *Nature* 369:684, and the references therein, in which PCR amplicons of up to 40 kb are generated. One of skill will appreciate that essentially any RNA can be converted into a double stranded DNA suitable for restriction digestion, PCR expansion and sequencing using reverse transcriptase and a polymerase. See, Ausubel, Sambrook and Berger, all supra.

Oligonucleotides for use as primers, e.g., in amplification reactions and for use as nucleic acid sequence probes, are typically synthesized chemically according to the solid phase phosphoramidite triester method described by Beaucage and Caruthers, (1981) *Tetrahedron Lett.* 22:1859 or can simply be ordered commercially.

Alternatively, self-sustained sequence replication can be used to identify genetic markers. Self-sustained sequence replication refers to a method of nucleic acid amplification using target nucleic acid sequences which are replicated exponentially in vitro under substantially isothermal conditions by using three enzymatic activities involved in retroviral replication: (1) reverse transcriptase, (2) Rnase H and (3) a DNA-dependent RNA polymerase (Guatelli, et al., (1990) *Proc Natl Acad Sci USA* 87:1874). By mimicking the retroviral strategy of RNA replication by means of cDNA intermediates, this reaction accumulates cDNA and RNA copies of the original target As mentioned above, there are many different types of molecular markers, including amplified fragment length polymorphisms (AFLP), allele-specific hybridization (ASH), single nucleotide polymorphisms (SNP), simple sequence repeats (SSR) and isozyme markers. Methods of using the different types of molecular markers are known to those skilled in the art. The markers of the present invention include simple sequence repeats and single nucleotide polymorphisms.

SSR data is generated by hybridizing primers to conserved regions of the plant genome which flank the SSR sequence. PCR is then used to amplify the repeats between the primers. The amplified sequences are then electrophoresed to determine the size and therefore the di-, tri and tetra nucleotide repeats.

Dinucleotide repeats have been found in higher plants (Condit and Hubbell, (1991) *Genome* 34:66). Dinucleotide repeats have been reported to occur in the human genome as many as 50,000 times with n varying from 10 to 60 or more (Jacob, et al., (1991) *Cell* 67:213.

Mapping of Marker LOCI

Multiple experimental paradigms have been developed to identify and analyze molecular markers. In general, these paradigms involve crossing one or more parental pairs, which can be, for example, a single pair derived from two inbred strains or multiple related or unrelated parents of different inbred strains or lines, which each exhibit different characteristics relative to the phenotypic trait of interest. The parents and a population of progeny are genotyped, typically for marker loci and evaluated for the trait of interest. In the context of the present invention, the parental and progeny plants are genotyped for any one or more of the molecular markers: TS304T, TS050, the sPPR genes identified below or homologues or alternative markers linked to any one or more of TS304T, TS050 and the SPPR genes and evaluated for ability to restore fertility. Markers associated with fertility restoration are identified based on the significant statistical correlations between the marker genotype(s) and the restoration phenotype of the evaluated progeny plants. Numerous methods for determining whether markers are genetically linked to the gene associated with fertility restoration are known to those of skill in the art and include, e.g., interval mapping (Lander and Botstein, (1989) *Genetics* 121:185), regression mapping (Haley and Knott, (1992) *Heredity* 69:315) or MQM mapping (Jansen, (1994) *Genetics* 138: 871). In addition, the following references provide guidance: Van Ooijen and Voorrips, (2001) "JoinMap® 3.0, Software for the calculation of genetic linkage maps", *Plant Research International*, Wageningen, the Netherlands.

Marker Assisted Selection and Breeding of Plants

A primary motivation for development of molecular markers in crop species is the potential for increased efficiency in plant breeding through marker assisted selection (MAS). Genetic marker alleles, or alternatively, identified QTL alleles, are used to identify plants that contain a desired genotype at one or more loci and that are expected to transfer the desired genotype, along with a desired phenotype to their progeny. Genetic marker alleles can be used to identify plants that contain a desired genotype at one locus or at several unlinked or linked loci (e.g., a haplotype) and that would be expected to transfer the desired genotype, along with a desired phenotype to their progeny. The present invention provides the means to identify plants, particularly monocots, e.g., *sorghum*, that are able to restore fertility to *Sorghum* cms plants by identifying plants having a specified allele, e.g., at one or more of markers TS304T, TS050, the sPPR genes and homologous or linked markers. Similarly, by identifying plants lacking the desired allele, non-restorer plants can be identified and, e.g., eliminated from subsequent crosses. It will be appreciated that for the purposes of MAS, the term marker can encompass both marker and sPPR genes as they all can be used to identify plants capable of fertility restoration.

After a desired phenotype, e.g., fertility restoration and a polymorphic chromosomal locus, e.g., a marker locus or QTL, are determined to segregate together, it is possible to use those polymorphic loci to select for alleles corresponding to the desired phenotype: a process called marker-assisted selection (MAS). In brief, a nucleic acid corresponding to the marker nucleic acid is detected in a biological sample from a plant to be selected. This detection can take the form of hybridization of a probe nucleic acid to a marker, e.g., using allele-specific hybridization, Southern analysis, northern analysis, in situ hybridization, hybridization of primers followed by PCR amplification of a region of the marker or the like. A variety of procedures for detecting markers are described herein, e.g., in the section entitled "*DETECTION OF MARKER LOCI*." After the presence (or absence) of a particular marker and/or marker allele in the biological sample is verified, the plant is selected, i.e., used to make progeny plants by selective breeding.

*Sorghum* breeders need to combine fertility restoration with genes for high yield and other desirable traits to develop improved *sorghum* varieties. Fertility restoration screening for large numbers of plants can be expensive, time consuming and unreliable. Use of the polymorphic loci described herein, and genetically-linked nucleic acids, as genetic markers for the fertility restoration locus is an effective method for selecting varieties capable of fertility restoration in breeding programs. For example, one advantage of marker-assisted selection over field evaluations for fertility restoration is that MAS can be done at any time of year regardless of the growing season. Moreover, environmental effects are irrelevant to marker-assisted selection.

When a population is segregating for multiple loci affecting one or multiple traits, e.g., multiple loci involved in fertility restoration or multiple loci each involved in fertility restoration of different cms systems or loci affecting distinct traits. (for example fertility and disease resistance) the efficiency of MAS compared to phenotypic screening becomes even greater because all the loci can be processed in the lab together from a single sample of DNA. Any one or more of the markers and/or marker alleles, e.g., two or more, up to and including all of the established markers, can be assayed simultaneously.

Another use of MAS in plant breeding is to assist the recovery of the recurrent parent genotype by backcross breeding. Backcross breeding is the process of crossing a progeny back to one of its parents. Backcrossing is usually done for the purpose of introgressing one or a few loci from a donor parent into an otherwise desirable genetic background from the recurrent parent. The more cycles of backcrossing that are done, the greater the genetic contribution of the recurrent parent to the resulting variety. This is often necessary, because donor parent plants may be otherwise undesirable, i.e., due to low yield, low fecundity or the like. In contrast, varieties which are the result of intensive breeding programs may have excellent yield, fecundity or the like, merely being deficient in one desired trait such as fertility restoration. As a skilled worker understands, backcrossing can be done to select for or against a trait. For example, in the present invention, one can select a restorer gene for breeding a restorer line or one select against a restorer gene for breeding a maintainer (female pool).

The presence and/or absence of a particular genetic marker allele, e.g., TS304T, TS050, sPPR genes or a homolog thereof, in the genome of a plant exhibiting a preferred phenotypic trait is determined by any method listed above, e.g., RFLP, AFLP, SSR, etc. If the nucleic acids from the plant are positive for a desired genetic marker, the plant can be selfed to create a true breeding line with the same genotype or it can be crossed with a plant with the same marker or with other desired characteristics to create a sexually crossed hybrid generation.

Positional Cloning

The molecular markers of the present invention, for example, TS304T, TS050 and the PPR genes, for example, sPPR1, etc., and nucleic acids homologous thereto, can be used, as indicated previously, to identify additional linked marker loci, which can be cloned by well established procedures, e.g., as described in detail in Ausubel, Berger and Sambrook, supra. Similarly, these markers and genes as well as any additionally identified linked molecular markers can be used to physically isolate, e.g., by cloning, nucleic acids associated with markers contributing to fertility restoration. Such nucleic acids, i.e., linked to the marker, have a variety of uses, including as genetic markers for identification of additional markers in subsequent applications of marker assisted selection (MAS). Such nucleic acids may also include a restorer gene itself.

These nucleic acids are first identified by their genetic linkage to markers of the present invention. Isolation of the nucleic acid of interest is achieved by any number of methods as discussed in detail in such references as Ausubel, Berger and Sambrook, supra, and Clark, Ed. (1997) *Plant Molecular Biology: A Laboratory Manual* Springer-Verlag, Berlin.

For example, "Positional gene cloning" uses the proximity of a genetic marker to physically define an isolated chromosomal fragment that is linked to a gene. The isolated chromosomal fragment can be produced by such well known methods as digesting chromosomal DNA with one or more restriction enzymes or by amplifying a chromosomal region in a polymerase chain reaction (PCR) or alternative amplification reaction. The digested or amplified fragment is typically ligated into a vector suitable for replication, e.g., a plasmid, a cosmid, a phage, an artificial chromosome, or the like and optionally expression, of the inserted fragment. Markers which are adjacent to an open reading frame (ORF) associated with a phenotypic trait can hybridize to a DNA clone, thereby identifying a clone on which an ORF is located. If the marker is more distant, a fragment containing the open reading frame is identified by successive rounds of screening and isolation of clones which together comprise a contiguous sequence of DNA, a "contig." Protocols sufficient to guide one of skill through the isolation of clones associated with linked markers are found in, e.g. Berger, Sambrook and Ausubel, all supra.

Isolated Chromosome Region and Isolated Restorer Gene

The present invention provides the chromosome region comprising sequences associated with a gene involved in fertility restoration. The gene is localized in the region defined by two markers of the present invention (TS050 and TS304T) wherein each marker is genetically linked to the gene. Such regions can be utilized to identify homologous nucleic acids and/or can be used in the production of transgenic plants having the fertility restoration conferred by the introduced gene. A chromosome region comprising a gene is isolated, e.g., cloned via positional cloning methods outlined above. A chromosome region can contain one or more ORFs associated with fertility restoration, and can be cloned on one or more individual vectors, e.g., depending on the size of the chromosome region. For example, in the present invention four genes comprising the PPR motif were identified within the interval flanked by SSR markers TS050 and TS304T and one PPR gene was identified just outside the interval flanked by the SSR markers TS050 and TS304T.

It will be appreciated that numerous vectors are available in the art for the isolation and replication of the nucleic acids of the invention. For example, plasmids, cosmids and phage vectors are well known in the art and are sufficient for many applications (e.g., in applications involving insertion of nucleic acids ranging from less than 1 to about 20 kilobases (kb). In certain applications, it is advantageous to make or clone large nucleic acids to identify nucleic acids more distantly linked to a given marker, or to isolate nucleic acids in excess of 10-20 kb, e.g., up to several hundred kilobases or more, such as the entire interval between two linked markers, i.e., up to and including one or more centiMorgans (cM), linked to genes and QTLs as identified herein. In such cases, a number of vectors capable of accommodating large nucleic acids are available in the art, these include, yeast artificial chromosomes (YACs), bacterial artificial chromosomes (BACs), plant artificial chromosomes (PACs), mammalian artificial chromosomes (MACs) and the like. For a general introduction to YACs, BACs, PACs and MACs as artificial chromosomes, see, e.g., Monaco and Larin, (1994) *Trends Biotechnol* 12:280. In addition, methods for the in vitro amplification of large nucleic acids linked to genetic markers are widely available (e.g., Cheng, at al., (1994) *Nature* 369: 684, and references therein). Cloning systems can be created or obtained commercially; see, for example, Stratagene Cloning Systems, Catalogs 2000 (La Jolla, Calif.).

Generation of Transgenic Plants and Cells

The present invention also relates to host cells and organisms which are transformed with nucleic acids corresponding to fertility restoration gene and other genes identified according to the invention. For example, such nucleic acids include chromosome intervals, ORFs and/or cDNAs corresponding to a sequence or subsequence included within the identified chromosome interval or ORF. Additionally, the invention provides for the production of polypeptides corresponding to the fertility restorer gene by recombinant techniques. Host cells are genetically engineered (i.e., transduced, transfected or transformed) with the vectors of this invention (i.e., vectors which comprise the nucleic acids identified according to the methods of the invention and as described above) which are, for example, a cloning vector or an expression vector. Such vectors include, in addition to those described above, e.g., an *agrobacterium*, a virus (such as a plant virus), a naked polynucleotide or a conjugated polynucleotide. The vectors are introduced into plant tissues, cultured plant cells or plant protoplasts by a variety of standard methods including electroporation (From, at al., (1985) *Proc. Natl. Acad. Sci. USA* 82:5824), infection by viral vectors such as cauliflower mosaic virus (CaMV) (Hohn, at al., (1982) *Molecular Biology of Plant Tumors* (Academic Press, New York, pp. 549-560; Howell, U.S. Pat. No. 4,407,956), high velocity ballistic penetration by small particles with the nucleic acid either within the matrix of small beads or particles or on the surface (Klein, at al., (1987) *Nature* 327:70), use of pollen as vector (WO 85/01856) or use of *Agrobacterium tumefaciens* or *A. rhizogenes* carrying a T-DNA plasmid in which DNA fragments are cloned. The T-DNA plasmid is transmitted to plant cells upon infection by *Agrobacterium tumefaciens* and a portion is stably integrated into the plant genome (Horsch, at al., (1984) *Science* 233:496; Fraley, et al., (1983) *Proc. Natl. Acad. Sci. USA* 80:4803). The method of introducing a nucleic acid of the present invention into a host cell is not critical to the instant invention. Thus, any method, e.g., including but not limited to the above examples, which provides for effective introduction of a nucleic acid into a cell or protoplast can be employed.

The engineered host cells can be cultured in conventional nutrient media modified as appropriate for such activities as, for example, activating promoters or selecting transformants. These cells can optionally be cultured into transgenic plants. Plant regeneration from cultured protoplasts is described in Evans, et al., (1983) *Handbook of Plant Cell Cultures* 1:124-176 (MacMillan Publishing Co., New York); Davey, (1983) *Protoplasts*, pp. 12-29 (Birkhauser, Basel); Dale, (1983) *Protoplasts* pp. 31-41, (Birkhauser, Basel); Binding, (1985) *Plant Protoplasts* pp. 21-73, (CRC Press, Boca Raton).

The present invention also relates to the production of transgenic organisms, which may be bacteria, yeast, fungi or plants, transduced with the nucleic acids, e.g., cloned fertility restoration gene of the invention. A thorough discussion of techniques relevant to bacteria, unicellular eukaryotes and cell culture may be found in references enumerated above and are briefly outlined as follows. Several well-known methods of introducing target nucleic acids into bacterial cells are available, any of which may be used in the present invention. These include: fusion of the recipient cells with bacterial protoplasts containing the DNA, treatment of the cells with liposomes containing the DNA, electroporation, projectile bombardment (biolistics), carbon fiber delivery and infection with viral vectors (discussed further, below), etc. Bacterial cells can be used to amplify the number of plasmids containing DNA constructs of this invention. The bacteria are grown to log phase and the plasmids within the bacteria can be isolated by a variety of methods known in the art (see, for instance, Sambrook). In addition, a plethora of kits are commercially available for the purification of plasmids from bacteria. For their proper use, follow the manufacturer's instructions (see, for example, EasyPrep™, FlexiPrep™, both from Pharmacia Biotech; StrataClean™, from Stratagene; and, QIAprep™ from Qiagen). The isolated and purified plasmids are then further manipulated to produce other plasmids, used to transfect plant cells or incorporated into *Agrobacterium tumefaciens* related vectors to infect plants. Typical vectors contain transcription and translation terminators, transcription and translation initiation sequences and promoters useful for regulation of the expression of the particular target nucleic acid. The vectors optionally comprise generic expression cassettes containing at least one independent terminator sequence, sequences permitting replication of the cassette in eukaryotes or prokaryotes or both, (e.g., shuttle vectors) and selection markers for both prokaryotic and eukaryotic systems. Vectors are suitable for replication and integration in prokaryotes, eukaryotes or preferably both. See, Giliman and Smith, (1979) *Gene* 8:81; Roberts, et al., (1987) *Nature* 328:731; Schneider, et al., (1995) *Protein Expr. Purif.* 6435:10; Ausubel, Sambrook, Berger (all supra). A catalogue of Bacteria and Bacteriophages useful for cloning is provided, e.g., by the ATCC, e.g., *The ATCC Catalogue of Bacteria and Bacteriophage* (1992) Gherna, et al., (eds) published by the ATCC. Additional basic procedures for sequencing, cloning and other aspects of molecular biology and underlying theoretical considerations are also found in Watson, et al., (1992) *Recombinant DNA* Second Edition, Scientific American Books, N.Y.

Transforming Nucleic Acids into Plants

Embodiments of the present invention pertain to the production of transgenic plants comprising the cloned nucleic acids, e.g., chromosome intervals, isolated ORFs and cDNAs associated with fertility restoration gene of the invention. Techniques for transforming plant cells with nucleic acids are generally available and can be adapted to the invention by the use of nucleic acids encoding or corresponding to the fertility restoration gene, homologs thereof, isolated chromosome intervals, and the like. In addition to Berger, Ausubel and Sambrook, useful general references for plant cell cloning, culture and regeneration include Jones, (ed) (1995) *Plant Gene Transfer and Expression Protocols—Methods in Molecular Biology*, Volume 49 Humana Press Towata N.J.; Payne, et al., (1992) *Plant Cell and Tissue Culture in Liquid Systems* John Wiley & Sons, Inc. New York, N.Y. (Payne) and Gamborg and Phillips, (eds) (1995) *Plant Cell, Tissue and Organ Culture; Fundamental Methods* Springer Lab Manual, Springer-Verlag (Berlin Heidelberg New York) (Gamborg). A variety of cell culture media are described in Atlas and Parks, (eds) *The Handbook of Microbiological Media* (1993) CRC Press, Boca Raton, Fla. (Atlas). Additional information for plant cell culture is found in available commercial literature such as the *Life Science Research Cell Culture Catalogue* (1998) from Sigma-Aldrich, Inc (St Louis, Mo.) (Sigma-LSRCCC) and e.g., the *Plant Culture Catalogue* and supplement (1997) also from Sigma-Aldrich, Inc (St Louis, Mo.) (Sigma-PCCS). Additional details regarding plant cell culture are found in Croy, (ed.) (1993) *Plant Molecular Biology* Bios Scientific Publishers, Oxford, U.K.

The nucleic acid constructs of the invention, e.g., plasmids, cosmids, artificial chromosomes, DNA and RNA polynucleotides, are introduced into plant cells, either in culture or in the organs of a plant by a variety of conventional techniques. Where the sequence is expressed, the sequence is optionally combined with transcriptional and translational initiation regulatory sequences which direct the transcription or translation of the sequence from the exogenous DNA in the intended tissues of the transformed plant.

Isolated nucleic acid acids of the present invention can be introduced into plants according to any of a variety of techniques known in the art. Techniques for transforming a wide variety of higher plant species are well known and described in the technical, scientific, and patent literature. See, for example, Weising, et at, (1988) *Ann. Rev. Genet.* 22:421-477.

The DNA constructs of the invention, for example plasmids, cosmids, phage, naked or variously conjugated-DNA polynucleotides, (e.g., polylysine-conjugated DNA, peptide-conjugated DNA, liposome-conjugated DNA, etc.) or artificial chromosomes, can be introduced directly into the genomic DNA of the plant cell using techniques such as electroporation and microinjection of plant cell protoplasts or the DNA constructs can be introduced directly to plant cells using ballistic methods, such as DNA particle bombardment.

Microinjection techniques for injecting e.g., cells, embryos, callus and protoplasts, are known in the art and well described in the scientific and patent literature. For example, a number of methods are described in Jones, (ed) (1995) *Plant Gene Transfer and Expression Protocols—Methods in Molecular Biology* Volume 49 Humana Press Towata N.J., as well as in the other references noted herein and available in the literature.

For example, the introduction of DNA constructs using polyethylene glycol precipitation is described in Paszkowski, et at, (1984) *EMBO J.* 3:2717. Electroporation techniques are described in Fromm, et al., (1985) *Proc. Nat'l. Acad. Sci. USA* 82:5824. Ballistic transformation techniques are described in Klein, et al., (1987) *Nature* 327:70-73. Additional details are found in Jones, (1995) and Gamborg and Phillips, (1995), supra and in U.S. Pat. No. 5,990,387.

Alternatively, and in some cases preferably, *Agrobacterium* mediated transformation is employed to generate transgenic plants. *Agrobacterium*-mediated transformation techniques, including disarming and use of binary vectors, are also well described in the scientific literature. See, for example Horsch, et al., (1984) *Science* 233:496 and Fraley, et al., (1984) *Proc. Nat'l. Acad. Sci. USA* 80:4803 and recently reviewed in Hansen and Chilton, (1998) *Current Topics in Microbiology* 240:22 and Das, (1998) *Subcellular Biochemistry* 29: *Plant Microbe Interactions* pp 343-363.

The DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. See, U.S. Pat. No. 5,591,616. Although *Agrobacterium* is useful primarily in dicots, certain monocots can be transformed by *Agrobacterium*. For instance, *Agrobacterium* transformation of maize is described in U.S. Pat. No. 5,550,318.

Other methods of transfection or transformation include (1) *Agrobacterium rhizogenes*-mediated transformation (see, e.g., Lichtenstein and Fuller, (1987) In: *Genetic Engineering*, vol. 6, P W J Rigby, Ed., London, Academic Press and Lichtenstein and Draper (1985) In: DNA Cloning, Vol. II, Glover, Ed., Oxford, IRI Press; WO 88/02405, published Apr. 7, 1988, describes the use of *A. rhizogenes* strain A4 and its Ri plasmid along with *A. tumefaciens* vectors pARCB or pARC16 (2) liposome-mediated DNA uptake (see, e.g., Freeman, et at, (1984) *Plant Cell Physiol.* 25:1353), (3) the vortexing method (see, e.g., Kindle, (1990) *Proc. Natl. Acad. Sci., (USA)* 87:1228.

DNA can also be introduced into plants by direct DNA transfer into pollen as described by Zhou, et al., (1983) *Methods in Enzymology* 101:433; Hess, (1987) *Intern Rev. Cytol.* 107:367; Luo, et al., (1988) *Plant Mol. Biol. Reporter* 6:165. Expression of polypeptide coding genes can be obtained by injection of the DNA into reproductive organs of a plant as described by Pena, et al., (1987) *Nature* 325:274. DNA can also be injected directly into the cells of immature embryos and the desiccated embryos rehydrated as described by Neuhaus, et al., (1987) *Theor. Appl. Genet.* 75:30 and Benbrook, at al., (1986) in *Proceedings Bio Expo* Butterworth, Stoneham, Mass., pp. 27-54. A variety of plant viruses that can be employed as vectors are known in the art and include cauliflower mosaic virus (CaMV), geminivirus, brome mosaic virus and tobacco mosaic virus.

Regeneration of Transgenic Plants

Transformed plant cells which are derived by any of the above transformation techniques can be cultured to regenerate a whole plant which possesses the transformed genotype and thus the desired phenotype. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans, at al., (1983) *Protoplasts Isolation and Culture, Handbook of Plant Cell Culture* pp. 124-176, Macmillian Publishing Company, New York and Binding, (1985) *Regeneration of Plants, Plant Protoplasts* pp. 21-73, CRC Press, Boca Raton. Regeneration can also be obtained from plant callus, explants, somatic embryos (Dandekar, et al., (1989) *J. Tissue Cult. Meth.* 12:145; McGranahan, et al., (1990) *Plant Cell Rep.* 8:512) organs or parts thereof. Such regeneration techniques are described generally in Klee, et al., (1987) *Ann. Rev. of Plant Phys.* 38:467-486. Additional details are found in Payne, (1992) and Jones, (1995) both supra and Weissbach and Weissbach, eds. (1988) *Methods for Plant Molecular Biology* Academic Press, Inc., San Diego, Calif. This regeneration and growth process includes the steps of selection of transformant cells and shoots, rooting the transformant shoots and growth of the plantlets in soil. These methods are adapted to the invention to produce transgenic plants bearing QTLs and other genes isolated according to the methods of the invention.

In addition, the regeneration of plants containing the polynucleotide of the present invention and introduced by *Agrobacterium* into cells of leaf explants can be achieved as described by Horsch, et al., (1985) *Science* 227:1229-1231. In this procedure, transformants are grown in the presence of a selection agent and in a medium that induces the regeneration of shoots in the plant species being transformed as described by Fraley, et al., (1983) *Proc. Natl. Acad. Sci. (U.S.A.)* 80:4803. This procedure typically produces shoots within two to four weeks and these transformant shoots are then transferred to an appropriate root-inducing medium containing the selective agent and an antibiotic to prevent bacterial growth. Transgenic plants of the present invention may be fertile or sterile.

Preferred plants for the transformation and expression of the fertility restoration gene and other nucleic acids identified and cloned according to the present invention include agronomically and horticulturally important species. Such species include primarily monocots, for example, but not limited to *sorghum*, maize, rice and millet.

In construction of recombinant expression cassettes of the invention, which include, for example, helper plasmids comprising virulence functions and plasmids or viruses comprising exogenous DNA sequences such as structural genes, a plant promoter fragment is optionally employed which directs expression of a nucleic acid in any or all tissues of a regenerated plant. Examples of constitutive promoters include the cauliflower mosaic virus (CaMV) 35S transcription initiation region, the 1'- or 2'-promoter derived from T-DNA of *Agrobacterium tumefaciens* and other transcription initiation regions from various plant genes known to those of skill. Alternatively, the plant promoter may direct expression of the polynucleotide of the invention exclusively or preferentially in a specific tissue (tissue-specific or tissue-preferred promoters) or may be otherwise under more precise environmental control (inducible promoters). Examples of tissue-specific promoters under developmental control include promoters that initiate transcription only in certain tissues, such as fruit, seeds or flowers.

Any of a number of promoters which direct transcription in plant cells can be suitable. The promoter can be either constitutive or inducible. In addition to the promoters noted above, promoters of bacterial origin which operate in plants include the octopine synthase promoter, the nopaline synthase promoter and other promoters derived from native Ti plasmids. See, Herrara-Estrella, of al., (1983) *Nature* 303:209. Viral promoters include the 35S and 19S RNA promoters of cauliflower mosaic virus. See, Odell, et al., (1985) *Nature* 313:810. Other plant promoters include the ribulose-1,3-bisphosphate carboxylase small subunit promoter and the phaseolin promoter. The promoter sequence from the E8 gene and other genes may also be used. The isolation and sequence of the E8 promoter is described in detail in Deikman and Fischer, (1988) *EMBO J.* 7:3315. Many other promoters are in current use and can be coupled to an exogenous DNA sequence to direct expression of the nucleic acid. For example, to direct expression in male reproductive tissues, an early microspore development or tapetum expressed promoter, among others, may be used.

If expression of a polypeptide, including those encoded by the fertility restoration locus or other nucleic acids correlating with phenotypic traits of the present invention, is desired, a polyadenylation region at the 3'-end of the coding region is typically included. The polyadenylation region can be derived from the natural gene, from a variety of other plant genes or from, e.g., T-DNA.

The vector comprising the sequences (e.g., promoters or coding regions) from genes encoding expression products and transgenes of the invention will typically include a nucleic acid subsequence, a marker gene which confers a selectable or alternatively, a screenable, phenotype on plant cells. For example, the marker may encode biocide tolerance, particularly antibiotic tolerance, such as tolerance to kanamycin, G418, bleomycin, hygromycin or herbicide tolerance, such as tolerance to chlorosluforon or phosphinothricin (the active ingredient in the herbicides bialaphos or Basta). See, e.g., Padgette, et al., (1996) *Herbicide-Resistant Crops* (Duke, ed.), pp 53-84, CRC Lewis Publishers, Boca Raton ("Padgette, 1996"). For example, crop selectivity to specific herbicides can be conferred by engineering into crops genes which encode appropriate herbicide metabolizing enzymes from other organisms, such as microbes. See, Vasil, (1996) Herbicide-Resistant Crops (Duke, ed.), pp 85-91, CRC Lewis Publishers, Boca Raton) ("Vasil, 1996").

One of skill will recognize that after the recombinant expression cassette is stably incorporated in transgenic plants and confirmed to be operable, it can be introduced into other plants by sexual crossing. Any of a number of standard breeding techniques can be used, depending upon the species to be crossed. In vegetatively propagated crops, mature transgenic plants can be propagated by the taking of cuttings or by tissue culture techniques to produce multiple identical plants. Selection of desirable transgenics is made and new varieties are obtained and propagated vegetatively for commercial use. In seed propagated crops, mature transgenic plants can be self pollinated to produce a homozygous inbred plant. The inbred plant produces seed containing the newly introduced heterologous nucleic acid. These seeds can be grown to produce plants that would produce the selected phenotype. Parts obtained from the regenerated plant, such as flowers, seeds, leaves, branches, fruit and the like are included in the invention, provided that these parts comprise cells comprising the isolated nucleic acid of the present invention. Progeny and variants, and mutants of the regenerated plants are also included within the scope of the invention, provided that these parts comprise the introduced nucleic acid sequences.

Transgenic plants expressing a polynucleotide of the present invention can be screened for transmission of the nucleic acid of the present invention by, for example, standard immunoblot and DNA detection techniques. Expression at the RNA level can be determined initially to identify and quantitative expression-positive plants. Standard techniques for RNA analysis can be employed and include PCR amplification assays using oligonucleotide primers designed to amplify only the heterologous RNA templates and solution hybridization assays using heterologous nucleic acid-specific probes. The RNA-positive plants can then be analyzed for protein expression by Western immunoblot analysis using the specifically reactive antibodies of the present invention. In addition, in situ hybridization and immunocytochemistry according to standard protocols can be done using heterologous nucleic acid specific polynucleotide probes and antibodies, respectively, to localize sites of expression within transgenic tissue. Generally, a number of transgenic lines are usually screened for the incorporated nucleic acid to identify and select plants with the most appropriate expression profiles.

A preferred embodiment is a transgenic plant that is homozygous for the added heterologous nucleic acid; i.e., a transgenic plant that contains two added nucleic acid sequences, one gene at the same locus on each chromosome of a chromosome pair. A homozygous transgenic plant can be obtained by sexually mating (selfing) a heterozygous transgenic plant that contains a single added heterologous nucleic acid, germinating some of the seed produced and analyzing the resulting plants produced for altered expression of a polynucleotide of the present invention relative to a control plant (i.e., native, non-transgenic). Back-crossing to a parental plant and out-crossing with a non-transgenic plant are also contemplated.

High Throughput Screening

In one aspect of the invention, the determination of genetic marker alleles is performed by high throughput screening. High throughput screening involves providing a library of genetic markers, e.g., RFLPs, AFLPs, isozymes, specific alleles and variable sequences, including SSRs and SNPs. Such libraries are then screened against plant genomes to generate a "fingerprint" for each plant under consideration. In some cases a partial fingerprint comprising a sub-portion of the markers is generated in an area of interest. Once the genetic marker alleles of a plant have been identified, the correspondence between one or several of the marker alleles and a desired phenotypic trait is determined through statistical associations based on the methods of this invention.

High throughput screening can be performed in many different formats. Hybridization can take place in a 96-, 384- or a 1536-well format or in a matrix on a silicon chip or other format.

In one commonly used format, a dot blot apparatus is used to deposit samples of fragmented and denatured genomic DNA on a nylon or nitrocellulose membrane. After cross-linking the nucleic acid to the membrane, either through exposure to ultra-violet light or by heat, the membrane is incubated with a labeled hybridization probe. The labels are incorporated into the nucleic acid probes by any of a number of means well-known in the art. The membranes are washed to remove non-hybridized probes and the association of the label with the target nucleic acid sequence is determined.

A number of well-known robotic systems have been developed for high throughput screening, particularly in a 96 well format. These systems include automated workstations like the automated synthesis apparatus developed by Takeda Chemical Industries, LTD. (Osaka, Japan) and many robotic systems utilizing robotic arms (Zymate II, Zymark Corporation, Hopkinton, Mass.; ORCA™, Beckman Coulter, Fullerton Calif.). Any of the above devices are suitable for use with the present invention. The nature and implementation of modifications to these devices (if any) so that they can operate as discussed herein will be apparent to persons skilled in the relevant art.

In addition, high throughput screening systems themselves are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate entire procedures including all sample and reagent pipetting, liquid dispensing, timed incubations and final readings of the microplate or membrane in detector(s) appropriate for the assay. These configurable systems provide high throughput and rapid start up as well as a high degree of flexibility and customization. The manufacturers of such systems provide detailed protocols for the use of their products in high throughput applications.

In one variation of the invention, solid phase arrays are adapted for the rapid and specific detection of multiple polymorphic nucleotides. Typically, a nucleic acid probe is linked to a solid support and a target nucleic acid is hybridized to the probe. Either the probe, or the target, or both, can be labeled, typically with a fluorophore. If the target is labeled, hybridization is evaluated by detecting bound fluorescence. If the probe is labeled, hybridization is typically detected by quenching of the label by the bound nucleic acid. If both the probe and the target are labeled, detection of hybridization is typically performed by monitoring a color shift resulting from proximity of the two bound labels.

In one embodiment, an array of probes are synthesized on a solid support. Using chip masking technologies and photoprotective chemistry, it is possible to generate ordered arrays of nucleic acid probes. These arrays, which are known, e.g., as "DNA chips" or as very large scale immobilized polymer synthesis arrays (VLSIPS™ arrays) can include millions of defined probe regions on a substrate having an area of about 1 cm$^2$ to several cm$^2$.

In another embodiment, capillary electrophoresis is used to analyze polymorphism. This technique works best when the polymorphism is based on size, for example, AFLP and SSR. This technique is described in detail in U.S. Pat. Nos. 5,534,123 and 5,728,282. Briefly, capillary electrophoresis tubes are filled with the separation matrix. The separation matrix contains hydroxyethyl cellulose, urea and optionally formamide. The AFLP or SSR samples are loaded onto the capillary tube and electorphoresed. Because of the small amount of sample and separation matrix required by capillary electrophoresis, the run times are very short. The molecular sizes and therefore, the number of nucleotides present in the nucleic acid sample is determined by techniques described herein. In a high throughput format, many capillary tubes are placed in a capillary electrophoresis apparatus. The samples are loaded onto the tubes and electrophoresis of the samples is run simultaneously. See, Mathies and Huang, (1992) Nature 359:167.

Integrated Systems

Because of the great number of possible combinations present in one array, in one aspect of the invention, an integrated system such as a computer, software corresponding to the statistical models of the invention and data sets corresponding to genetic markers and phenotypic values, facilitates mapping of phenotypic traits, including genes and QTLs. The phrase "integrated system" in the context of this invention refers to a system in which data entering a computer corresponds to physical objects or processes external to the computer, e.g., nucleic acid sequence hybridization and a process that, within a computer, causes a physical transformation of the input signals to different output signals. In other words, the input data, e.g., hybridization on a specific region of an array is transformed to output data, e.g., the identification of the sequence hybridized. The process within the computer is a set of instructions, or "program," by which positive hybridization signals are recognized by the integrated system and attributed to individual samples as a genotype. Additional programs correlate the genotype, and more particularly in the methods of the invention, the haplotype, of individual samples with phenotypic values, e.g., using the HAPLO-IM$^+$, HAPLO-MQM, and/or HAPLO-MQM$^+$ models of the invention. For example, the programs JoinMap® and MapQTL® are particularly suited to this type of analysis and can be extended to include the HAPLO-IM$^+$, HAPLO-MQM, and/or HAPLO-MQM$^+$ models of the invention. In addition there are numerous e.g., C/C++ programs for computing, Delphi and/or Java programs for GUI interfaces and Active X applications (e.g., Olectra Chart and True WevChart) for charting tools. Other useful software tools in the context of the integrated systems of the invention include statistical packages such as SAS, Genstat, and S-Plus. Furthermore additional programming languages such as Fortran and the like are also suitably employed in the integrated systems of the invention.

In one aspect, the invention provides an integrated system comprising a computer or computer readable medium comprising a database with at least one data set that corresponds to genotypes for genetic markers. The system also includes a user interface allowing a user to selectively view one or more databases. In addition, standard text manipulation software such as word processing software (e.g., Microsoft Word™ or Corel Wordperfect™) and database or spreadsheet software (e.g., spreadsheet software such as Microsoft Excel™, Corel Quattro Prom™, or database programs such as Microsoft Access™ or Paradox™) can be used in conjunction with a user interface (e.g., a GUI in a standard operating system such as a Windows, Macintosh or Linux system) to manipulate strings of characters.

The invention also provides integrated systems for sample manipulation incorporating robotic devices as previously described. A robotic liquid control armature for transferring solutions (e.g., plant cell extracts) from a source to a destination, e.g., from a microtiter plate to an array substrate, is optionally operably linked to the digital computer (or to an additional computer in the integrated system). An input device for entering data to the digital computer to control high throughput liquid transfer by the robotic liquid control armature and, optionally, to control transfer by the armature to the solid support, is commonly a feature of the integrated system.

Integrated systems for genetic marker analysis of the present invention typically include a digital computer with one or more of high-throughput liquid control software, image analysis software, data interpretation software, a robotic liquid control armature for transferring solutions from a source to a destination operably linked to the digital computer, an input device (e.g., a computer keyboard) for entering data to the digital computer to control high throughput liquid transfer by the robotic liquid control armature and, optionally, an image scanner for digitizing label signals from labeled probes hybridized, e.g., to expression products on a solid support operably linked to the digital computer. The image scanner interfaces with the image analysis software to provide a measurement of, e.g., differentiating nucleic acid probe label intensity upon hybridization to an arrayed sample nucleic acid population, where the probe label intensity measurement is interpreted by the data interpretation software to show whether, and to what degree, the labeled probe hybridizes to an arrayed sample DNA. The data so derived are then correlated with phenotypic values using the statistical models of the present invention, to determine the correspondence between phenotype and genotype(s) for genetic markers, thereby, assigning chromosomal locations.

Optical images, e.g., hybridization patterns viewed (and, optionally, recorded) by a camera or other recording device (e.g., a photodiode and data storage device) are optionally further processed in any of the embodiments herein, e.g., by digitizing the image and/or storing and analyzing the image on a computer. A variety of commercially available peripheral equipment and software is available for digitizing, storing and analyzing a digitized video or digitized optical image, e.g., using PC (Intel x86 or pentium chip-compatible DOS™, OS2™ WINDOWS™, WINDOWS NT™ or WINDOWS95™ based machines), MACINTOSH™, LINUX or UNIX based (e.g., SUN™ work station) computers.

Kits

Kits are also provided to facilitate the screening of germplasm for the markers of the present invention. The kits comprise the polynucleotides of the present invention, fragments or complements thereof, for use as probes or primers to detect the markers for a restorer gene. Instructions for using the polynucleotides, as well as buffers and/or other solutions may also be provided to facilitate the use of the polynucleotides. The kit is useful for high throughput screening and in particular, high throughout screening with integrated systems.

EXAMPLES

In a typical *sorghum* breeding program, testcrosses with female lines are used in order to select plants carrying the homozygous or heterozygous restorer allele. In this typical method, an additional season is required to select plants carrying a restorer gene. Significant labor and field resources are required for making testcrosses and for growing out progeny. In addition, the environment could affect the sterility in the female lines (in particular excessive heat can break sterility) and thereby result in false positive fertility restoration. Another complication with a cytoplasmic male sterility (CMS) pollination control system is that certain systems are unstable under environmental conditions so the female line will set seeds. If this occurs, this complicates detection of the restorer by crossing. Using the markers identified in the present invention (for example, TS304T and TS050 and others including the sPPR genes themselves), the genotype of plants can be quickly determined in the lab with leaf tissues collected from these plants without test crossing. This will speed up the breeding process and save the cost of labor and field resources. The markers, including the sPPR genes, will allow breeders to move important agronomic traits easily between restorer and non-restorer lines. It will also facilitate rapid phenotyping of germplasm with unknown restoration reaction. The markers and/or the sPPR genes will make it possible to access exotic germplasm more effectively and will allow diversification of the female germplasm pool leading to improved breeding progress of female lines and improved hybrid products in the long term.

Example 1

Mapping the Restorer Gene Using F2 Population and Recombinant Inbred Line (RIL)

To map the restorer gene, an F2 population and recombinant inbred line (RIL) population were created from the cross of PHB330 (non restorer) by PH1075 (restorer). RILs were produced by continually self-pollinating heads from the F2 populations until homozygosity (F5 and beyond). Initially, 300 randomly selected heads were bagged from the F2 population from the cross. The resulting F3 seeds were planted in F3 head rows. A self-pollinated (bagged) single plant was selected from each row to continue with the next generation of self-pollination. Each of the resulting RILs was characterized for restorer and non restorer capabilities by test crossing with a male-sterile female line and scoring seed set on the resulting hybrids.

It was previously reported that a *sorghum* restorer gene (Rf1) was mapped on LG-08 (previously designated as LG-H) of the *sorghum* linkage map (Klein, et al., (2001) TAG 102:1206-1212). Based on the published information, five polymorphic SSRs selected from the Rf1 gene region on LG-08 were run on 93 $F_2$ plants of the $F_2$ mapping population (PHB330×PH1075), but none of those markers was found to be associated with a restorer gene (FIG. 1). TS210 and TS354 are described in Bhattramakki, et al., (2000) *Genome* 43:988-1002. TS018 is described in Kong, et al., (2000) *TAG* 101: 438-448.

Example 2

Mapping the Restorer Gene Using Bulk Segregant Analysis

To map the restorer gene using the F2 mapping population, a bulk segregant analysis (BSA) approach was used initially to identify the target region. According to phenotypic scores, two restorer bulks and two non-restorer bulks were made from an $F_2$ population derived from the cross of PHB330 (non restorer) and PH1075 (restorer), in which each bulk consisted of 30 $F_2$ plants.

Two hundred forty fluorescent-labeled SSRs that were previously shown to have different alleles between the two parents (i.e. were polymorphic) were selected for screening the parents and bulks on the ABI377 DNA Sequencer. To generate the linkage map of the region containing the fertility gene, 15 markers were used (Table 1). Among them, eight SSR markers, TS298T, TS197, TS304T, TS297T, TS050, CS051, CS060 and TS286T from LG-02 were found putatively linked to the restorer gene.

TABLE 1

List of markers on LG B and source

| Pioneer ID | F_primer sequence | R_primer sequence | SRR Locus Sequence | SSR Repeat | Repeat morit | PCR size |
|---|---|---|---|---|---|---|
| TS391 | GCCTCAAGCCTC CTAGCCAAAT SEQ ID No 36 | CATTTCGTGGA ACTCTGTCGGG SEQ ID No 37 | CCTCGAGGGA TCGTCACTGT GGGTTTGAAC CCACCCGCGT CGCTGATGTC ATGTCCCCCC ACCGTCATGC CTCAAGCCTC CTAGCCAAAT CTGGCGCCAC ACACTCTTGA AGGAAAAGAG AGATGACAAT CCACCCATGG AGAAAATCAA CCGAGGAGAG AGAGAGAGAG AGAGAGAGAG AGAGAGAGAG AGAGAGAGAG AGATTTGGGA TTCACCCGTT GCCCCGACAG AGTTCCACGA AATGTGGCTA TGGCCACTAA ATCCGGGCCC TCTAGATGCG GCCGCATGCA TAAGCTTGAG TTATTTCTAT AGTGTCCACC CAATTAGCTT GG SEQ ID No 38 | (GA)24 | AG | 176 |
| TS096 | CGCCACACACTC TTGAAGGAAA SEQ ID No 39 | GTGGACTCTGT CGGGGCACT SEQ ID No 40 | GCNTCGCGAC TCGAATCGTC GACTCGAGGG ATCCAACCAT GGANCCCNTC GTGGANCCCA ACCGCNTCGC TGATNTCTTN TNCCCTCACC GTCNTGCNTC AANCCTCCTA GCAAATCTG GCGCCACACA CTCTTGAAGG AAAANANAGA TGACAATCCA ACCATGGAGA AANTCCCCGA AGGAGAGAGA GAGAGAGAGA GAGAGAGAGA GAGAGAGAGA GAGAGAGAGA TTGGGGATTC CCAGTGCCCC GACAGAGTCC ACNAATGTGG CTATGGCCAC TANATCCGGG CCCTCTATAT GCGGCCGCAT GCATAAGCTT GAATTATTCT ATAGTGTCCC TA SEQ ID No 41 | (GA)14/ (GA)24 | AG | 141 |
| TS080 | ATGGATGAGCA AGACACGATGC SEQ ID No 42 | GTCCTCCCACA AGACAACCCAC SEQ ID No 43 | CATTGGCAAT CGGCGANTCG ATTCGTCGAC TCGANGGATC TANANGGAGG GAGGGAGGAA NCAAANCAAA GCCAGCAGGC GATATGGATG AGCAAGACAC GATGCCTCCT GTGCCCTATA TATGGAANAT TANGGAACAG GGAGGGCGTA NCTAGCCCAA TTTCCTCTGA CCTTCGGCGC TGTCGTCGTC GTCTATGGTG GAATTGAAAG ANGTTTGTGG AGGAAGCAAC ANAAGGATAC CCNAAANAAG AGGGAGAGAG AGAGAGAGAG AGAGAGAGAG GATTATNCCT GAATGGGGAC AGGGGGGGAG GANAAAAGT GTTTGGTGTG GGTTGTCTTG TGGGAGGACA GTGCANCTGA TCCGGGCCCT CTANATGCGG CCGCATGCAT AANCTTGAGT ATTCTATANT GTCCCTA SEQ ID No 44 | (GA)13 | AG | 266 |
| TS297T | GACCCATATGTG GTTTAGTCGCAA AG SEQ ID No 45 | GCACAATCTTC GCCTAAATCAA CAAT SEQ ID No 46 | | (AAG)24 | CTT | 220 |
| TS050 | TCGTGGATTTGC ATTCCTTGAA SEQ ID No 47 | GAATGTGCCTT GTTTCTGTGCG SEQ ID No 48 | GGCAAGTCGG CCGAGCTCGA ATTCGTCGAC TCGAGGGATC ATGAAACTAC TACTCAAAAT TGGAGTTGAG AACATTGATG TTGTTACCCT TCTGGCTGAC TCTAATAATC CAGGATATAA TCGTGGATTT GCATTCCTTG AACTGGAGAC TTATAAAGAT GCACAGATAG CATACAAAAA GCTTTCAAGG AAAGATGTTT TTGGCAAGGG TTTAAATATA ACAGTTGCAT GGGCCGAACC ATTGAATGGT CGAGATGAAA AACAGATCGA GAAGGTCTCT CTCTCTCTCT CTCTCTCTCT CTCACACACA CACACACACA CCACACGCAC GCACAGAAAC AAGGCACATT CATGGACGAA CACATACATA GGCTGTTTGT GATCTAATGA AGCTGAATAT TCNTCGCAAT GCTTGCATAT AGATTANCCC TTTGCACGTG CAGGGGAACA CAACAATCAA GAGGAATTAG CANGCNATGT TTTTTGAAAT CTGCAACCAA TTTACCTGCA CCTACANAGT ACAATTGTGC TGACTCCAGG GCTAAAGCCN CCATATTACA TGCGANTGGC AGCCGGTATT TTTTGTGATA ATAGTGGCAA AATGAGAAGC TAGATCCGGG CCCTCTANAT GCCGCCGCCT GCATAANCTT GAATTTCTN TANTGTCNCC TAAATCGCTT GG SEQ ID No 49 | (CT)13 + (CA)9 | AG | 231 |
| TS304T | ACATAAAAGCC CCTCTTC SEQ ID No 50 | CTTTCACACCCT TTATTCA SEQ ID No 51 | TCTTCTTCTTCTTCTTCTTCTTCTTCTTCTTCTTCTTCTTCTT CTTCTTCTTCTTCTTCTTCTTCTTCTTCTTCTTCTTCTTCTT TTCTTCTTCTTCTTCTTCTTCTTCTGTCAAGCTGATGAATCAC CATAGGTGGAAGCTACAAGGGAGCTCATGCAGTAAACCAAGAG CGAGTCAAATACTGAGTTAACCAGGACTGCCCTTCCCATTGGA TTGAGGAGGTTGGCCTGCCATGAGCTGATATACCGGTCTGTCT TTTGAATAAAGGGTGTGAAAGA SEQ ID NO: 5 | (TCT)42 | (CTT | 206 |

TABLE 1-continued

List of markers on LG B and source

| Pioneer ID | F_primer sequence | R_primer sequence | SRR Locus Sequence | SSR Repeat | Repeat morit | PCR size |
|---|---|---|---|---|---|---|
| TS055 | GCAGGAGAGCT GCGTATCATTG SEQ ID No 52 | GGTCGGTCGGT CGTTGTTTC SEQ ID No 53 | GGCAATCGGC CGAGCTCGAA TTCGTCGACT CGAGGATCCA TGTTTGTCTG CTTTTATTAC ATTAAATAAA TAAATAAGGG GGGAATGGAC TTTCAGAACA AAGTGACTGT CTAACTTCGA ACCAAAACAT AATGCAACCT AAAATGATGC AGCACATANG AAATGTTGCC TTGTTCTTCT TCCTCGAAGT ATGGAGAGCA TGTTTCTTCA TGGCATGGGA CTATTGCCTT GTCCTTCTTC CTCATAGTAT CCTTGTTCTA CTTCCTCATA ATAGTCTTTT TTTTTCTCGA ACACGCAGGA GAGCTGCGTA TCATTGTNTT AAAAGAAGGA AGAGGAGTCT AACATANACC CACACACACA CACTCACACA CNATCAGACA AACACNCTCT CCCACNCACA TTTTCTACGCC AACCTTGATN NCTAANACTT AANCACCANA ATCTGANGAA ACAACGACCG ACCGACCGTG AGCAAGGAGA NAACCTTTTG CTCCTGACCA NCACCACCAG TGGGGCTTCA TTTCTAACCA TACTTANGGG CTGCGCCATG TTTGGATCCG GGCCTCTAAA TGCNGCCGCN TNCCTAANCT TNAATTATTC TNTNCTGTCN CCTAAATANC TTGG SEQ ID No 54 | (GA)11 + (CA)4/ (CA)11 | AG | 173 |
| CS060 | AGAGTGCAAGA AGCATGAGCCA SEQ ID No 55 | AGTAGTCCAGC AAAACGGCTGC SEQ ID No 56 | CTGCAGCATGTATATTATGGTCACACAAAAGTAGCGGGATACT ACAATGACATTCCAGCTGAGTTTATTCTGTATCATCATAATGT TCATGATCTATGAACAGGCACAGGCCTGAGGATCTTCCTCGAA TTCAGCGGGCTGACGGTGGTGGGGTGGGCGGGCAACAGTTATC GCCGCAGCAGGCGTGGCCACAGGTCACCTTCGGATGCTGCACC AGCCAGCAGCATTGGCATGCTGAAATGAAATGAAATGCATCCA TGATCAGGATCAGGAAAAAGCTGTGAGGTGATGCCAACATGCT AACAGCAGATGAGCATGACTGATGGCCTAACTGCCTGCAAGGC CGTCGGGTACACTCTACTGATGAGAATATCTTAACAGCATCTT TGGTGGCATGTCTAAGTCCTATGAATACCAAGAAATGAATCAG TCGATCTAAAGCGAAAAGAATATTTTGCAGGACTTACAGAGTG AGGCTGTCGCCATTGTGATGAAGAGTGCAAGAAGCATGAGCCA TGCGACAAGGGCGAGGGCAGTGTTCTTCATGCGGCTCATGCCT CCCTTTGTGTTGAATCTTCAGATGTCTTCTTGTGAGCAGCTGA GATGGTAATGTTGCTATGTGCTGTGTGTGTGTGTGTGTGTGTA TATATAGAGGTGACCGCCTATTCAAATTGTGATAAGATGCAGC CGTTTTGCTGGACTACTGTAGTTATTGGACTGTTGACGCCATC TAGATCTCTCTGTGTTGACTCTTGAGATGGTGGTTTTGATAAT TTGTTTCCTAGCTGACGTTTCTTCGAATACAACTTCCATTGTG ATGTGGCCAGGTGGATTAACCAGTTACAAAATTTACTACACAC CGAATTTCCTGCAG SEQ ID No 57 | (TG)9 | AC | 211 |
| TS298T | GCATGTGTCAGA TGATCTGGTGA SEQ ID No 58 | GCTGTTAGCTT CTTCTAATCGTC GGT SEQ ID No 59 | | (AGA)23 | CTT | 202 |
| TS019N | TCGAGGGATCA AACTTTCAATCG SEQ ID No 60 | CGTCTGCTCCG TGACTCTCCAT SEQ ID No 61 | CCCCTCTCCCNTTTTTNNNTCNCTCAANNCGGCCGACCCCGA ATTCGTCGACCTCGAGGGATCAAACTTTCAATCGGTTCCAGAC GGGGAGAGACAGAGGAAGGGGGGGGGAGAGAGAGAGGGTCCA GTNAGAGATGGAGAGTCACGGAGCAGACGGNGTGGGAGGGAGA AGACGANGGTAGANGACGACTCGTNCAGGAGAGAGAGGGAGAT ACAGTTACAGNGCATGGAGACATAGAGAGCAGAGAGAGAGACG GCGANGTCGNAGNCNCANTCATNNCTC SEQ ID No 62 | (GA)5 + (GA)8/ (GA)5 (GA)5 | AG | 208 |
| CS050 | TGGGGAAAAAG AAAGCCATCAG SEQ ID No 63 | CGCTTCAGTTA GGTGTGGCTCA SEQ ID No 64 | CTGCAGGTGTGGCGGCATGCAGCACTGGTGCGAGACAGCGGGA CGACTGCCATGACGACGCTCTGCATTGCATGTACTACAGTAGT ACTAACCAGCATGGGGAAAAAGAAAGCCATCAGAGTAAAGGG CAAGGCAACAAGAGACCCGGACGGAGAGTGCAATGCCATGAGG ATGCGGATGCGGATGCGGATGCGGCCTTGGAAACGTACTACGG GAGGAGTAAATGCCGTCCCGGCTCTCGCTCGCGCTTGCAGATT TTGTAGGGCGCCATTGACATCTTCCTTCCCTGCTTTCTCGGCA CTGCCCTGCTAGCTGCTTCATGCGTGCATGAGCCACACCTAAC TGAAGCGCTGTAGTAAAAAGAAACAGCCAGGCGCTCGATCT CATGCAAGCCATGACCTCCTCATGATGGTTGATGGAAAGGTTC AGCTCTTTCGACCGGCCGTTGCATGCATGAGTGCTCCAGTTGA GGCAGCATGTGAATGATAAAATACTGCTGAATCAGTAAGCCCT ATACACACATACATATATATCCTAGAGACTTTGGGGAACTACT TCATAAAACCACTCAAAAATTCAGTGCATGCAGGTGCATGGA GAAGGAACATCGCATGGTTGAATTGAACGCTGGTTGTT TTACTGAAGAAAGCTCAATGAGACACGGTCAATGCAAAGGAGA GAGAGACAGATCGAGAGGGAAAGAGATTAGAGACAGAAAAAC AATGTAGTAGGAGCATACTCAGAGTGATGGAATTGAATGCTGC AG SEQ ID No 65 | (GGATGC) 4 | TETRAD | 253 |

TABLE 1-continued

List of markers on LG B and source

| Pioneer ID | F_primer sequence | R_primer sequence | SRR Locus Sequence | SSR Repeat | Repeat morit | PCR size |
|---|---|---|---|---|---|---|
| TS286T | AGCAGCAGCAGCAACAG SEQ ID No 66 | GCGTGGTCTTTGTGGTTC SEQ ID No 67 | | (GCA)4 ACA(GCA)5 | CGT | 197 |
| CS051 | ACGGACGGGAACAGAGAAAGAA SEQ ID No 68 | ACGAGGACGAGTGCATGATGAG SEQ ID No 69 | CTGCAGTGTGTAAGTGGATTTTATTTCCTTTTATATTAATTAA TAGAAAGCCAGGAAAGAAGTTTACGATCGGTTCATGGATTCGC TGTGATCAGCACACATGATTGATGAACAGGTGCAAGAAATTGA CGGGATCTTTTGAGAAGAGCAAGAGCTCGATCCGGTCGTGCGG GAACGAACTGGCAGAGATAGATCGATACGTACTGCACGACGTT GTAACTGTGACGAATCCAATGCAGCATGCATGCACATTGAATT TCATGCATGCGTTTGTAAGTTTGGTGAATAAATACTGAAACGA AGTTCATGCATGCGTTCTGAAGTTTGGTGCATGATACTGAAAC TTTGCGTTCTGAAGTTTGGTGGATAATACTTGAACTTTTCTGA ATGCGTACATACATGCATAGAATGAAACAACAAACAAGAAATC CTCGAGATGAAACAACAAGCAAGAAATCCTCGAGCTAGGATGG ATAGATCGATCGATGGATCACTACTGTGACATGGGACAAAAAA AGAAAAATCGAAACTGTTATTATTGACACGCAGGTAACGCGCC ATGCACAGTGTTCACACGCCACGGACGGGAACAGAGAAAGAAC ACGACGAGCACGGAGCAACGCATGTCGTATATATATATATATA TAGCCTAGGATATAGATAGGAGAGGGATGATGATGGATCAGTT GTGGTGCTGCTGGGTGTAGATGTAGTCGGTGTGCGCGTTCAGC GTGCGCCTCATCATGCACTCGTCCTCGTCGTTGGCGCCCTCGC ACCCGCCTTCCGTTTCCGCCGATCCCTGCTTCTGCAG SEQ ID No 70 | (TA)9 | AT | 180 |
| TS197 | TCCAAACAGCCTCTTGGTACGC SEQ ID No 71 | AACAAGGGAATTTTGTCGTCCG SEQ ID No 72 | CGTCGACTCG ANGGATCTTG GCGTCAATTA ATCCAAACAG CCTCTTGGTA CGCATCAATT ATTGGTTAGA TATATTTTAA GCTGCCCATA TGTTTCTTCA TCAGGTCACA ACACACACAC ACACACACAC AAAAAAAAAA ACTTGGCCTG CAATCAGCAT CACCATGAAC GGGAATAGGA ACTCTTGCTG CCAAGTGGAT GGTCTGTCTT TGCGGACGAC AAAATTCCCT TGTTCTTAGA ATATGTAGTA ATAATATATT AAGAGTATGT TTAGATCCCT ATAAAGAATA TTATAATTTT TTCAGGATCC GGGCCCTCTA GATCGGCGCA TGCATAAGCT TGAGTATCTA TATGTCCCTA AATACTGGCT ATCAGGTCAA GCGTTCTGTG TGAATGTATC GCTCCATCAC CACATACAGC CGAACTAATT AACCGGGTCT ATATGACACC CTATGCTGCC CCGCCGCTCA TCGGAACGTC TCACGCTATA TCGCACCCGG AAGCGTGGTT GGCCCTCCTC CCCATACCCG CCCGCTCGCN CGCACGA-CAC CCCAAGGTAC GTC SEQ ID No 73 | (AC)10 | AC | 203 |
| SDB043 | CGACGAACGAACGAGCAAAAG SEQ ID No 74 | CGTGTGGACGACGAATTGAGTT SEQ ID No 75 | GCACGAGGATCATCTCTAGCTCGTCTTGTTCGTCCTCCTTGGA AGGAAGCAGCAATTTGTTGCTCACCTCCACACGGCCTGCTTAT TATTTTTAGCAAAAGCAGGCACAGGCAGGAGAAGAGAGGAGA GGGGGCGACGAGGGCAACGCATCAAATCGATAGATCAATCACT GCTGCTCCTGCTCGTCGTGGTCAGCCGCCAGCGACGAACGAAC GAGCAAAAGGCCGGCTGATTTGCTCTCTCTCTCTCTCTCTCTC TCTCTCTCTCTGCTCTGCTAGTGGCGCCGAATCAATCAATC AATTTCAATCACAAAGTTAAGTTGGAATTTTGATTGCTCCATA TATAAAACTCAATTCGTCGTCCACACGACATTAATTGGATCGGA ATCGGAATCGGACCACCCACCATCAGAAAGCAAAGCAGAGGAA GGCAGTCCATTCAAGATTGGAAGGC SEQ ID No 76 | (CT)18 | AG | 167 |

Example 3

Mapping the Restorer Gene with F2 Population

Based on the BSA results, the entire population consisting of 270 F₂ plants from the cross of PHB330×PH1075 were run with 11 SSR markers selected from the region identified on LG-02 of *sorghum* public linkage map. These markers included SDB043, TS197, CS051, TS297T, TS050, TS304T, CS060, TS055, TS298T, TS019N and TS286T. Mapping results confirmed that the restorer gene is located on LG-02.

Example 4

Confirming the Mapping Location of Restorer Gene with RIL Population

To determine the location of the restorer gene previously mapped to LG-02 in an F₂ population, a recombinant inbred line (RIL) population was developed. The RIL population consisted of 132 RILs derived from the same cross as the F₂ (PHB330×PH1075). Flanking SSRs (TS050, CS060, TS055 and TS304T) were selected from the putative region of LG-02 based on previous mapping results and run on the RIL population. Analysis confirmed that SSRs TS304T and TS050 were tightly linked to the restorer gene (FIG. 3). Table 2 shows the forward and reverse primers used to amplify TS304T and TS050. The location of the primers is underlined in SEQ ID NO: 5 and SEQ ID Na 6 below. The forward primer for SEQ ID NO: 5 sits outside the partial sequence of the marker TS304T.

TABLE 2

| Primer Name | Primer Sequence | SEQ ID NO: |
|---|---|---|
| TS304T_F | ACATAAAAGCCCCTCTTC | SEQ ID NO: 1 |
| TS304T_R | CTTTCACACCCTTTATTCA | SEQ ID NO: 2 |
| TS050_F | TCGTGGATTTGCATTCCTTGAA | SEQ ID NO: 3 |
| TS050_R | GAATGTGCCTTGTTTCTGTGCG | SEQ ID NO: 4 |

```
TS304T PARTIAL SEQUENCE (280 bp)
                                            SEQ ID NO: 5
TCTTCTTCTTCTTCTTCTTCTTCTTCTTCTTCTTCTTCTTCTTCTTCTTCT

TCTTCTTCTTCTTCTTCTTCTTCTTCTTCTTCTTCTTCTTCTTCTTCTTCT

TCTTCTTCTTCTTCTGTCAAGCTGATGAATCACCATAGGTGGAAGCTA

CAAGGGAGCTCATGCAGTAAACCAAGAGCGAGTCAAATACTGAGTTAA

CCAGGACTGCCCTTCCCATTGGATTGAGGAGGTTGGCCTGCCATGAGC

TGATATACCGGTCTGTCTTTTGAATAAAGGGTGTGAAAGA

TS050 SEQUENCE 682 bp
                                            SEQ ID NO: 6
GGCAAGTCGG CCGAGCTCGA ATTCGTCGAC TCGAGGGATC

ATGAAACTACTACTCAAAAT TGGAGTTGAG AACATTGATG

TTGTTACCCT TCTGGCTGAC TCTAATAATC CAGGATATAA

TCGTGGATTT GCATTCCTTG AACTGGAGAC TTATAAAGAT

GCACAGATAG CATACAAAAA GCTTTCAAGG AAAGATGTTT

TTGGCAAGGG TTTAAATATA ACAGTTGCAT GGGCCGAACC

ATTGAATGGT CGAGATGAAA AACAGATGCA GAAGGTCTCT

CTCTCTCTCT CTCTCTCTCT CTCACACACA CACACACACA

CCACACGCAC GCACAGAAAC AAGGCACATTCATGGACGAA

CACATACATA GGCTGTTTGT GATCTAATGA AGCTGAATAT

TCNTCGCAAT GCTTGCATAT AGATTANCCC TTTGCACGTG

CAGGGGAACA CAACAATCAA GAGGAATTAG CANGCNATGT

TTTTTGAAAT CTGCAACCAA TTTACCTGCA CCTACANAGT

ACAATTGTGC TGACTCCAGG GCTAAAGCCN CCATATTACA

TGCGANTGGC AGCCGGTATT TTTTGTGATA ATAGTGGCAA

AATGAGAAGC TAGATCCGGG CCCTCTANAT GCCGCCGCCT

GCATAANCTT GAATTTTCTN TANTGTCNCC TAAATCGCTT

GG
```

These sequences were then used to BLAST the *sorghum* database that covers 8.5× the *sorghum* genome (Paterson, et al., (January 2006) *Nature* 457:551-556, details also found in http://genome.jgi-pstorg/Sorbi1/Sorbi1.info.html) in order to identify a region containing candidate restorer gene(s) (see, Example 6).

Example 5

Marker-Trait Association Study

To further confirm the mapping result from F₂ as well as RIL populations, a marker-trait association study was conducted using 253 fingerprinted inbred lines (124 restorer lines and 129 non-restorer lines) with known restorer phenotype. SEQ ID NO: 5 and SEQ ID NO: 6 were used to generate primers including those listed in Table 2. The primers were used to genotype restorer and non-restorer lines. The study revealed that 12 alleles of TS304T were associated with 100% of the 118 restorer lines and 12 different alleles were associated with 100% of the 70 non-restorer lines. Another four alleles were present in 59 maintainer lines as well as 6 restorer lines. The results provided strong evidence that marker TS304T is highly associated with a restorer gene in *sorghum* (Table 3).

A similar study revealed that two alleles of TS050 were associated with 100% of the 41 restorer lines and 3 different alleles were associated with 100% of the 12 non-restorer lines. Another 5 alleles were present in 126 maintainer lines as well as 102 restorer lines. The results provided strong evidence that marker TS050 is highly associated with a restorer gene in *sorghum* (Table 3).

Twenty three populations were screened using the SSR markers TS304T and TS050 or TS297T. These markers were chosen because polymorphism was shown in the parental lines. In a majority of the populations, the SSR markers segregated 1:2:1 thereby confirming the linkage (Table 4).

The markers can also be used in marker assisted selection (MAS) as shown in Table 5. In the example provided, TS050 and TS304T were used, but other markers of the invention can also be used as is known to those skilled in the art.

TABLE 3

Association analysis of markers TS304T and TS050 with inbred sorghum lines of known fertility

|  | TS304T alleles | Allele size (bp) | TS050 alleles | Allele size (bp) |
|---|---|---|---|---|
| Restorer Specific Alleles | b | 209 | a | 224 |
|  | c | 212 | j | 242 |
|  | e | 245 |  |  |
|  | f | 248 |  |  |
|  | g | 254 |  |  |
|  | h | 257 |  |  |
|  | i | 260 |  |  |
|  | j | 263 |  |  |
|  | y | 279 |  |  |
|  | z | 215 |  |  |
|  | aa | 239 |  |  |
|  | bb | 282 |  |  |
| Maintainer Specific Alleles | k | 269 | b | 226 |
|  | l | 272 | h | 249 |
|  | m | 288 | i | 232 |
|  | n | 297 |  |  |
|  | o | 300 |  |  |
|  | p | 301 |  |  |
|  | r | 307 |  |  |
|  | s | 313 |  |  |
|  | t | 197 |  |  |
|  | u | 291 |  |  |
|  | w | 242 |  |  |
|  | x | 285 |  |  |

TABLE 4A

Segregation for fertility marker alleles of TS304T among F2 plants in sorghum populations (ns = not significant at $P > 0.01$ level, * = significant at $P < 0.01$ level, ** = significant at $P < 0.001$ level).

| | SSR Marker TS304T | | | | Evaluation of fertility markers in sorghum breeding program | | |
|---|---|---|---|---|---|---|---|
| Population | Maintainer | Heterozygous | Restorer | Chi-Square (1:2:1 Ratio) | Selections by breeders | Number that do not match | Success Rate |
| Manhattan, Texas 1 | 82 | 131 | 64 | 3.15 ns | 14 | 2 | 86% |
| Manhattan, Texas 2 | 80 | 115 | 78 | 6.8 ns | 20 | 6 | 70% |
| Manhattan, Texas 3 | 65 | 130 | 78 | 1.86 ns | 9 | 0 | 100% |
| Manhattan, Texas 4 | 74 | 136 | 62 | 1.06 ns | 16 | 0 | 100% |
| Manhattan, Texas 5 | 42 | 77 | 36 | 0.47 ns | 22 | 5 | 77% |
| Manhattan, Texas 6 | 75 | 105 | 80 | 9.81* | 10 | 0 | 100% |
| Manhattan, Texas 7 | 123 | 71 | 54 | 83.7** | 26 | 0 | 100% |
| Manhattan, Texas 8 | | | | | 8 | 1 | 88% |
| Manhattan, Texas 9 | 70 | 118 | 86 | 7.14 ns | 20 | 0 | 100% |
| Taft, Texas 1 | | | | | | | |
| Taft, Texas 2 | 61 | 135 | 69 | 0.58 ns | | | |
| Taft, Texas 3 | 64 | 141 | 68 | 0.41 ns | | | |
| Taft, Texas 4 | 103 | 115 | 56 | 23.19** | | | |
| Taft, Texas 5 | 65 | 141 | 66 | 0.38 ns | | | |
| Taft, Texas 6 | 50 | 144 | 59 | 5.48 ns | | | |
| Taft, Texas 7 | 78 | 127 | 74 | 2.35 ns | | | |
| Taft, Texas 8 | 124 | 100 | 53 | 57.8** | | | |
| Taft, Texas 9 | | | | | | | |
| Puerto Vallart, Mexico 1 | 95 | 129 | 109 | 18.07* | | | |
| Puerto Vallart, Mexico 2 | 76 | 183 | 102 | 3.81 ns | | | |
| Puerto Vallart, Mexico 3 | 85 | 160 | 102 | 3.77 ns | | | |
| Puerto Vallart, Mexico 4 | | | | | | | |
| Puerto Vallart, Mexico 5 | 69 | 165 | 110 | 10.34* | | | |

TABLE 4B

Segregation for fertility marker alleles of TS050 among F2 plants in sorghum populations (ns = not significant at $P > 0.01$ level, * = significant at $P < 0.01$ level, ** = significant at $P < 0.001$ level).

| | SSR Marker TS050 | | | | Evaluation of fertility markers in sorghum breeding program | | |
|---|---|---|---|---|---|---|---|
| Population | Maintainer | Heterozygous | Restorer | Chi-Square (1:2:1 Ratio) | Selections by breeders | Number that do not match | Success Rate |
| Manhattan, Texas 1 | 86 | 128 | 64 | 5.22 ns | 14 | 2 | 86% |
| Manhattan, Texas 2 | 87 | 123 | 66 | 6.46 ns | 20 | 6 | 70% |
| Manhattan, Texas 3 | 60 | 136 | 77 | 2.12 ns | 99 | 0 | 100% |
| Manhattan, Texas 4 | 70 | 141 | 60 | 1.18 ns | 16 | 0 | 100% |
| Manhattan, Texas 5 | 41 | 79 | 36 | 0.35 ns | 22 | 5 | 77% |

TABLE 4B-continued

Segregation for fertility marker alleles of TS050 among F2 plants in *sorghum* populations (ns = not significant at P > 0.01 level, * = significant at P < 0.01 level, ** = significant at P < 0.001 level).

| Population | SSR Marker TS050 | | | | Evaluation of fertility markers in *sorghum* breeding program | | |
|---|---|---|---|---|---|---|---|
| | Maintainer | Heterozygous | Restorer | Chi-Square (1:2:1 Ratio) | Selections by breeders | Number that do not match | Success Rate |
| Manhattan, Texas 6 | 75 | 115 | 81 | 6.47 ns | 10 | 0 | 100% |
| Manhattan, Texas 7 | 148 | 78 | 45 | 127.1** | 26 | 0 | 100% |
| Manhattan, Texas 8 | 45 | 149 | 81 | 11.35* | 8 | 1 | 88% |
| Manhattan, Texas 9 | | | | | 20 | 0 | 100% |
| Taft, Texas 1 | | | | | | | |
| Taft, Texas 2 | 64 | 143 | 70 | 0.55 ns | | | |
| Taft, Texas 3 | 66 | 143 | 67 | 0.37 ns | | | |
| Taft, Texas 4 | | | | | | | |
| Taft, Texas 5 | 69 | 145 | 65 | 0.55 ns | | | |
| Taft, Texas 6 | | | | | | | |
| Taft, Texas 7 | | | | | | | |
| Taft, Texas 8 | 104 | 117 | 56 | 23.31** | | | |
| Taft, Texas 9 | 86 | 133 | 57 | 6.46 ns | | | |
| Puerto Vallart, Mexico 1 | 89 | 160 | 84 | 0.66 ns | | | |
| Puerto Vallart, Mexico 2 | 80 | 189 | 90 | 1.56 ns | | | |
| Puerto Vallart, Mexico 3 | 92 | 188 | 80 | 1.51 ns | | | |
| Puerto Vallart, Mexico 4 | 86 | 192 | 90 | 0.78 ns | | | |
| Puerto Vallart, Mexico 5 | 81 | 160 | 104 | 4.88 ns | | | |

TABLE 4C

Segregation for fertility marker alleles of TS297T among F2 plants in *sorghum* populations (ns = not significant at P > 0.01 level, * = significant at P < 0.01 level, ** = significant at P < 0.001 level).

| Population | SSR Marker TS297T | | | | Evaluation of fertility markers in *sorghum* breeding program | | |
|---|---|---|---|---|---|---|---|
| | Maintainer | Heterozygous | Restorer | Chi-Square (1:2:1 Ratio) | Selections by breeders | Number that do not match | Success Rate |
| Manhattan, Texas 1 | | | | | 14 | 2 | 86% |
| Manhattan, Texas 2 | | | | | 20 | 6 | 70% |
| Manhattan, Texas 3 | | | | | 9 | 0 | 100% |
| Manhattan, Texas 4 | | | | | 16 | 0 | 100% |
| Manhattan, Texas 5 | | | | | 22 | 5 | 77% |
| Manhattan, Texas 6 | | | | | 10 | 0 | 100% |
| Manhattan, Texas 7 | | | | | 26 | 0 | 100% |
| Manhattan, Texas 8 | | | | | 8 | 1 | 88% |
| Manhattan, Texas 9 | | | | | 20 | 0 | 100% |
| Taft, Texas 1 | 50 | 139 | 89 | 10.94* | | | |
| Taft, Texas 2 | | | | | | | |
| Taft, Texas 3 | | | | | | | |
| Taft, Texas 4 | 115 | 112 | 52 | 39.29** | | | |
| Taft, Texas 5 | | | | | | | |
| Taft, Texas 6 | 67 | 137 | 58 | 1.17 ns | | | |
| Taft, Texas 7 | | | | | | | |
| Taft, Texas 8 | | | | | | | |
| Taft, Texas 9 | | | | | | | |
| Puerto Vallart, Mexico 1 | | | | | | | |
| Puerto Vallart, Mexico 2 | | | | | | | |
| Puerto Vallart, Mexico 3 | | | | | | | |
| Puerto Vallart, Mexico 4 | | | | | | | |
| Puerto Vallart, Mexico 5 | | | | | | | |

TABLE 5

Example of MAS for *sorghum* fertility trait using flanking markers
TS304T and TS050 on the Manhattan, Texas - Population 1.

| Sample Name | TS050 | Result | TS304T | Result |
|---|---|---|---|---|
| Parent 1 | c | maintainer | k | maintainer |
| Parent 2 | a | restorer | j | restorer |
| 3 | a, c | heterozygous | j, k | heterozygous |
| 4 | a, c | heterozygous | j, k | heterozygous |
| 5 | a | restorer | j | restorer |
| 6 | c | maintainer | k | maintainer |
| 7 | a | restorer | j | restorer |
| 8 | c | maintainer | k | maintainer |
| 9 | a, c | heterozygous | j, k | heterozygous |
| 10 | a, c | heterozygous | j, k | heterozygous |
| 11 | a, c | heterozygous | j, k | heterozygous |
| 12 | c | maintainer | k | maintainer |
| 13 | a, c | heterozygous | j, k | heterozygous |
| 14 | a, c | heterozygous | j, k | heterozygous |
| 15 | a, c | heterozygous | j, k | heterozygous |
| 16 | c | maintainer | k | maintainer |
| 17 | a | restorer | j | restorer |
| 18 | a | restorer | j | restorer |
| 19 | a, c | heterozygous | j, k | heterozygous |
| 20 | a, c | heterozygous | j, k | heterozygous |
| 21 | a, c | heterozygous | j, k | heterozygous |
| 22 | c | maintainer | k | maintainer |
| 23 | a, c | heterozygous | j, k | heterozygous |
| 24 | a | restorer | j | restorer |
| 25 | c | maintainer | k | maintainer |
| 26 | c | maintainer | k | maintainer |
| 27 | a, c | heterozygous | j, k | heterozygous |

In summary, this example confirms that TS304T and TS050 are associated with the fertility restorer gene and certain alleles segregate with restorer and non-restorer germplasm. This example also confirms that the markers can be used in MAS.

Accordingly, it can be concluded that a restorer gene is located on LG-02 of the public SSR linkage map (Menz, at al., (2002) *Plant Molecular Biology* 48:483-499). TS304T and TS050 flank the restorer gene with 1 and 3 cM mapping distance, respectively; as determined by JoinMap 3.0. The mapping information is useful for marker-assisted selection of the restorer gene. The flanking markers, and/or other markers of the invention, can be used individually or in combination for marker assisted selection and/or segregation analysis. Using molecular markers to differentiate between restorer and non-restorer lines will simplify the identification of restorers and non-restorers from a restorer by non-restorer cross at the F2 generation. This will reduce the time and effort involved in making testcrosses and scoring seed set in the resulting hybrids.

Example 6

Identification of Putative Restorer Genes in the Vicinity of the TS304T and TS050 Markers on *Sorghum* Chromosome 2

As detailed in Example 4, *sorghum* chromosome 2—Locus 5.080 Mb-5.703 Mb was identified as a region containing the *sorghum* fertility gene. The position was determined based on Chromosome2 sequence numbering taken from the *sorghum* genome data base (http://www.plantgdb.org/SbGDB/cgi-bin/getRegion.pl). (http://www.plantgdb.org/SbGDB/index.php version from JGI Sbi 1(10 Sep. 2007); see also, Paterson, et al., (January 2009) *Nature* 457:551-556). The TS050 marker starts at 5079956 bp and the TS304 marker ends at 5703494 bp. This interval is 623 kb in length (623021 bp) (see, Table 6). This was determined from the start of the locus of TS304 to the end of locus TS050 (i.e., 5703327–5080306=623021).

As stated above, the *sorghum* genome has been sequenced (Paterson, et. al., (January 2009) *Nature* 457:551-556 and http://genome.jgi psf.org/Sorbi1/Sorbi1.info.html) and the entire genomic region between TS050 and TS304 (623 kb) was translated for gene prediction using FGENESH from the sequence software suite from Pioneer bioinformatics site. Predicted genes were manually BLASTed with the rice/Arabidopsis data base to scan for genes containing the pentatrico peptide repeat (PPR) motif since PPR motif is found in many restorer genes as known in the art (or example, petunia (Bentolila, et al., (2002) *PNAS* 99:10887-892), rice (Akaki, et al., (2004) *Theor Appl Genet.* 108(8):1449-57) and radish (Brown, et al., (2003) *Plant J.* 35(2):262-72). The canola restorer gene for the ogura cytoplasm was found in a cluster of three PPR genes (Brown, et al., (2003) *Plant J.* 35(2):262-72).

The entire 623 kB region was translated for gene prediction and scanned for genes containing the PPR motif. Of the 95 predicted genes in this interval, four PPR-motif-containing genes were identified using FGENESH prediction software. The genes were named sPPR1, sPPR2, sPPR3 and sPPR4 depending on the distance to TS304T. sPPR1 is the one closest to TS304T at approximately 134 kB. A gene flanking TS304T away from TS050 was found with a PPR motif and named sPPR5. sPPR5 is 39 kB from TS304T. Table 6 summarizes the data for the five putative sPPR genes. Sequences were analyzed and primers were designed specific to each gene for sequencing purposes. The following sequences were identified:

SEQ ID NO: 7—sPPR1 ORF. 13 exons.
SEQ ID NO: 8—sPPR1 genomic
SEQ ID NO: 9—sPPR2 ORF. 7 exons.
SEQ ID NO: 10—sPPR2 genomic
SEQ ID NO: 11—sPPR3 ORF. 2 exons.
SEQ ID NO: 12—sPPR3 genomic
SEQ ID NO: 13—sPPR4 ORF. 1 exon.
SEQ ID NO: 14—sPPR4 genomic
SEQ ID NO: 15—sPPR5 ORF. 2 exons.
SEQ ID NO: 16—sPPR5 genomic
SEQ ID NO: 17—sPPR1 predicted amino acid sequence
SEQ ID NO: 18—sPPR2 predicted amino acid sequence
SEQ ID NO: 19—sPPR3 predicted amino acid sequence
SEQ ID NO: 20—sPPR4 predicted amino acid sequence
SEQ ID NO: 21—sPPR5 predicted amino acid sequence The five putative PPR-containing genes are very similar. In particular, sPPR1, sPPR3 and sPPR4 are very similar. sPPR2 and sPPR5 are slightly diverged. sPPR1 is approximately 15.4 kb in length and contains 12 introns with the largest intron being the first intron at 1412 bp in size. Table 6 lists the characteristics of the 5 PPR genes. FIG. 4 shows the alignment of sPPR1, sPPR3, sPPR4 and sPPR5 genes.

TABLE 6

Characteristics of the PPR genes, their physical location on Chromosome 2 and distance with respect to TS304T

| Gene | | ORF size | size | Strand | *Sorghum* Locus Ch2 start | *Sorghum* Locus Ch2 end | Distance to TS304 bp | F2 map | SSR Genetic map | RIL map |
|---|---|---|---|---|---|---|---|---|---|---|
| SCH2 5080-5703kb | | | | | 5,080,060 | 5,703,490 | | | | |
| TS050 | SSR | 682 | | | 5,079,956 | 5,080,306 | 623,021 | 24 cM | 27.5 cM | 23 cM |

TABLE 6-continued

Characteristics of the PPR genes, their physical location on Chromosome 2 and distance with respect to TS304T

| Gene | | size | ORF size | Strand | Sorghum Locus Ch2 start | Sorghum Locus Ch2 end | Distance to TS304 bp | F2 map | SSR Genetic map | RIL map |
|---|---|---|---|---|---|---|---|---|---|---|
| sPPR4 | genomic | 2866 | | Minus | 5,169,517 | 5,172,382 | 530,945 | | | |
| | ORF | 1599 | 1599 | | 5,169,697 | 5,171,295 | | | | |
| sPPR3 | Genomic | 2997 | | Minus | 5,187,133 | 5,190,129 | 513,198 | | | |
| | ORF | 2091 | 2091 | | 5,187,528 | 5,189,734 | | | | |
| sPPR2 | genomic | 6291 | | Plus | 5,287,338 | 5,293,628 | 409,699 | | | |
| | ORF | 2880 | 2880 | | 5,287,724 | 5,293,515 | | | | |
| sPPR1 | genomic | 15426 | | Plus | 5,552,994 | 5,568,419 | 134,908 | | | |
| | ORF | 5079 | 5079 | | 5,554,498 | 5,567,310 | | | | |
| TS304 | SSR | 280 | | | 5,703,327 | 5,703,494 | | 28 cM | 34.6 cM | 19.1 cM |
| SCH2 5700kb-5900kb | | | | | 5,700,000 | 5,900,000 | | | | |
| sPPR5 | genomic | 2771 | | Minus | 5,742,986 | 5,745,756 | 39,492 | | | |
| | ORF | | 1881 | | 5,743,105 | 5,744,959 | | | | |

Example 7

Identification of Simple Nucleotide Polymorphisms (SNPs) that Segregate with Restorer and Non-Restorer Germplasm in the Five Putative Restorer Genes Approximately 5 kb comprising the sPPR1, sPPR2, sPPR3 and sPPR5 genes were PCR amplified and sequenced from PH1075 (Restorer) and PHB330 (Maintainer) and scanned for polymorphisms. The 5' untranslated regions and exon 1 were targeted for sequencing to identify SNPs. In the regions of the putative genes that were sequenced, SNPs were identified only in sPPR1. sPPR1 was amplified from several *sorghum* restorer and maintainer lines to confirm that the polymorphisms are consistent with the restorer and maintainer lines. FIG. 5 shows the alignment of PPR1 sequences from Pioneer restorer and maintainer lines as haplotypes 1, 2, 3 and 4 (SEQ ID NOS: 22-25). The restorer and maintainer lines were selected based on their phenotype and then analyzed for genotype. The SNPs are indicated with an asterisk. As shown in FIG. 5, twenty-seven SNPs were identified in sPPR1. Four haplotypes were identified. A summary of the information is found in Table 7. The SNP position is based on its distance from the ATG start of the sPPR1 gene.

TABLE 7

| Position* | HAP1 | HAP2 | HAP3 | HAP4 |
|---|---|---|---|---|
| 1600 | G | G | A | G |
| 1607 | C | C | A | C |
| 1610 | T | T | C | T |
| 1611 | C | C | G | C |
| 1616 | G | G | A | G |
| 1618 | G | G | T | G |
| 1656 | A | G | G | A |
| 1664 | A | G | G | A |
| 1675 | G | G | G | T |
| 1705 | G | A | A | A |
| 1724 | T | C | C | C |
| 1785 | G | G | T | G |
| 1810 | G | G | A | G |
| 1819 | A | T | A | T |
| 1820 | T | T | A | T |
| 1821 | T | T | C | T |
| 1822 | T | T | C | T |
| 1825 | G | G | A | G |
| 1826 | C | C | A | C |
| 1834 | T | T | C | T |
| 1846 | G | G | C | G |
| 1853 | A | A | T | A |
| 1854 | G | G | T | G |
| 1857 | A | A | C | A |
| 1863 | T | T | A | T |
| 1866 | TG | TG | AA | TG |
| 1867 | G | G | A | G |

*SNP position with respect to ATG start of sPPR1 gene

Of the lines analyzed, Haplotype 1 (HAP1) and Haplotype 3 (HAP3) comprise all maintainer lines, except R633 which has the phenotype of a restorer. Haplotype 2 (HAP2) and Haplotype 4 (HAP4) comprise all restorer lines, except M048 which has the phenotype of a maintainer.

The discrepancy with R633 and M048 can be explained in several ways. As is known to those skilled in the art, discrepancies between markers and phenotype are not unusual. A marker is associated with a phenotype, but does not define it. In addition, M048 and R633 may have some other changes either in TRANS or in CIS that would compensate for the discrepancies. FIG. 5 contains the sequencing information for the first exon. Additional SNPs are likely downstream. Further, the sequences of M048 appear to contain a mixture of maintainer and restorer sequences. This may be due to sample contamination. Further, R633 may have a different restoration capability compared with other restorer lines and M048 may have a different maintainer capability compared with other maintainer lines. Finally, the pedigree of R633 includes germplasm not widely used in the other lines.

The SNP used for mapping the population is SNP1616 (originally named from ATG start which corresponds to position 280-1 in FIG. 5). For the Taqman™ assay SNP 1705 (position 375 in FIG. 5 for Hap1 versus Hap2) and SNP1863, SNP1866 and SNP1867 (positions 532, 535, 536 in FIG. 5 for Hap3 versus Hap2) were targeted.

Figure 6:
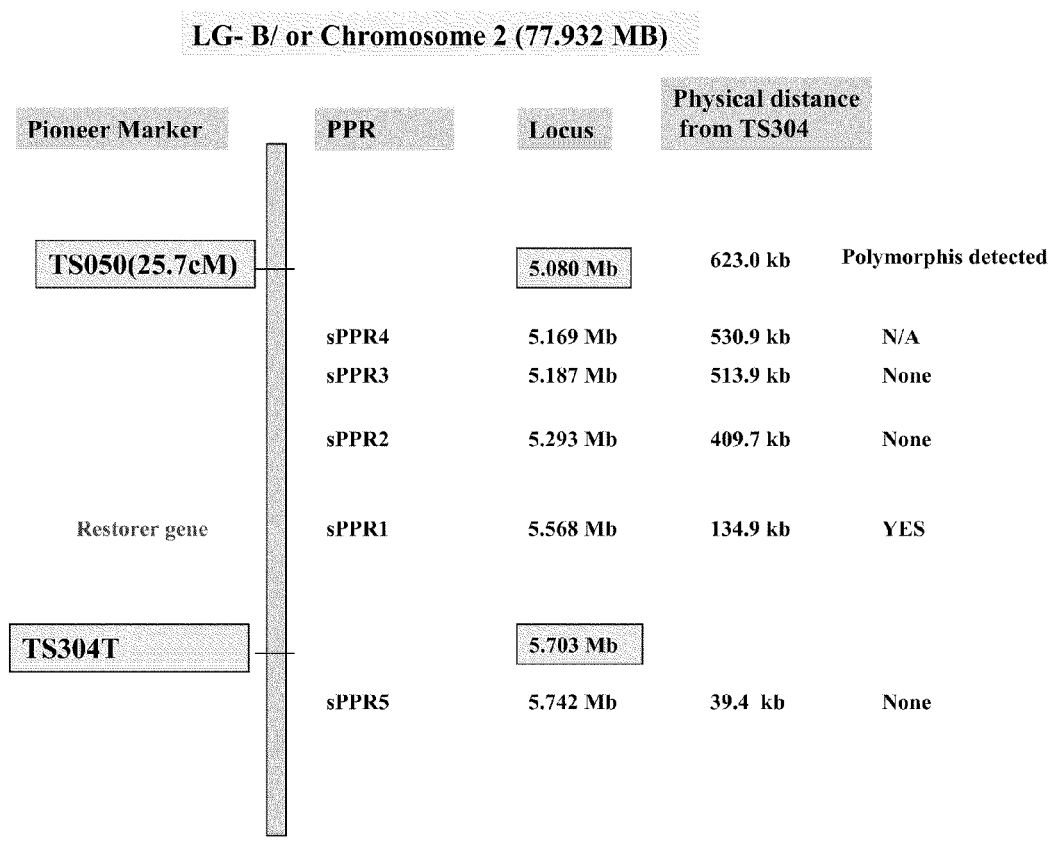
FIG. 6 shows the position of the PPR genes and physical distance between the PPR genes and the SSR markers identified on chromosome 2.

Each haplotype indicated in FIG. 5 has been given a SEQ ID NO: as follows:
Haplotype 1 (HAP1) SEQ ID NO: 22
Haplotype 2 (HAP2) SEQ ID NO: 23
Haplotype 3 (HAP3) SEQ ID NO: 24
Haplotype 4 (HAP4) SEQ ID NO: 25
FIG. 6 shows the approximate location of the sPPR genes in relation to the SSR markers TS050 and TS304T.

Example 8

Confirmation that sPPR1 Lies in the Interval Between SSR Markers TS050 and TS304T To verify that the PPR1 gene was located between SSR markers TS050 and TS304T, the PPR1 gene was mapped onto LG_02 (LG_B) by genotyping the mapping population PHB330 (maintainer, Hap3)×PH1075 (restorer, Hap2) with the SNP that corresponds to position 280-1 in FIG. 5. This SNP was labeled SNP1616.

The following primers were used to map the sPPR1 gene to chromosome 2 of the *sorghum* genome. The primers were designed to amplify a portion of the putative restorer gene such that a polymorphism was detected between restorers and maintainers. The assay was a plus/minus assay to genotype the mapping population and subsequently map the gene. Primers were designed targeting SNP1616 to selectively amplify a portion of the gene in the restorer lines which would fail to amplify in the maintainer lines.

```
                                       SEQ ID NO: 26
Forward primer for mapping
CATTCCTCCTGATGTCACTATCTTCAG SEQ ID NO: 27
Reverse primer for mapping
TCTCTATTGAACCCTTTTGGCCATC
```

The positions of SEQ ID NO: 26 and SEQ ID NO: 27 are highlighted in SEQ ID NO: 8, although it is not an exact match since SEQ ID NO: 26 and SEQ ID NO: 27 are designed from sequences specific to the restorer genotype and SEQ ID NO: 8 is derived from a maintainer genotype.

FIG. 7 shows the location of sPPR1 gene as mapped to the *Sorghum* genome.

Example 9

Genotyping Germplasm for the Restorer Gene

The Taqman assay was used to genotype various *sorghum* lines as restorers or non-restorers. The Taqman assay requires a forward and reverse primer as well as two probes (fluorescently labeled) which are specific to a SNP or Haplotype. The following Taqman probe and primer sequences were designed to genotype samples for the fertility restorer. SNP 1705 (position 375 in FIG. 5) was the target site for the probe that distinguishes Haplotype 1 versus Haplotype 2. SNP1863, SNP1866 and SNP1867 (positions 532, 535 and 536 in FIG. 5) were the target sites for the probe that distinguishes Haplotype 3 versus Haplotype 2.

For each target site, there is a probe specific for the maintainer genotype and another specific for the restorer genotype. For example, SEQ ID NO: 28 is specific for Haplotype 3 maintainer genotype, SEQ ID NO: 29 is specific for the Haplotype 2 restorer genotype, SEQ ID NO: 32 is specific for Haplotype 1 maintainer genotype and SEQ ID NO: 33 is specific for Haplotype 2 restorer genotype.

(i) *Sorghum* Restorer Gene Assay to Distinguish Haplotype 2 (HAP2) from Haplotype 3 (HAP3)

```
                                       SEQ ID NO: 28
haplotype 3 maintainer specific probe
6 Fam-TCAACATTTGGTTTCAA-MGB SEQ ID NO: 29
probe 2-restorer ( Restorer specific)
haplotype 2 restorer specific probe
VIC-CAACATCAGGATTCAA-MGB Amplicon Primers
                                       SEQ ID NO: 30
Forward primer
GGCGAAGTGATGAAGCTCCTTGATG SEQ ID NO: 31
Reverse primer
AGCAGCTATCAATCAAAGTCTTACAT
amplicon length = 145 bp
```

6 FAM (an isomer of carboxyfluorescein) is a fluorescent dye tagged to Hap3 specific probe at the 5' end and VIC is a florescent dye tagged to Hap2 probe. MGB means minor grove binder. As is known to those skilled in the art, other common dyes can be used, for example, TET (tetrachlorofluorescein). As is known to those skilled in the art, any tag can be used.

Figure 8:
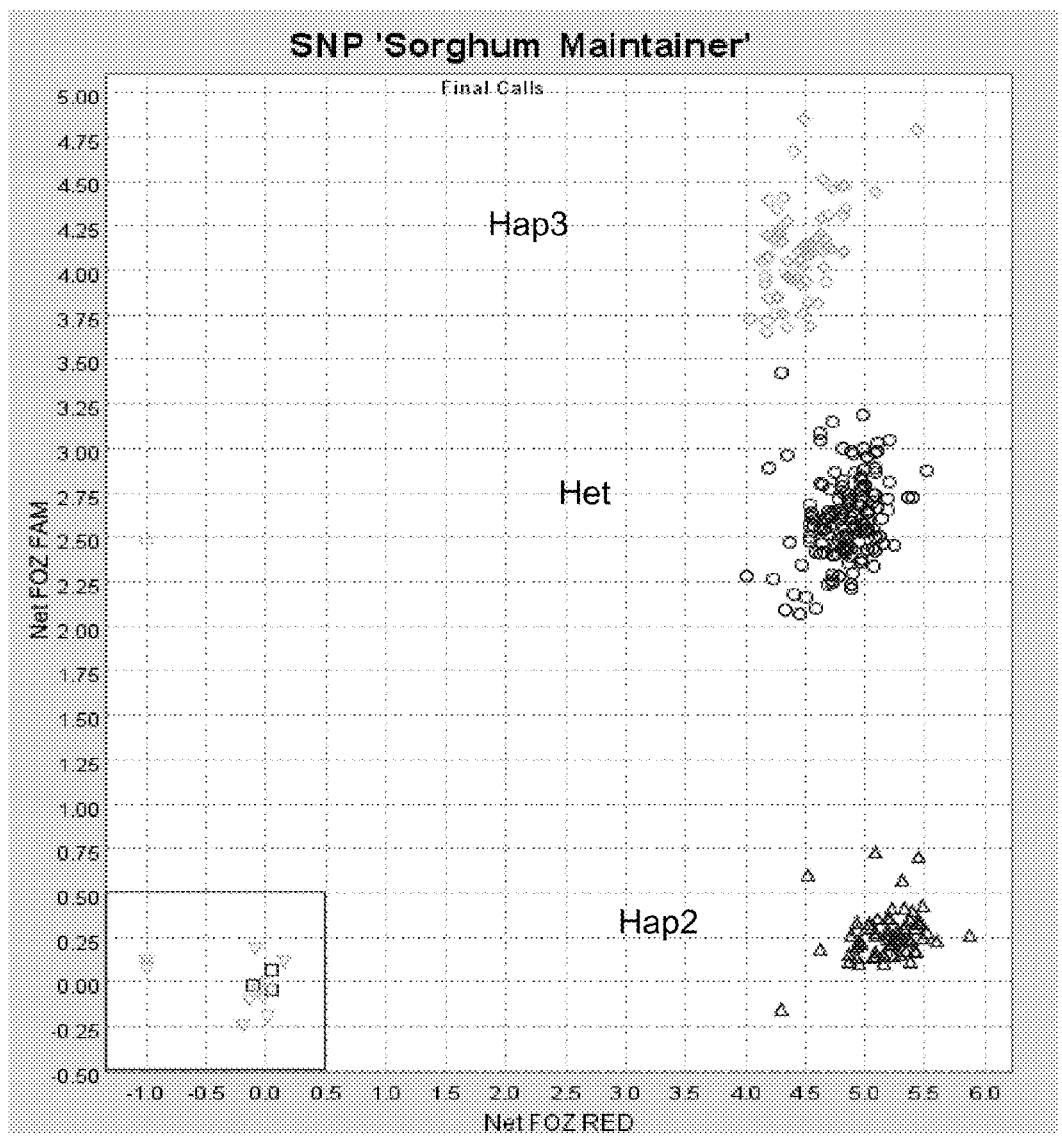
FIG. 8 is an example of the Taqman SNP assay output distinguishing Hap2 from Hap3.

FIG. 8 shows the results of the Taqman analysis. The assay was clearly able to distinguish homozygous Haplotype 2 from homozygous Haplotype 3 lines in an F2 population segregating for the fertility gene. An organism is homozygous for a particular gene when identical alleles of a gene are present on both homologous chromosomes. For this example, a plant homozygous for Haplotype 2 would have two copies of the allele. The assay is also capable of detecting heterozygous lines. An organism is heterozygous for a particular gene when two different alleles of the gene are present on the homologous chromosomes. For this example, a heterozygous plant would have one copy of Haplotype 2 and one copy of Haplotype 3.

(ii) *Sorghum* Restorer Gene Assay to Distinguish Haplotype 1 (HAP1) from Haplotype 2 (HAP2)

```
                                       SEQ ID NO: 32
haplotype 1 maintainer specific probe
6FAM-CAACATcAGGTTTAGC-MGB SEQ ID NO: 33
haplotype 2 restorer specific probe
VIC-CAACATtAGGTTTAGCTC-MGB Amplicon primers
                                       SEQ ID NO: 34
Forward primer
GATAGGCTATTCAAAGAAGGAAAGGTTAC SEQ ID NO: 35
Reverse primer
GGGTTTCAAGCCAATCAAGAGCATC
amplicon length = 182 bp
```

Figure 9:
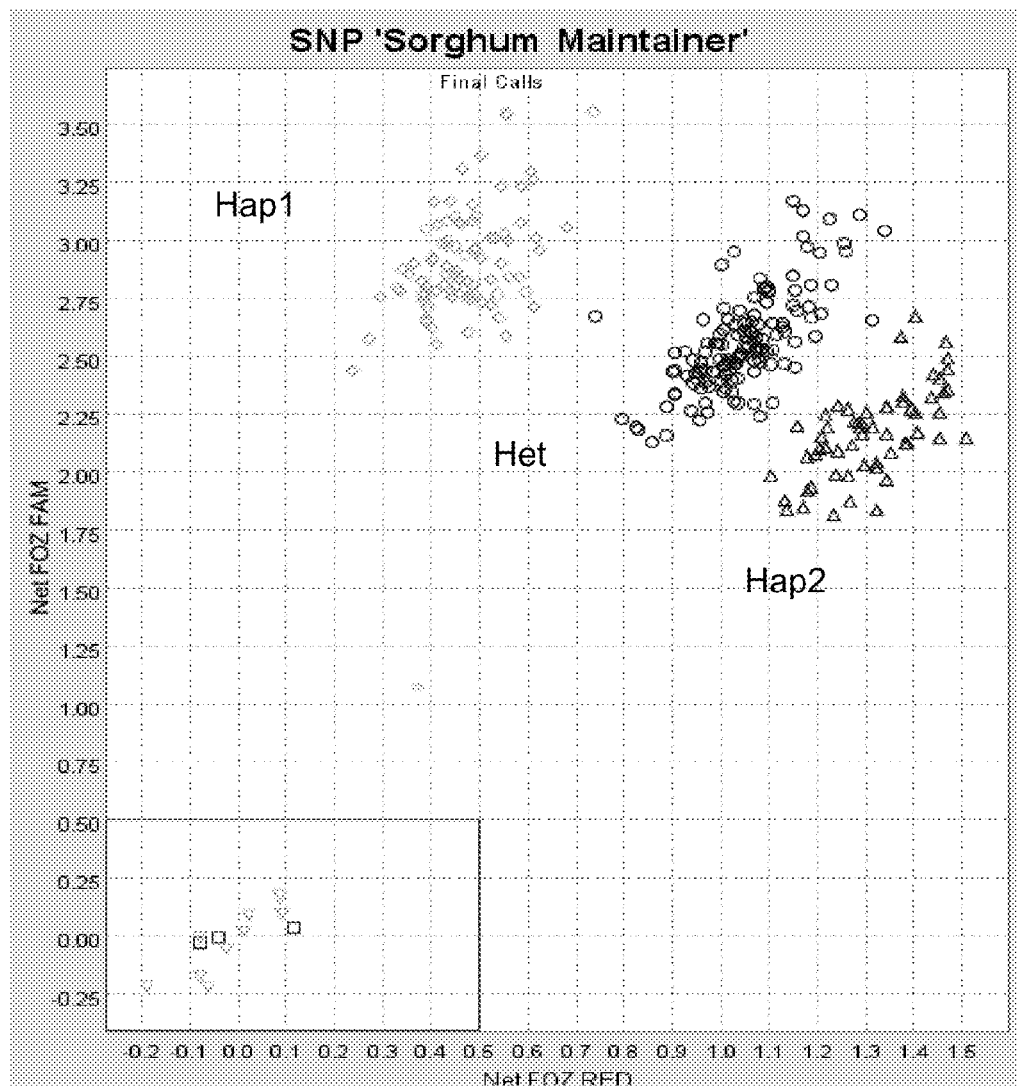
FIG. 9 is an example of the Taqman SNP assay output distinguishing Hap1 from Hap2.

FIG. 9 shows the results of the second Taqman analysis. The assay was clearly able to distinguish homozygous Haplotype 2 lines from homozygous Haplotype 1 lines in an F2 population segregating for the fertility gene (i.e., screening a segregating population from the Maintainer X Restorer crosses that contain homozygous restorer gene (RR), Het (Rr) and non restorer gene (rr) genotypes). For this example, a plant homozygous for Haplotype 2 would have two copies of the allele. For this example, a heterozygous plant would have one copy of Haplotype 1 and one copy of Haplotype 2.

Accordingly, these primers and probes can be used in marker assisted selection (MAS) to differentiate restorers from non-restorers. Table 8 shows the segregation of the marker alleles among F2 plants. As is known to those skilled in the art, with the information and sequences provided (in particular in FIG. 5), other primers and probes can be made and used to differentiate restorers from non-restorers. Those listed above are examples, but it is to be understood that other primers and probes are within the scope of the invention.

While the foregoing invention has been described in some detail for purposes of clarity and understanding, it will be clear to one skilled in the art from a reading of this disclosure that various changes in form and detail can be made without departing from the true scope of the invention. For example, all the techniques, methods, compositions, apparatus and systems described above may be used in various combinations. All publications, patents, patent applications or other documents cited in this application are incorporated by reference in their entirety for all purposes to the same extent as if each individual publication, patent, patent application or other document were individually indicated to be incorporated by reference for all purposes.

LISTING OF SEQUENCES

SEQ ID NO:
SEQ ID NO: 1 Primer for SEQ ID NO: 5
SEQ ID NO: 2 Primer for SEQ ID NO: 5

TABLE 8

Segregation for fertility Taqman marker alleles among F2 plants in thirty-five *sorghum* populations (ns = not significant at P > 0.01 level, * = significant at P < 0.01 level, ** = significant at P < 0.001 level).

| | | | | | Chi-Square (1:2:1 | Evaluation of SNP Fertility Markers in the *Sorghum* Breeding Program | | |
| --- | --- | --- | --- | --- | --- | --- | --- | --- |
| Population | Taqman Assay Type | Maintainer | Heterozygous | Restorer | ratio) | Selections by Breeders | Number that do not match | Success Rate |
| Manhattan, Texas-1 | Hap1 vs Hap2 | 53 | 144 | 69 | 3.74 ns | — | — | — |
| Manhattan, Texas-2 | Hap3 vs Hap2 | 81 | 134 | 57 | 4.29 ns | 30 | 0 | 100% |
| Manhattan, Texas-3 | Hap3 vs Hap2 | 82 | 135 | 56 | 4.99 ns | 8 | 0 | 100 |
| Manhattan, Texas-4 | Hap3 vs Hap2 | 59 | 149 | 63 | 2.81 ns | 10 | 0 | 100 |
| Manhattan, Texas-5 | Hap3 vs Hap2 | 64 | 147 | 63 | 1.47 ns | 18 | 0 | 100 |
| Manhattan, Texas-6 | Hap3 vs Hap2 | 59 | 134 | 77 | 2.41 ns | 16 | 0 | 100 |
| Manhattan, Texas-7 | Hap3 vs Hap2 | 63 | 149 | 62 | 2.11 ns | — | — | — |
| Manhattan, Texas-8 | Hap3 vs Hap2 | 66 | 141 | 61 | 0.92 ns | 12 | 0 | 100 |
| Manhattan, Texas-9 | Hap1 vs Hap2 | 82 | 132 | 59 | 4.17 ns | — | — | na |
| Plainview, Texas-1 | Hap3 vs Hap2 | 62 | 141 | 71 | 0.82 ns | | | |
| Plainview, Texas-2 | Hap3 vs Hap2 | 59 | 140 | 75 | 2.00 ns | | | |
| Plainview, Texas-3 | Hap1 vs Hap2 | 64 | 132 | 69 | 0.19 ns | | | |
| Plainview, Texas-5 | Hap3 vs Hap2 | 70 | 126 | 78 | 2.23 ns | | | |
| Plainview, Texas-6 | Hap3 vs Hap2 | 58 | 143 | 73 | 2.17 ns | | | |
| Plainview, Texas-7 | Hap3 vs Hap2 | 70 | 123 | 80 | 3.40 ns | | | |
| Plainview, Texas-8 | Hap3 vs Hap2 | 70 | 137 | 67 | 0.07 ns | | | |
| Plainview, Texas-9 | Hap1 vs Hap2 | 63 | 132 | 79 | 2.23 ns | | | |
| Plainview, Texas-10 | Hap1 vs Hap2 | 65 | 133 | 76 | 1.12 ns | | | |
| Taft, Texas-1 | Hap3 vs Hap2 | 90 | 135 | 44 | 15.74** | | | |
| Taft, Texas-2 | Hap3 vs Hap2 | 64 | 129 | 78 | 2.07 ns | | | |
| Taft, Texas-3 | Hap3 vs Hap2 | 66 | 134 | 69 | 0.07 ns | | | |
| Taft, Texas-4 | Hap3 vs Hap2 | 71 | 123 | 73 | 1.68 ns | | | |
| Taft, Texas-5 | Hap1 vs Hap2 | 72 | 116 | 74 | 3.47 ns | | | |
| Taft, Texas-6 | Hap1 vs Hap2 | 68 | 129 | 67 | 0.14 ns | | | |
| Taft, Texas-7 | Hap3 vs Hap2 | 64 | 107 | 102 | 23.33** | | | |
| Taft, Texas-8 | Hap3 vs Hap2 | 78 | 116 | 80 | 6.47 ns | | | |
| Taft, Texas-9 | Hap3 vs Hap2 | 61 | 140 | 72 | 1.07 ns | | | |
| Puerto Vallarta, Mexico-1 | Hap3 vs Hap2 | 83 | 224 | 24 | 62.39** | | | |
| Puerto Vallarta, Mexico-2 | Hap3 vs Hap2 | 76 | 173 | 86 | 0.96 ns | | | |
| Puerto Vallarta, Mexico-3 | Hap3 vs Hap2 | 106 | 188 | 62 | 12.00* | | | |
| Puerto Vallarta, Mexico-4 | Hap3 vs Hap2 | 68 | 168 | 127 | 21.19** | | | |
| Puerto Vallarta, Mexico-5 | Hap3 vs Hap2 | 56 | 138 | 116 | 26.95** | | | |
| Puerto Vallarta, Mexico-6 | Hap3 vs Hap2 | 59 | 187 | 120 | 20.51** | | | |
| Puerto Vallarta, Mexico-7 | Hap3 vs Hap2 | 66 | 174 | 91 | 4.65 ns | | | |
| Puerto Vallarta, Mexico-8 | Hap3 vs Hap2 | 61 | 172 | 116 | 17.41** | | | |

SEQ ID NO: 3 Primer for SEQ ID NO: 6
SEQ ID NO: 4 Primer for SEQ ID NO: 6
SEQ ID NO: 5 TS0304T partial
SEQ ID NO: 6 TS050
SEQ ID NO: 7 sPPR1 ORF
SEQ ID NO: 8 sPPR1 genomic
SEQ ID NO: 9 sPPR2 ORF
SEQ ID NO: 10 sPPR2 genomic
SEQ ID NO: 11 sPPR3 ORF
SEQ ID NO: 12 sPPR3 genomic
SEQ ID NO: 13 sPPR4 ORF
SEQ ID NO: 14 sPPR4 genomic
SEQ ID NO: 15 sPPR5 ORF
SEQ ID NO: 16 sPPR5 genomic
SEQ ID NO: 17 sPPR1 peptide
SEQ ID NO: 18 sPPR2 peptide
SEQ ID NO: 19 sPPR3 peptide
SEQ ID NO: 20 sPPR4 peptide
SEQ ID NO: 21 sPPR5 peptide
SEQ ID NO: 22 HAP 1
SEQ ID NO: 23 HAP 2
SEQ ID NO: 24 HAP 3
SEQ ID NO: 25 HAP 4
SEQ ID NO: 26 Primer to map sPPR1
SEQ ID NO: 27 Primer to map sPPR1
SEQ ID NO: 28 Hap3 probe
SEQ ID NO: 29 Hap 2 probe
SEQ ID NO: 30 amplicon primer
SEQ ID NO: 31 amplicon primer
SEQ ID NO: 32 Hap 1 probe
SEQ ID NO: 33 Hap 2 probe
SEQ ID NO: 34 amplicon primer
SEQ ID NO: 35 amplicon primer
SEQ ID NOs: 36-76 (see, Table 1)

What is claimed is:

1. A method of identifying a *sorghum* restorer plant by identifying an allele associated with a restorer gene, the method comprising:
   (a) detecting at least one nucleic acid from the *sorghum*, wherein the nucleic acid localizes to a chromosome interval flanked on each side by the marker pair of TS304T and TS050 as set out in SEQ ID NO: 5 and SEQ ID NO: 6 respectively; and
   (b) identifying the *sorghum* comprising the nucleic acid, thereby identifying the *sorghum* restorer plant.

2. The method of claim 1 wherein the *sorghum* is a whole plant, a plant organ, a plant seed or a plant cell.

* * * * *

SEQUENCE LISTING

<160> NUMBER OF SEQ ID NOS: 76

<210> SEQ ID NO 1
<211> LENGTH: 18
<212> TYPE: DNA
<213> ORGANISM: Artificial Sequence
<220> FEATURE:
<223> OTHER INFORMATION: primer

<400> SEQUENCE: 1
acataaaagc ccctcttc                                            18

<210> SEQ ID NO 2
<211> LENGTH: 19
<212> TYPE: DNA
<213> ORGANISM: Artificial Sequence
<220> FEATURE:
<223> OTHER INFORMATION: primer

<400> SEQUENCE: 2
ctttcacacc ctttattca                                           19

<210> SEQ ID NO 3
<211> LENGTH: 22
<212> TYPE: DNA
<213> ORGANISM: Artificial Sequence
<220> FEATURE:
<223> OTHER INFORMATION: primer

<400> SEQUENCE: 3
tcgtggattt gcattccttg aa                                       22

<210> SEQ ID NO 4
<211> LENGTH: 22
<212> TYPE: DNA
<213> ORGANISM: Artificial Sequence
<220> FEATURE:
<223> OTHER INFORMATION: primer

<400> SEQUENCE: 4
gaatgtgcct tgtttctgtg cg                                       22

<210> SEQ ID NO 5
<211> LENGTH: 280
<212> TYPE: DNA
<213> ORGANISM: Sorghum bicolor

<400> SEQUENCE: 5

```
tcttcttctt cttcttcttc ttcttcttct tcttcttctt cttcttcttc ttcttcttct    60
tcttcttctt cttcttcttc ttcttcttct tcttcttctt cttcttcttc tgtcaagctg   120
atgaatcacc ataggtggaa gctacaaggg agctcatgca gtaaaccaag agcgagtcaa   180
atactgagtt aaccaggact gcccttccca ttggattgag gaggttggcc tgccatgagc   240
tgatataccg gtctgtcttt tgaataaagg gtgtgaaaga                          280
```

<210> SEQ ID NO 6
<211> LENGTH: 682
<212> TYPE: DNA
<213> ORGANISM: Sorghum bicolor
<220> FEATURE:
<221> NAME/KEY: misc_feature
<222> LOCATION: 403, 427, 473, 476, 517, 550, 566, 628, 647, 660, 663, 668
<223> OTHER INFORMATION: n = A,T,C or G

<400> SEQUENCE: 6

```
ggcaagtcgg ccgagctcga attcgtcgac tcgagggatc atgaaactac tactcaaaat    60
tggagttgag aacattgatg ttgttaccct tctggctgac tctaataatc caggatataa   120
tcgtggattt gcattccttg aactggagac ttataaagat gcacagatag catacaaaaa   180
gctttcaagg aaagatgttt ttggcaaggg tttaaatata acagttgcat gggccgaacc   240
attgaatggt cgagatgaaa aacagatgca gaaggtctct ctctctctct ctctctctct   300
ctcacacaca cacacacaca ccacacgcac gcacagaaac aaggcacatt catggacgaa   360
cacatacata ggctgtttgt gatctaatga agctgaatat tcntcgcaat gcttgcatat   420
agattanccc tttgcacgtg caggggaaca caacaatcaa gaggaattag cangcnatgt   480
tttttgaaat ctgcaaccaa tttacctgca cctacanagt acaattgtgc tgactccagg   540
gctaaagccn ccatattaca tgcgantggc agccggtatt ttttgtgata atagtggcaa   600
aatgagaagc tagatccggg ccctctanat gccgccgcct gcataancttt gaattttctn   660
tantgtcncc taaatcgctt gg                                            682
```

<210> SEQ ID NO 7
<211> LENGTH: 5079
<212> TYPE: DNA
<213> ORGANISM: Sorghum bicolor

<400> SEQUENCE: 7

```
atgtcgaccc gggcgcggcc cgcttggttg aacaagctaa agcggatcat tggacggcgc    60
atccgctcgg gaagcctcag tgctgaggcc gcgcgccaac tctgcgacga ggtgctccca   120
tcgatccaaa gtcgttcccc accaccggcc gcttcagcag ccgcgcgccg gtggagggcc   180
gaccgccgcc cttcctggga gctggagcag ttcatcggac agtgttaccg ctcgggtgac   240
ctcgcccccg aggacgcagt cgatctgttc gacgaattgc ttcaccaagc gaggcccggc   300
tccatttacg ccctcaacca gctgctcacc acggtcgctc gcgccccggt ctcctccact   360
gtgcgcgatg gccctgctcg cgccgtgtcc atgttcaacc gtatggcccg agcgggcgcc   420
aagaaggtgg ctccagacat agctaccttc ggcatcctca tcagctgctg ttgcaacgcg   480
ggctgtttga acctcggctt cgctgcattg ggccaaatca ttaagacggg agtgagggca   540
catgccgtca ccttcacgcc cctgctcagg accctctgcg ccgagaagag gacaagcgat   600
gcaatgaata ttgtgctcag gcggatgcct gagctcggct gcaccccga tgtcttctcc   660
```

```
tacaccacac ttctcaaagg gctttgtgct gagaagaaat gtgaagaggc tgccgagctg    720
atccacatga tggctgaaga tggagacaac tgcccaccta atgtggtgtc ctatagcact    780
gtaatccatg gattctttaa agagggagag gtagggaaag cttacaccct gttttgcaaa    840
atgcttgatc atgggatccc gccagatgtt gtgacctgca attcagtcat tgatggccta    900
tgcaaggctc aagcaatgga caaggccgag gaggtccttc agcagatgat tgacgaacat    960
attatgcctg attgtactac atataacagt ctgatccatg gatacctctc tctgggacag   1020
tggaaagagg cagtccaaat tctcaaagaa atgtctagag atgggcaggg gccaaatgtt   1080
gttacttaca gtatgctgat aaactgtctt tgtaaatctg gattgcgcgc agaagctaga   1140
gagatcttta attctatgat tcagagtggt caaaaaccca atgccgccac ttatcgaagt   1200
ctgcttcatg ggtatgctac cgaaggcaat cttgttgata tgaacaatgt caaagatcta   1260
atggtacaaa atggaatgcg acctgaccgt catgtcttca acatagaaat ctatgcatac   1320
tgtaaatgtg gaaggctaga tgaggcaagc cttacttttta acaaaatgca gcagctagga   1380
ttcatgccag acatagtcac ctacaccacg gttatagatg ggctttgcaa gataggccgg   1440
ctggacgatg caatgtcccg attctgtcag atgattgatg atggattgtc tcccaatatc   1500
ataacattta cgaccctgat tcatgggttt tctatgtatg gcaaatggga gaaggctgag   1560
gaactatttt atgagatgat ggatagaggc attcctccta atgtcaatac gttcaattca   1620
atgatagata ggctattcaa agaaggaaag gttacggagg cccgaaaact ctttgatttg   1680
atgccacgtg caggagctaa acctaatgtt gtttcttata atacaatgat tcatgggtat   1740
ttcatagctg gtgaagtggg cgaagtgatg aagctccttg atgatatgct cttgattggc   1800
ttgaaaccca atgctgttaa ccttaatact ttacttgatg gcatgctctc tattggcttg   1860
aaaccaaatg ttgacacatg taagactttg attgatagct gctgtgaaga tgacaggata   1920
gaggatatat taactctgtt ccgagaaatg ttgagcaagg ctgataagac tgacactatc   1980
acggaaaata taaaactcaa atgcatgaaa aaaaaaaaca aggtatggtt gaacaagctg   2040
aagcggatca ttggacggcg catccgctcg ggaagcctca gcgctgaggc cgcgcgccaa   2100
ctctgcgacg atgtgatcca aaggcgtccc ccaccgccgg ccgtttccgc agccgcgcgc   2160
tggcattggg acgaccaccg cccttcctgg gagctggagc gcttcatcgg agtctgttac   2220
cgctcgggag accttggccc cgaggacgca ctcggtctgt tcgacgagtt gcttctccaa   2280
gcgaggcccg gctccgttta cgccctcaac cagctcccca ccaccatcgc tcacgccccg   2340
gtctcctcca ccgtgacgga cggccctgcg ctcgccgtgt ccctgtttat ccgcatggcc   2400
cgagctggcg ccaagaaggt ggctccaaac atagcgacgt acaacatcgt catcagctgc   2460
tgctgtcatg caggatgctt gaacctcagc ttcgctgcat tgcgccaaat cattaagaca   2520
gggctgagga cagatgccat gatcttcacg cccatgctca ggaccctctg tgccgaaaag   2580
aggacgagtg atgcaatgga tattgtggtc cgacggatgc tgagctctg ctccaccccc   2640
aatgtcttct cctacaacac tcttctcgag gggctctgtg atgagaagaa atgtgatgag   2700
gctgtggagc tgatccacat gatggctgag gatggagata actgcccacc taatgtggtg   2760
tcttatacca tcgtaatcca tgggttgttt aaagagcatg aggtggggaa agctttcacc   2820
ctgttttgtg aaatgcttcg tcgtgggatc ccgccagatg ttatgattta cagatcaatc   2880
atcgatgtcc tatgcaaggt tcaagcaatg gacaaggccg agaaggtctt tcgacagatg   2940
cttgacaatc atattatgcc tgactgcact acatatacta gtcttctcca tggataccto   3000
tctttgggac agtggaaaga agcagtcaga attctcaaag aaatgtccag agatgggcaa   3060
```

```
cgacccgatg ttgttacata cagtatgctg ataaactgcc tttgtaaatc tggagggcac    3120
gcagaagcta gagagatttt taattctatg atccagaacg gtgaaaaacc caatgtcagc    3180
acctatggaa gtatgcttca tgggtatgct accaaaggag atcttgttga aatgaataat    3240
cttttagatt tgatggtaca gaatggagtg caacctaatc atcatatctt caacatacag    3300
atctatgcac actgtaaatg cggaaggtta gatgaggcaa tgcttacttt taacaaaatg    3360
cggcagcaag gattggtgcc agacattgtc agctatggga cggtaataga tgcgctttgc    3420
aggataagcc ggctggacga tgcaatggtc caattctatc agatgattga ttatggattg    3480
tctcccaata tcatagtatt tacgactcta attcatggtt tttctatgca tggcaaatgg    3540
gggaaggctg aggaactatt ttatgagatg atggatagtg gcattcgtcc taccgtcgtt    3600
gtcttcgttg caatgataga caagctattc aaagaaggaa aggttacaga ggcccaaaaa    3660
ctctttgatt tgatgccata tgtaggtgta aagcctgatg tagtttccta tagtacaatg    3720
attcatgggt gcttcttaac tggtaaacca gacgaagtga tgaagctcct tgatgatatg    3780
ctcttgattg gcttgaaacc caatgctgtt aaccttaata ctttacttga tggcatgctc    3840
tctattggct tgaaaccaaa tgttgctacc ttctggagaa gttacaatat agtttcttat    3900
ctacccagta gtatgtatct ggctaatact gatcgcatct tttgcatgaa cctcaggtat    3960
gaacagcttg aattggaagg gaaattattg gaggcatgtc ctcctaattt gagtgtcatt    4020
ttcaggagca gaggtgactt ggattttgct tttgaaagta tttcagcctt ctcagacaat    4080
ggggagaatc aggggtatat tttcctgctg gaaagtgttg aaaacatcag tggctcaaag    4140
cttgccgtta gagtgcaatg gggaaagaag ttgatgtcta ctgatgaaga atcagattgt    4200
gtagttatat gtccacctaa cagaaattct gatcatgagg aagttaatcc ttatgctatg    4260
aactcacata tggacaccaa cggcctggaa gatgtgtctg taaacccaga cctgctcaag    4320
ctgattcatc agcaggagtc ttctgtcacg aattccaccag caaaaccagt agctagacag    4380
caagggtcta gccatactgt ccctgagcca tgcactgttg cacctgatag aaggtcatct    4440
agagcaggaa attgtgctcc aattcctcat cccaccagca gcggggaaaa aaactcggat    4500
aatagtagct cctcacaaag aagcatggca aagaaggtgt ggcaaactga actgacttcc    4560
attgtctttt cgtgtggtat atgtacaaac tatcctggcc ttggtttgct ggaacatctg    4620
gaaggcaagg aatgcgaaaa tcttcaggaa ccaaactcaa acggaagagc tggaaaaact    4680
aagaagacaa ctgttgctgt tgcacctaca tttgtctgtg ctaattgtgc taagaagaga    4740
ggagagtttt acacaaaatt agaagaaaag cgcaaggctt tggaagagga gaagctccaa    4800
gcagaggcca gaaagagggt tttggaaacg atcagtacag caattttttat tatttccatc    4860
ttgcttggtg cctccaactc gtgccaagtc accaaaatta acacagacaa agagctgtgc    4920
agtgacaccc ctcagcaaag ggaggaaatg gcagtgcagt atgctgccag ttgcattatc    4980
acaacattgg gaactccaaa gatgttagca gcaaggcaca atgttctcca aagagggctt    5040
caaagactgg atcagctact aaatccaggg aagacctga                           5079
```

<210> SEQ ID NO 8  
<211> LENGTH: 15426  
<212> TYPE: DNA  
<213> ORGANISM: Sorghum bicolor

<400> SEQUENCE: 8

```
gcataaaaac gagagtgggt gttttgcagg atgtgagtaa ctatatcaac atgagtagca       60
```

```
gcataaagtt gaggactgtt taactgaagc ctaaacttcc attgtcgtac taaatgaaat      120
attaatctat ataaatatga aaagatagtc aaatgtttta catttcatca tggttggctt      180
ctatatcatt ttcttcgttc tccggttcac tatgaacttc ttgttcaaat tttagccccc      240
gttgacaatt ttttagcta  tataagtcta ttagacctaa gtattatttt ttgggccaga      300
gccagaccaa aaattgccgg ttattttagg taaaaaaagc atgtccacga ccatcccatg      360
gatcagatcg gtactttccg ggctaggccc gggcttgggc gggttgctcg ttggttttta      420
gtggaaaggt aaataaaaga aatacttcgg gctaaacttg gctcgagaaa attttttctgg     480 acaattagac tcaaggggtg tttagctctt cttttatccc aaaaaatttt aggtttggtc      540
tatcacttta cataacaaaa ttaaatacca tgcaaaattt ttggtaaaaa agtggatagt      600
ctccatttta gattttggtc tcaaaaaaag atcaaaagag ccttaagtgg ccctaatgag      660
gtaattggta ttttagatgg aactaaacat gatcttaaaa aaattggtat tttatatttt      720
atcattaaag taattgatat tttgtatttt ttattctata ggaactcaac acaccctaag      780
gttaatggac ggcctaaaac tcggtaagct cagacccagt tcaatttgct cgtgtctacg      840
gtgaaaatta tttggcgctc aaactaattt tcttttgtaa agaaaagaaa caccagaatt      900
actcggtcaa acataggcct tgtttagttc caaaatattt tacaaaatcg gcactgtagc      960
tctttcgttt gtatttgaca atattgtcc  aattatgaac taactagact caaaagattc      1020
atctcgtcaa tttcgaccaa actgtgcaat tagtttttat ttttgtttat atttaatact      1080
tcatgcatgt gtctaaagat ttgatgtgac ggaaaatctg aaaaattttg taaaatttt      1140 tggtaactaa acaaggccat agagaaacga ttccactacc aagcccccaag cacgtgatga     1200 gtcctctcct ctagctcggt tagcacgtga tcagtcctct tctctagctc tcggcttgac     1260
gcgaatcacg cccaccgttt ctttcgaatc gaaaaaaaaa gacccagagg ccagagctca     1320
cgcgcaggcg caggcgcagg cgcagcggaa ccccgatccc aatctcccac accaccggta     1380
cagagtacac cgccgccgct ctgtgcctgt gcggaccgtc cccattccca gcgcgagcga     1440
gctgtgagca gcatttccca ccgaacccga ggggcgaggt gtggatccca ccggcggcgc     1500
cgaccatgtc gacccgggcg cggcccgctt ggttgaacaa gctaaagcgg atcattggac     1560
ggcgcatccg ctcgggaagc ctcagtgctg aggccgcgcg ccaactctgc gacgaggtgc     1620
tcccatcgat ccaaagtcgt tccccaccac cggccgcttc agcagccgcg cgccggtgga     1680
gggccgaccg ccgcccttcc tgggagctgg agcagttcat cggacagtgt taccgctcgg     1740
gtgacctcgc ccccgaggac gcagtcgatc tgttcgacga attgcttcac caagcgaggc     1800
ccggctccat ttacgccctc aaccagctgc tcaccacggt cgctcgcgcc ccggtctcct     1860
ccactgtgcg cgatggccct gctcgcgccg tgtccatgtt caaccgtatg gcccgagcgg     1920
gcgccaagaa ggtggctcca gacatagcta ccttcggcat cctcatcagc tgctgttgca     1980
acgcgggctg tttgaacctc ggcttcgctg cattgggcca aatcattaag acgggagtga     2040
gggcacatgc cgtcaccttc acgcccctgc tcaggaccct ctgcgccgag aagaggacaa     2100
gcgatgcaat gaatattgtg ctcaggcgga tgcctgagct cggctgcacc cccgatgtct     2160
tctcctacac cacacttctc aaagggcttt gtgctgagaa gaaatgtgaa gaggctgccg     2220
agctgatcca catgatggct gaagatggag acaactgccc acctaatgtg gtgtcctata     2280
gcactgtaat ccatggattc tttaaagagg gagaggtagg gaaagcttac accctgtttt     2340
gcaaaatgct tgatcatggg atcccgccag atgttgtgac ctgcaattca gtcattgatg     2400
gcctatgcaa ggctcaagca atggacaagg ccgaggaggt ccttcagcag atgattgacg     2460
```

```
aacatattat gcctgattgt actacatata acagtctgat ccatggatac ctctctctgg    2520
gacagtggaa agaggcagtc caaattctca aagaaatgtc tagagatggg caggggccaa    2580
atgttgttac ttacagtatg ctgataaact gtctttgtaa atctggattg cgcgcagaag    2640
ctagagagat ctttaattct atgattcaga gtggtcaaaa acccaatgcc gccacttatc    2700
gaagtctgct tcatgggtat gctaccgaag gcaatcttgt tgatatgaac aatgtcaaag    2760
atctaatggt acaaaatgga atgcgacctg accgtcatgt cttcaacata gaaatctatg    2820
catactgtaa atgtggaagg ctagatgagg caagccttac ttttaacaaa atgcagcagc    2880
taggattcat gccagacata gtcacctaca ccacggttat agatgggctt tgcaagatag    2940
gccggctgga cgatgcaatg tcccgattct gtcagatgat tgatgatgga ttgtctccca    3000
atatcataac atttacgacc ctgattcatg gttttctat gtatggcaaa tgggagaagg     3060
ctgaggaact attttatgag atgatggata gaggcattcc tcctaatgtc aatacgttca    3120
attcaatgat agataggcta ttcaaagaag gaaaggttac ggaggcccga aaactctttg    3180
atttgatgcc acgtgcagga gctaaaccta atgttgtttc ttataataca atgattcatg    3240
ggtatttcat agctggtgaa gtgggcgaag tgatgaagct ccttgatgat atgctcttga    3300
ttggcttgaa acccaatgct gttaacctta atactttact tgatggcatg ctctctattg    3360
gcttgaaacc aaatgttgac acatgtaaga ctttgattga tagctgctgt gaagatgaca    3420
ggatagagga tatattaact ctgttccgag aaatgttgag caaggctgat aagactgaca    3480
ctatcacgga aaatataaaa ctgtgagtgt cacttcagaa tcgacggact gccattggga    3540
tggaactcaa gctgcagatg gccaaaaggg ttcaatagag aacagagtct taaccttaac    3600
taggacgtgt tatgttgtgc ttagttgtac ttgaagatga tttggaagtg ttgttaaggt    3660
acggtttgtt atctaccttg gagtattttt atggtagatc ttcttgtctt cgtaaatttt    3720
agtgttgcga attttgcaag tttgatattt tctgaaggat attttatgag ggtctccttt    3780
caatataagg gtcatcttta tatctgcctg catgcttagg cattattta gagcaatagc     3840 atttatgttt gcgaagaaac tttatttcg tttttctact cttgaggagt acaagaagac     3900
ctggtactga gtctcatgat gaagtctact gattttaaaa cttgtgtaga cccagtgtaa    3960
ctgtgaaagc ttgttgtaag ctccttatca ctgttccaag gactagttat taaatacaat    4020
atacaaggtg atcttcctca ggttccaaga attagttata gctaaagca agccagtgaa     4080 agcatacca agatgaacag aggaaatagt tgccgacaac tcatggtctg gccactgtca    4140
aaaaagacta acaagcaagc taactgtcgc cattatagca tctgtgcact gctttgtgag    4200
attttgaata gtgtgccaac tagcatgctg aagctgatta tagccagctc ccgatgctac    4260
aacttaacca aaagtgaggt gatcacccct caccagcgat aaatccccat cttccttctc    4320
tacattgctg ctcatggaag gaaccttcgg tattgcttgc tcctgagagg cctacatgat    4380
gtgcttgtgc ttcctcaaag aactcttcga attcaagatt gtgccttcag actgttcccc    4440
tgcatcgata ccatttcttt ctgtccagag catccacgga acatgtttgc atgtctccag    4500
ccccagaggc ctacatgatg tgcttgtgct ttctgaaaga actccaggaa ttcagaaatg    4560
tgccttcatt cagactgttc ccctgcattg ccggcatttc tttctttcta gagcatccat    4620
aatgtatata ttagcaaaag atattatact gagaaacgtt tgcatctgca ttctttaaag    4680
tctacaaaac cttattgcag actagcagat gctagacatt tgcatttgct caaatgtttg    4740
gctagacact gagaaagaga actgaatggc tgggactgcc ttaatgtgaa tatgttgatt    4800
```

```
agcttttaga gttatatgta accgccagag caatcgtgac acattaacca tgtgttacat    4860
tattattcca tccttcggta taatagctta cagctcgcat gtccgtgcag caaatgcatg    4920
aaaaaaaaaa acaaggtatg gttgaacaag ctgaagcgga tcattggacg gcgcatccgc    4980
tcgggaagcc tcagcgctga ggccgcgcgc caactctgcg acgatgtgat ccaaaggcgt    5040
cccccaccgc cggccgtttc cgcagccgcg cgctggcatt gggacgacca ccgcccttcc    5100
tgggagctgg agcgcttcat cggagtctgt taccgctcgg gagaccttgg ccccgaggac    5160
gcactcggtc tgttcgacga gttgcttctc caagcgaggc ccggctccgt ttacgccctc    5220
aaccagctcc ccaccaccat cgctcacgcc ccggtctcct ccaccgtgga cgacggccct    5280
gcgctcgccg tgtccctgtt tatccgcatg gcccgagctg cgccaagaa ggtggctcca     5340 aacatagcga cgtacaacat cgtcatcagc tgctgctgtc atgcaggatg cttgaacctc    5400
agcttcgctg cattgcgcca aatcattaag acagggctga ggacagatgc catgatcttc    5460
acgcccatgc tcaggaccct ctgtgccgaa aagaggacga gtgatgcaat ggatattgtg    5520
gtccgacgga tgcctgagct ctgctccacc cccaatgtct tctcctacaa cactcttctc    5580
gaggggctct gtgatgagaa gaaatgtgat gaggctgtgg agctgatcca catgatggct    5640
gaggatggag ataactgccc acctaatgtg gtgtcttata ccatcgtaat ccatgggttg    5700
tttaaagagc atgaggtggg gaaagctttc accctgtttt gtgaaatgct tcgtcgtggg    5760
atcccgccag atgttatgat ttacagatca atcatcgatg tcctatgcaa ggttcaagca    5820
atggacaagg ccgagaaggt ctttcgacag atgcttgaca atcatattat gcctgactgc    5880
actacatata ctagtcttct ccatggatac ctctctcttgg gacagtggaa agaagcagtc    5940
agaattctca agaaatgtc cagagatggg caacgacccg atgttgttac atacagtatg     6000
ctgataaact gcctttgtaa atctggaggg cacgcagaag ctagagagat ttttaattct    6060
atgatccaga acggtgaaaa acccaatgtc agcacctatg gaagtatgct tcatgggtat    6120
gctaccaaag gagatcttgt tgaaatgaat aatcttttag atttgatggt acagaatgga    6180
gtgcaaccta atcatcatat cttcaacata cagatctatg cacactgtaa atgcggaagg    6240
ttagatgagg caatgcttac ttttaacaaa atgcggcagc aaggattggt gccagacatt    6300
gtcagctatg ggacggtaat agatgcgctt tgcaggataa gccggctgga cgatgcaatg    6360
gtccaattct atcagatgat tgattatgga ttgtctccca atatcatagt atttacgact    6420
ctaattcatg gttttctat gcatggcaaa tgggggaagg ctgaggaact attttatgag     6480
atgatggata gtggcattcg tcctaccgtc gttgtcttcg ttgcaatgat agacaagcta    6540
ttcaaagaag gaaaggttac agaggcccaa aaactctttg atttgatgcc atatgtaggt    6600
gtaaagcctg atgtagtttc ctatagtaca atgattcatg ggtgcttctt aactggtaaa    6660
ccagacgaag tgatgaagct ccttgatgat atgctcttga ttggcttgaa acccaatgct    6720
gttaacctta atactttact tgatggcatg ctctctattg gcttgaaacc aaatgttgct    6780
acctgtaaga ctttgattga tagctgctgt gaagacggca ggatagatga tgtattaact    6840
ctgttcagag aaatgttgag caaggcagct aagactgaca ctgtcgcgga aaagataatt    6900
tcatgaatgt tatttcagat tggaagtact gccattaaga tggaactcaa ctgaagatga    6960
ccaaaagggg aaaataggtt cttaatattg actaagacac attatgttgt gcttaatttt    7020
acatgaagat gatttggatg tgcatcagtc tggagaagtt acaatatagt ttcttatcta    7080
cccagtagta tgtatctggt aggtcttctt gtcgttgtaa attttagtgt ttggttattg    7140
caagctcgat ctcttgtgaa gtatatgtat gaggggattc cttgcagtaa tggtcatcat    7200
```

```
ctatgccctt agccttttt ttagaacagt agcctcggtt tgtttgctga agaaactgtt    7260
tttttcgtct atcaactctt gaggacttga agacctgtac cttattctta cgatgaagtc    7320
agctgatttt agaacatgtg tattatgcct cttgtcactg tttccgctca aagcttcaga    7380
agttgttaca ccagcaggag tcagttcata catttgaggt agcatgtcta caagatgctt    7440
acaacacaag taattaattc aatatgaaag tgatcttcct gaggttccaa gagctagttc    7500
aaggcttaaa gcaagccaat gaacatacta taggctacaa catgatgaca agacattgat    7560
gagcagagtt gcgtgcgcaa atttgaatga aaacatcttt tccactattg aattgtcgtt    7620
gttttgtttg taatggctct caggctaata ctgatcgcat cttttgcatg aacctcaggt    7680
atgaacagct tgaattggaa gggaaattat tggaggtatg aaattttttgg tttcattttt   7740
gagttattca ttcataagat tgtgaattac atgtaatggc tagcaggctt tgttaaacca    7800
ttgtagacac tgacatctgt ctactgcttt tgtttagctg aaattgctat cattataaaa    7860
tgagaggcat gtcctcctaa tttgagtgtc attttcagga gcagaggtga cttggatttt    7920
gcttttgaaa gtatttcagc cttctcagac aatggggaga atcaggggta tattttcctg    7980
ctggaaagtg ttgaaaacat caggtaggct gtctcattcc ttacagcaac tgacgagcta    8040
gtattctgtt ttattagagc tgcacttccc ttacaaccct tgcaaagctg ataaaattcc    8100
cccttttttca atattatagg aacttgttcc gttctactct ggtttggtca ttttcttttt   8160
tctggagttt tgcctgcatg tttatgttat ttatatgcac ctcctcattt cttttggcaa    8220
atgatctaca ctgacttgtt acctaagttt ctaagatgct aactaaggca tcatttgagt    8280
atttgactct aacattgtga ttctgtctcc taagaagatt tctcctcaaa cattattagt    8340
ctgaccttac ctggaaatct gacagtttag tgggtcatgc actaatgcga ctaggttcct    8400
tcaatcttga gctgatgctt atcctgttaa cagtttgttt tgatctctcc attttttggat  8460
tattttttt cttttagtgg ctcaaagctt gccgttagag gtgaaatttc tgaattggaa    8520
aagacagctt gcttctctgg agtggaagct tgatgtactt acaccacaag ctgccaccat    8580
tacccaggga aagaagtctt gctcgtgtgc gaatacaagt taattagtaa ttagttgtta    8640
ttttcttggt tataaacaat tgatgggagc gccatgttat agtcctgttt gactctatga    8700
ttggctcttc aaggctccat ctgattatgc agtacacaaa tatttatata tgtttttta    8760
atgaaaaatg cagtgcaatg gggaagaag ttgatgtcta ctgatgaaga atcagattgt     8820
gtagttatat gtccacctaa cagaaattct gatcatgagg aagttgtgag ttgcagccat    8880
gatgagattc ttcaggaagg caacagaatc cttatgctat gaactcacat atggacacca    8940
acggcctgga agatgtgtct gtaaacccag acctgctcaa gctgattcat cagcaggagt    9000
cttctgtcac gaattcacca gcaaaccag tagctagaca gcaagggtct agccatactg      9060
tccctgagcc atgcactgtt gcacctgata gaaggtcatc tagagcagga aattgtgctc     9120
caattcctca tcccaccagc agcggggaaa aaaactcgga taatagtagc tcctcacaaa     9180
gaagcatggc aaagaaggtc cggtaatcat ctgtaccctc ctttgaactg taccatttgg     9240
gcttcatcta ctttctttg tttctcagac tgtcttctat ttgtcttatg ctgccaaatt    9300
aactttggac atgaagagga tgttggccct cgatcttacc cacacaatca tacacgcact   9360
cggctgaagg ttgaggaagg ggtgaggaca gagcagacac acgcacagca cagcacgaac    9420
acagcagctc tgctgcttca gaggtgtggc aaactgaact gacttccatt gtctttcgt    9480
gtggtatatg tacaaactat cctggccttg gtttgctgga acatctggaa ggcaaggaat    9540
```

```
gcgaaaatct tcaggaacca aactcaaacg gtacatcatg tgctccagga atgcatctcc    9600
gcttccattc tgtggaggca cagatttcca atgaagaaaa gaatcgtctc cgaccagtgg    9660
tgctccattc tacaaatggc cagagcaggg attagctaat tccggggctt ctacaaaaga    9720
aaggagaggg ctaccgctca tcttctgttt tctgttttcc tcctacttgt ttcttctgcc    9780
tcttcactag ctctagctag ctttactcaa gcaacaaaac gttgctctgc atctgtaaca    9840
acacaatcgt gcgagccgtt tctgggctaa ataattttta aacaggtggg gaacgtctcc    9900
cccccgttga ccgtcaaaaa aaaaaaaact acgagtacca tataaggtac aatctactcc    9960
tatgtcctct aggatatggc tgacatcagc ccactacatt tacaattttg actagatggc   10020
ttactgccat tttgctacag tactagtaca cccttgtact agatgccaca agtacaatct   10080
tgtactagat ggcctattgc caccagcaaa cggacagcag ggctgaccag ctgctaatcc   10140
taatctgcag caagcaaaca aaagggagca gcaaattatc ttacagagga ctctctcact   10200
tcatatcctt ttttcttttc aaatattgac acgttgaatt ctcctgtgga tcttgttctg   10260
tctgtttagt gtctccttt tctttaatat tttatgcat atgaacttg gatggagcac   10320 tttcctatgc ctttataact gactgttagt aaaagagatt gcttcatttg tattccccaa   10380
tttcctgagc tgtgtataaa actgtaactt caggaagagc tggaaaaact aagaagacaa   10440
ctgttgctgt tgcacctaca tttgtctgtg ctaattgtgc taagaagaga ggagaggtac   10500
acatgtaatt ttgtggtgca atatcatgat tgctatttgc tatttggctt taaagagtca   10560
gttgagtaat caaaacattg ttgcttcttc agttttacac aaaattagaa gaaaagcgca   10620
aggctttgga agaggagaag ctccaagcag aggccagaaa gagggtaagt ctgctatggt   10680
ttattttatg gtattgcctg gataatagtg tctgtttat tttgtggcaa catgaagaac   10740 acccatttt gcaaagttac tattcctaat atactggaaa ctataactgc attcttatat   10800
aagcactgga attagaattt tggagtaact ttgtttaacc tacccttttc ctccacattt   10860
tgtggtataa atattttgaa cttgattgag attttttttt tggcatgagt tgtgttgtgt   10920
gttgtctctg acttactgaa atactatcat ttcgaggttt tggaaacgat cagtacagca   10980
attttattta tttccatctt gcttggttag tgcggtaaaa tgcaagacaa gttcagatat   11040
gcttgaagcc ttgaaatgaa cttttctgaa ggtttgtcca tcttgtccat ttgcaggttg   11100
cttctttgtc caatcgatat agttaaattg tttaagcctt ttcttgtata aacacatgca   11160
ctaaacttta agcttgtgaa actatagttg tttcttgtgt acatgaattg atttgtctct   11220
ataatgaata ttttgtccca caaaatctga tattttatt gggaaaagct ataggcctgg   11280
taactttagg tacttatatt agaattgttg aggatgcttg tatctgaagt ctgcttactc   11340
ttagtatgtt gctactgcac atagacctca cttgattggg ctaactatgc ctctgctgtg   11400
tcattcgtac atgcatattt gatgcctctt gtaaacatca ttgcgctttc atggttttat   11460
caatagacta gcatatgaaa atgctttgtt atctgttcac catttcgacg aaactctgcc   11520
tgctttatga tcttttttt atttaatctt tttagggtta aaactaaaat tgccagtatt   11580
tctctttctt gttcctttt ttaggaagaa gaagaagaag ccctaagaca actgaggaag   11640
aacatggtcg tctgaggaaa acccaagcca agcttctacc aagaggggcc ccagctaatg   11700
tattttgtgt tctctgctat gttatttaa tcaattagct tgttttgcat tgttcaattg   11760
gtatttacat tctgaaggaa atctctaggt cttcaattag tttcataagt tattctgctg   11820
catcagttac ttagattttt tttcataatt tcatattcat tgctctggtg ctgcatcaat   11880
tcatctttat agcttcagtt ttgtgttttt actttgtata tgttgctttt ttttgggtgc   11940
```

```
caagacacta acgtcaaggt tagggghttg ttcctttgtg ttcctgattc tttatatacc    12000
tcacattaac atatagtatc ttgatatttt gtgtaaggaa aatatgcttg aaacaacatg    12060
tttcctaggt ttccacatgc atatgacatt attgtccttt ttgctagagt aaataggaat    12120
agtaccatat tgtgtaccac ataaggtgtt agtcgtatgt accctatata atcagtccat    12180
gagacccaat gcaatatatc aaatattcca ccaattatat tctccttcat ggtatcattc    12240
gcctaggttt agatcctaac cctacccgcc gtcgcttccg cactgccccc ccccccccc     12300
gggagaggtc gatctccgcc gggggcaggg cctctgttta agcgctccaa cctattgaac    12360
ccggtgccat cgtcgtcctc ccacaacaaa acgggatctc ccctacctca tccccagggt    12420
accgtcatcg cctcgtccta gggctcgccg tcgactgtcg ccatcaacac ttgatcttca    12480
tcgcatggag gcaaatggat ctcgccctgt cccgtgccgc cgtggtggca gccagggcca    12540
tccacacacc tcgaccctgc gctgtcatgg atgcagccag atctggcgtg tcgctgttga    12600
caggggatc tgcccatctc cacctcgtcg atccgcgttg gcaccttcga ccccgtgtgt    12660
tcgtgacctg ccgtgcgcct tgcgccgccc aatcgggacg caccgccgct gtcatgtcat    12720
cttgctgggt acacccgatc tcctgctgtt gtatctttt ggtttgcccg atcactgatc    12780
gggattgagt cacctaccac ccgtcgacct cgtgcgttct actccgacat cggtatcaac    12840
ttcatcgaca ccgtctctga gtactacgcg catcttctcc gagcaacagg gctgctacta    12900
tgtcgcctca tcaggccaca acaccgtcgt ccgtgtccgc ttcgccgttg catctacatc    12960
gccgtcacct gtgcattgac gactgtgctg cgccatccat ctgcacaaca ctactcgcgt    13020
acctgctcgc cgacgcgtct tcttccgcat tgcttcttct tcgtccaaca caaccacacg    13080
gttgggggcc cctcccttgt acgctcggta ttggcaacac cgacacgtgc tttcgtcccc    13140
gacgcgttgc tggatttggc aaatccaact gcgcctcggc actcaggcga cttgactgca    13200
tcgacttcgg cattgaccct ctcgttccca ccctgtctgc cctcgattgc gtcgttgcct    13260
ttcttctacg tctacgacgg ccctgactgc attgacttcg gcatcgcccc ctcccacgac    13320
gactgcctcg acgcgtctcc gtcattacca tggcgcccct tttgcgcctg cagctccatc    13380
gacacgcaac ccaaccacaa ctacgtcgac ctcggccatc tttagcatgg cttcttcgac    13440
cacggctact gcgcccttac gctcggctac ctcgacatcg gcacaaaggg ctaccgcctt    13500
gcatgaggac tcataagctt tttctccggc cacagcatac ggcgcatcga ctgttatgac    13560
tacgggggga tgttacttat catcttcttc tccagtctta ccgtctgtag cgctctcgct    13620
gtgactgcga agggatgtta gagtaaatag gaataatacc atatagtgtg tacccacata    13680
aggtgttagt cctatgtaca ctatataatc agcccatgag gcccaatgca atatatcaaa    13740
tattctacca attatattct ccttcacttt tgtctggcca gaattgaaat ttcaattttt    13800
ttggacacat aattgcctct ttgcatttga ttctcgtgaa acaaattatt gccattttca    13860
tcatcgactt ggtcagaaga aatgtaaatt tttctcact gaacaaactt gtattgttcc     13920
tactccaatc ctgatataaa tcacccaaag gagcataagt tgtatgttca atcagtttaa    13980
aaatatgtct tcttcacatta atttatactt gtaacctgtt ggtaaattaa tggaaagctg    14040
tataaacttt cctgctttta gcatgtacca gtgcagcct tcatttttt gccttttctt     14100
ttgcaggtgc ctccaactcg tgccaagtca ccaaaattaa cacagacaaa gagctgtgca    14160
gtgacacccc tcagcaaagg gaggaaatgg cagtgcagta tgctgccagt tgcattatca    14220
caacattggg aactccaaag atgttagcag caaggcacaa tgttctccaa agagggcttc    14280
```

```
aaagactgga tcagctacta atccaggga agacctgaag gtttccatga agaaagtggg    14340
acagccaagc gccgcaaact tcgctgtaca aacctaactc atgaggcatt cactcccatg    14400
ccatttttca ttttaatttg tacctcacat cacgaaaaag atggcctcat gccccgacac    14460
cagtgtgttt gttgctggat tatttttgca ttctccttgt aagaacctgg ctaccaatgt    14520
gctgttcggt cctgtaaatt tgttgaaggt tttgtaaggg gtaaccgagt cagtcctgtg    14580
agaaccaagc gggcagccga tgagctgttg gagtgacata ttgtcgttgt gtggcggcat    14640
tggcaggtcc tatgtattgt atctgatctg ttacttattg tgggcattgg caaagcgatt    14700
ctgattgttg ttgcaaaatt tggtcaggtc ttgtttcaag gtatgcttat gaattggaaa    14760
ctgggctgtg attttttccc ccttcttctg tccgaaactt gagacggtaa catgataaag    14820
gatcagtact tgctgtgact atgaaaagta cacaggtgct tcaccagttc tgtaaagatg    14880
actaatcgat acttatactg gttaatccat cagaaacaca ccaccatgat tgatatctgc    14940
aggtgttgaa ggcagctgca gttctcttga accagtgtaa gctgtagaac aacactgaac    15000
atggaaacac aagtttttcaa cgtgagaaaa taagacgtga tttgcgcact tgatgtaatg    15060
tagtgacaac caagtttgca cgatttggtc ggcaagatct gactttgtgc aaatttgact    15120
ctgtaagctg acacattttt ctcccatctt tctactgatg tgaactattc gaggaagcca    15180
tgtgaatggc ttaccatgca tgcacgctac cgacgacatg agcacccatc gcatgtgtgc    15240
tcactttgga gttgggacta ttgatagttg atactagtgt tatatgccag aaagcacggg    15300
gcgatgcgtc tgaaaatgct ccatgtagag tgcgctatgg aggaaaatcc acaccaaaaa    15360
aaagagcaga acagctatct tgagtggtcg agcgagaact ctgaaagagt ggactgcatt    15420
gctaga                                                                15426

<210> SEQ ID NO 9
<211> LENGTH: 2880
<212> TYPE: DNA
<213> ORGANISM: Sorghum bicolor

<400> SEQUENCE: 9
atggacgagc cccgcccccc gcggcccgcg ctcaactccg ccgcggcgac gtcatggccg     60
gagctgctgg cgccgttcga cctgtcccgc ctgcgcgcca cgctgtcctc ccacccgctc    120
accccgcggc gcctggcgcg cctcctcgcg ctcccgctct cccagccac atccctgctc    180 ctcctcgact ggtacgcctc ctcccacccg gcgctctcgc tctcctcgct cccgctccgc    240
cccatcctcg cttctgtcgg ggccgccggg gacccggacc gcgcgctcgc gctcctcgac    300
tccctcccgc gctcctcccg cctgccgccg ctccgcgagt cgctcctgct gccgctgctc    360
cgctccctgc ccccggggccg cgcgctccac ctgctcgacc agatgccccg ccgcttcgcc    420
gtgaccccgt cctccgctc ttacaacgcc gtgctctcca cgctggccag ggccgactgc    480
cacgccgacg cgctgctcct gtaccgccgg atgctccggg accgcgtgcc gcccaccacc    540
ttcaccttcg gcgtcgccgc gcgcgcgctc tgccgactcg gccgcgcgcg cgacgcgctc    600
gcgctgctcc gcgggatggc gcgccacggg tgcgtgcccg acgccgtgct ctaccagacc    660
gtcatccacg ccctggtcgc acagggcggg gtcgccgagg ctgccacgct cctcgacgag    720
atgctgctca gggctgtgc ggcggatgtg aacaccttca cgacgttgt gctcgggctg    780 tgcgggctcg gccatgtgcg ggaggcggcc aggctcgtgg acaggatgat gatgcatgga    840
tgcacgccga gtgtggtgac atatgggttc tcctgcgggg gctgtgccg aacaaggcag    900 gcggacgagg catacgcgat gctggggagg gtgccggagg tgaacgtggt gatgcttaac    960
```

```
acagtgatcc gtggatgtct ggcggagggg aagctggcca gggcgacaga gttgtatgag    1020
atgatgggtt caaaaggatg cccaccggat gtgcacacgt acaatatatt gatgcatggc    1080
ctttgcaagc ttgggaggtg tggttcagca gtccggatgc ttgatgagat ggaggagaag    1140
ggctgtgcac caaacatcgt gacctactct accttgctgc attcgttttg caggaatggc    1200
atgtgggatg acgcaagagc aatgctggat cagatgtcag ccaagggctt tagtatgaac    1260
tcccagggat acaatggtat catatatgcc ttaggcaagg atggcaagct tgatgaagca    1320
atgaggcttg tccaagagat gaagagtcag ggatgcaagc ctgatatttg cacatacaac    1380
acaataattt atcatttgtg caacaatgac cagatggatg aggcagaaca tattttcgga    1440
aacttacttg aagagggtgt tgtcgccaat ggaataacct ataacactct cattcatgca    1500
cttctgcaca gcggaaggtg gcaggaaggc ctaagacttg caaatgaaat ggtacttcat    1560
ggttgcccgc tagatgttgt tagctacaat ggcctgatta agccctctg caaagagggg     1620 aatgttgatc ggagtatgat gttgcttgag gaaatgatga caaagggaat taagccaaat    1680
aatttctcgt ataacatgct gatcaatgaa ctctgcaagg caggaaaggt gcgtgatgca    1740
ttggagctct caaaggagat gctgaatcaa ggactgacac cagacattgt gacttacaat    1800
actctcataa atgggttatg caaagtggga tggacacatg ctgctttaaa tctcctagag    1860
aagctgccca acgaaaatgt gcaccctgac attgtcacat acaacattct cattagttgg    1920
cactgcaaag tcagattgct tgatgatgcg tctatgcttc tagacaaagc agtaagtggg    1980
ggaatagttc ctaatgagcg aacatgggga atgatggtgc aaaattttgt cagacagcca    2040
gtcaatcccg acgctcgatg tgcttttaca tcaatatggg tgcatttaac ttccagcata    2100
gtgactgtcg cgcatgttga tctggttagc aatatcagaa gagattgtga aattgctgtt    2160
gagattgtga tgggatcctt catgcagttt gatctactgt accgtttcct acagagatgc    2220
gatttgtttc atttggtgac tgaaagcatg gcaagtcctc tcaggttgga gtactacata    2280
cagtactatc ttgtaagatt gtgtggctat ttccagtctg ttgaagtacg tttccatgta    2340
gcacttgcca cttgccaggc ccaaggcaag gcaagcgacc cagcagcgtc gtgtgtctcc    2400
ggcgcactcc ccaccgcctc caacctgcag ccccagcgac cagcgtgcgc agcggctcgg    2460
ccgcagatgc acgacgtcgt ggtcgtggtc gtcgcttccg aggctttccc caaagcacga    2520
tgcgtccatg gccatggcca aggcggccga ccatatgaag gcctcagtga cgaggtttct    2580
ttcgctgcac acacgccgag gccgggggct tcctttcgct gcaccaccac ctggccggca    2640
tggccgtcga gtactacga gagcacgacc agcgcagcgt gggctgccc acacggtcaa     2700 tggcgctggc cccacacggc tgacggcacg taaccctat cccttgttgt tctctcggtc     2760
aaaatggatg taccaccacc actcgtgcgc agcgcactgc taggagctca ggcgagtacc    2820
tgctctgtcc tcccgatgct tctccagtgc tcgcttggac gcttaccggg tggaaattag    2880
```

<210> SEQ ID NO 10
<211> LENGTH: 6291
<212> TYPE: DNA
<213> ORGANISM: Sorghum bicolor

<400> SEQUENCE: 10

```
gtttataaag gagctgcggt gttgccccag ccgttggatt ttcacgagga cgatgtgacg      60
atgagggttt gcttattccg cttaatgggc cccaaattca aggagaagga gtttcggccc     120
atgatttgtc aaaaaaaaac attgagggca tgacggccca cataccaaaa gaccagccca     180
```

```
agccgttagc ctggacgggt ggtgggcatc cactagcctg aactgaacgc ggctgctgct    240
cctcccccga cggtgctccc gagctcggca aatgttgtct ccggggcggc ggcggcctga    300
cgaagcgcga cggctaggac aaccgcggcg acctttagtg ccgtcggtgg cggcgtcggg    360
aaactcactc cacgccacgc gctgacatgg acgagccccc gccccgcgg cccgcgctca     420 actccgccgc ggcgacgtca tggccggagc tgctggcgcc gttcgacctg tcccgcctgc    480
gcgccacgct gtcctcccac ccgctcaccc cgcggcgcct ggcgcgcctc ctcgcgctcc    540
cgctctcccc agccacatcc ctgctcctcc tcgactggta cgcctcctcc cacccggcgc    600
tctcgctctc ctcgctcccg ctccgcccca tcctcgcttc tgtcggggcc gccggggacc    660
cggaccgcgc gctcgcgctc ctcgactccc tcccgcgctc ctcccgcctg ccgccgctcc    720
gcgagtcgct cctgctgccg ctgctccgct ccctgccccc gggccgcgcg ctccacctgc    780
tcgaccagat gccccgccgc ttcgccgtga ccccgtcctt ccgctcttac aacgccgtgc    840
tctccacgct ggccagggcc gactgccacg ccgacgcgct gctcctgtac cgccggatgc    900
tccgggaccg cgtgccgccc accaccttca ccttcggcgt cgccgcgcgc gcgctctgcc    960
gactcggccg cgcgcgcgac gcgctcgcgc tgctccgcgg gatggcgcgc cacgggtgcg   1020
tgcccgacgc cgtgctctac cagaccgtca tccacgccct ggtcgacag ggcggggtcg    1080 ccgaggctgc cacgctcctc gacgagatgc tgctcatggg ctgtgcggcg gatgtgaaca   1140
ccttcaacga cgttgtgctc gggctgtgcg ggctcggcca tgtgcgggag gcggccaggc   1200
tcgtggacag gatgatgatg catggatgca cgccgagtgt ggtgacatat gggttcctcc   1260
tgcgggggct gtgccgaaca aggcaggcgg acgaggcata cgcgatgctg gggagggtgc   1320
cggaggtgaa cgtggtgatg cttaacacag tgatccgtgg atgtctggcg gaggggaagc   1380
tggccagggc gacagagttg tatgagatga tgggttcaaa aggatgccca ccggatgtgc   1440
acacgtacaa tatattgatg catggccttt gcaagcttgg gaggtgtggt tcagcagtcc   1500
ggatgcttga tgagatggag gagaagggct gtgcaccaaa catcgtgacc tactctacct   1560
tgctgcattc gttttgcagg aatggcatgt gggatgacgc aagagcaatg ctggatcaga   1620
tgtcagccaa gggctttagt atgaactccc agggatacaa tggtatcata tatgccttag   1680
gcaaggatgg caagcttgat gaagcaatga ggcttgtcca agagatgaag agtcagggat   1740
gcaagcctga tatttgcaca tacaacacaa taatttatca tttgtgcaac aatgaccaga   1800
tggatgaggc agaacatatt ttcggaaact tacttgaaga gggtgttgtc gccaatggaa   1860
taacctataa cactctcatt catgcacttc tgcacagcgg aaggtggcag gaaggcctaa   1920
gacttgcaaa tgaaatggta cttcatggtt gcccgctaga tgttgttagc tacaatggcc   1980
tgattaaagc cctctgcaaa gagggaatgt tgatcggag tatgatgttg cttgaggaaa   2040
tgatgacaaa gggaattaag ccaaataatt tctcgtataa catgctgatc aatgaactct   2100
gcaaggcagg aaaggtgcgt gatgcattgg agctctcaaa ggagatgctg aatcaaggac   2160
tgacaccaga cattgtgact tacaatactc tcataaatgg ttatgcaaa gtgggatgga    2220 cacatgctgc tttaaatctc ctagagaagc tgcccaacga aaatgtgcac cctgacattg   2280
tcacatacaa cattctcatt agttggcact gcaaagtcag attgcttgat gatgcgtcta   2340
tgcttctaga caaagcagta agtgggggaa tagttcctaa tgagcgaaca tggggaatga   2400
tggtgcaaaa ttttgtcaga cagccagtca atcccgacgg ttactagaag gatttattgt   2460
atatgttgta tgtcataatg gttttgggac tctgcagctc gatgtgcttt tacatcaata   2520
tgggtgcatt taacttccag catagtgact gtcgcgcatg ttgatctggt aaatatttct   2580
```

```
tctctgttac aacttgtgca gagtaataat ggatataata gtactaaatt ttgagttgta   2640
ctcacaagta catgtaaatt taaaaagcta acaacttctt atgaaatgtg cttgttgcaa   2700
ttgctgatgt ttgtagcata taagcatatt ttctttatgt agtagaattt tttattcttt   2760
tgaaaatctt gacccaacca tgttctgtga actatagaat ttagagaacc tattataggc   2820
attcacaaac tgtatgtgca tacctgtttg gttgtcatta tggcaaacaa gggcaactac   2880
ccaactgaaa caatggaatt cttcatttta gcactgatgt aatatgattg gtaaatcagt   2940
tgattgcatg aagtgtagct tgatgacata taatgctgag ctttgcagga ctattggagc   3000
cctttttctc ttagattact gattaagcac caaagcaaat ggccattgac agaattcaac   3060
cagagtcttg gctgaaaatg cttgaacggg aagggaagat ccctggtagc atggtggtca   3120
tctcatataa tggacctttc tactattcca gctgcacatc ctacctgcag tattgaactg   3180
ccctaaggta cagaaatcct aggaggcaag aaaaatctgt taactggaca tacagcactt   3240
gcttacataa tcttttttca atttggaaaa gcagcatata gtatgaccca gctggacaca   3300
actgcacccc aaatactatt tcattgtttg ttttcttaaa gtatgaccca acttgcttat   3360
agtcatacag tgttcttcag aatatgacaa cttcaattga ggtgccaaag ggtagttcca   3420
gtgtctactt taaaagaaaa aggggtagct tgagggaaca taatagtttg atggttctgg   3480
agtagctaat gaacttgagg tttaatctga atttttggc acaaccagtc cattattgtg    3540
cgctcttatt ggaatctcta ggttagcaat atcagaagag attgtgaaat tgctgttgag   3600
attgtgatgg gatcctgtaa gttactggaa atagaattgg taaatatcat aaactagaga   3660 tagattttc tcttgatttt cgaaagacag agctgtattg gtagactcca ttatcagcac    3720
tatgataact gtgtgggttt cctaattaca ggaatccctt tggtacagga tcgagacctt   3780
gatacttcat atagatgaaa atttcgtgtt atgttacttc tttatctgtg ggatctgtat   3840
tctgtaaaac tgatgggttt tttcatatag atgaagtttt tgtgttatgt tacttcttta   3900
tctgtgggat ctgtattctg taaaactgat agttttattt gtgtgtgtgg tgtctgtttg   3960
tgaagtaaag tagtagtacc agcattgaga agggacaata tatagatgaa tgccaatgct   4020
gattttaaac atgaaatact acggtttaac gaaaacttaa ttattaaact taagcttatt   4080
gtattgcatt ggtattggct aactaatgta atgtatagtg tattagtgtg gccttcatga   4140
ggctctgccc ctgtgggtgg ctgcattatt ctagcactac tgatctggat cttggatgga   4200
ttcacgattt ttcgtggaaa caggcatgtt tattaagctt ttcactcatt catttatctg   4260
gatattacca taaaacttga agtcatgcag tttgatctac tgtaccgttt cctacagaga   4320
tgcgatttgt ttcatttggt gactgtaagc taacttttaa tacttccccc ttttgtcctg   4380
gcttgtgcag tggcagtgtt gaatacctat gaagcctgaa ccatgggatg gttggcactg   4440
gtcgtgaact tgtgatgctg tctgtggtca gcaattccac ggcagttaag gtcaacattt   4500
ggtctctcct gagagattct gacatgtgct cttttcaaga acactcccat catggtgaac   4560
ccaagcgctt cgatttgatg aagagctgat aaatcatgct tgtggcacag gaaagcatgg   4620
caagtcctct caggttggag tactacatac agtactatct tgtaagattg tgtggctatt   4680
tccagtctgt tgaagtacgg tattattcta acaagcatt tcctaatgca gtgcagcaca    4740
caatatattg ggtggcatcc tgacccagga gcttttcctc tgctcccagc atcgcagagg   4800
cgttcaccga ctgaataacc ttttagtct ttgtggtccg gtcgatattt gttgccggac    4860
tgctggcatc ctgcagtttc catgtagcac ttgccacttg ccaggcccaa ggcaaggcaa   4920
```

```
gcgacccagc agcgtcgtgt gtctccggcg cactccccac cgcctccaac ctgcagcccc    4980
agcgaccagc gtgcgcagcg gctcggccgc agatgcacga cgtcgtggtc gtggtcgtcg    5040
cttccgaggc tttccccaaa gcacgatgcg tccatggcca tggccaaggc ggccgaccat    5100
atgtgtgtgc gtgcgtggga gcaagagcaa actggatggg tcatgggagt tgttaccgtt    5160
cgtcgcgtgt tactaggaaa ttttattcac ccttggattc tgcggctgtc tgctcgaaga    5220
tgctgtagat ggctttggcc tgctccgagt acgacgggcg agagatcaga gatccctgag    5280
cggcagggaa gccgaagctg gtactacgtg tctgcggtcc agtccagccg gccaaggcgt    5340
tcggttggct ggttaagatt ttctgttggg cgatcgatga atgctgctgc ctgctgtgtg    5400
actgctgagg agcagtagtg ccgtggtgtg ccaaaggcgg tgagccgtga ctcgtgaggg    5460
gagagggggc tgcgacgtta ggggtttttt tttggagcac gaccacgcg tgcgtgcgtg     5520 tatggccgta agcatttgcg cgccgcgtgg ccgcgacgca cgcgccgcag ccgtcgagac    5580
accaggggcg tagcgcagac ctgcacgcac gcacacgctc gctcaggcct tgtttacttt    5640 caaaatttt tgcaaaatat gaatagtgac actttcgttt gtatttaaca aatattgtcc     5700
aatcatggac taactagggt caaaagattc atcttgtcaa tttcgaccaa actgtgcaat    5760 tagttttat ttttgtctat atttaatact ctatgcatgc gtttaaagat tcgatgtgac     5820
gaggaatctg aaaaaatttg caaaattttt ttaggaaggc ctcagtgacg aggtttcttt    5880
cgctgcacac acgccgaggc cggggcttc ctttcgctgc accaccacct ggccggcatg     5940
gccgtcgcag tactacgaga gcacgaccag cgcagcgttg gctgcccac acggtcaatg     6000 gcgctggccc cacacggctg acggcacggt aaccctatcc cttgttgttc tctcggtcaa    6060
aatggatgta ccaccaccac tcgtgcgcag cgcactgcta ggagctcagg cgagtacctg    6120
ctctgtcctc ccgatgcttc tccagtgctc gcttggacgc ttaccgggtg gaaattaggc    6180
cttgtttaga tatgcctaaa atccaaaaaa aaaaatcaag attctttatc acatcaaata    6240
ttgcagcaca agtacagtac attaaatata ataatatttt attaaatgaa a             6291

<210> SEQ ID NO 11
<211> LENGTH: 2091
<212> TYPE: DNA
<213> ORGANISM: Sorghum bicolor

<400> SEQUENCE: 11
atgtcgagcc ggacgtgcct gaagaagctg aagcggatca ttggacggcg catccgctcg      60
ggaagcctca gcgctgaggc cgcgcgccaa ctctggaacg aggtgctccc atcgatccaa     120
tatcgttccc caccaccggc cgcttcagca gccgcgcgcc ggtggagagc cgaccgccgc     180
cgttcctggg agctggagca gttcatcgga gagtgttacc gctcgggga cctcggcccc      240 gaggacgcac tcgatctgtt cgacgaattg cttcagcgag cgaggcccgg ctccatttac     300
gccctcaacc agctgctcac cacggtcgct cgcgcccccg tctcctcctc tgtgcgcgat     360
ggccctgcgc tcgccgtgtc catgttcaac cgtatgcccc gagcgggcgc caagaaggtg     420
gctccagaca tagctaccct tcggcatcct catcagctgc tgttgcgacg gggctgtttg     480
aacctcggct tcgctgcatt gggcaaaatc attaagacgg gactgaggc acaggccgtc      540 accttcacgc ccctgctcag gaccctctgc gccgagaaga ggacgagtga cgcaatgaat     600
attgtgctca gcggatgcc tgagctcggc tgcacccccg atgtcttctc ctacaccaca      660
cttctcaaag ggctttgtgc tgagaagaaa tgtgaagagg ctgccgagct gatccacatg     720
atggctgaag atggagacaa ctgcccacct aatgtggtgt cttataccac tgtaatccat     780
```

```
ggattctttta aagagggaga tgtagggaaa gcttacaccc tgttttgcaa aatgcttgat      840
catgggatcc cgccaaatgt tgtgacctgc aattcagtca ttgatggcct atgcaaggtt      900
caagcaatgg acaaggccga ggcagtcctt cagcagatga ttgacgagca tattatgcct      960
aattgtacta catataacag tctgatccat ggatacctct cttcaggaca gtggacggag     1020
gcagtcagaa ttctcaaaga aatgtctaga gatgggcaac ggccaaatgt tgttacttac     1080
agtatgctca tagactgtct ttgtaaatct ggattgcacg cagaagctag agagatcttt     1140
aattctatga ttcagagcgg tcaaaaaccc aatgcctcca cttatggcag tctgcttcat     1200
gggtatgcta ccgaaggcaa tcttgttgat atgaacaatg tcaaagatct aatggtacaa     1260
aatggaatgc gacctggccg tcatgtcttc aacatagaaa tctatgcata ctgtaaatgt     1320
ggaaggctag atgaggcaag ccttactttt aacaaaatgc agcagcaagg attcatgcca     1380
gacatagtcg cctacaccac agttatagat gggctttgca agataggccg gctggacgat     1440
gcaatgtccc gattctgtca gatgattgat gatggattgt ctcccgatat cataacattc     1500
aatactctaa ttcatggttt tgctttgcat ggcaaatggg agaaggccga ggaattattt     1560
tatgagatga tggatagagg cattcctcct aatgtcaata cgttcaattc aatgatagac     1620
aagctattca agaaggaaa ggttacagag gcccgaaaac tctttgattt gatgccacgt      1680
gcaggagcta aacctaatgt tgttctttat aatacaatga ttcatgggta tttcatagct     1740
ggtgaagtgg gcgaagtgat gaagctcctt gatgatatgc tcttgattgg cttgaaaccc     1800
actgctgtta cctttaatac tttacttgat ggcatggtct ctatgggatt gaaacctgat     1860
gttgttacct gtaagacttt gattgatagc tgctgtgaag atggcaggat agaggatata     1920
ttaactctgt tccgagaaat gttgggcaag gctgataaga ctgacactat cacggaaaat     1980
ataaaactac gaggtgtaac cgtgaaagct tcttatcact gttccagtgt ggtaatttcg     2040
ctcaaagctt tagaagttgt tacacaagca ggagctattt catgcatttg a              2091

<210> SEQ ID NO 12
<211> LENGTH: 2997
<212> TYPE: DNA
<213> ORGANISM: Sorghum bicolor

<400> SEQUENCE: 12
tgtattaata taacttgtgc tgtaagcatc cttgcagact tgctctctca aatgcatgaa       60
atagctcctg cttgtgtaac aacttctaaa gctttgagcg aaattaccac actggaacag      120
tgataagaag ctttcacggt tacacctcgt ctacacatgt tttaaaatca gatgacttca      180
tatcagacta aggaccaggt cttgttgaac tcgtcaagtg tagaaaaacg aaaatacagt      240
ttcttcagca aacaaaaata cttgtgctct aaaaaaataa tgcccaagca tgcaggcaga      300
tataaagatg gcccttatat tgaaaggagt gccctcacaa atatccttca gaaaatatca      360
aactcacaaa attcgcaaca ctaaaatttt caaagacaag aagatctacc atatacatac      420
tccagggtag atgagaaatt gtaccttaac ttctccagat tgatgacact tccaaatcat      480
cttcaagtac aattaaggac aacataagac atcatagtta aggttaacac tccattctct      540 atttaccccct tttggtcatc tgcagcttga gttccgtgcc aatggaagtc catcaattct      600
gaaatgacac tcacagtttt atattttccg tgatagtgtc agtcttatca gccttgccca      660
acatttctcg gaacagagtt aatatatcct ctatcctgcc atcttcacag cagctatcaa      720
tcaaagtctt acaggtaaca acatcaggtt tcaatcccat agagaccatg ccatcaagta      780
```

```
aagtattaaa ggtaacagca gtgggtttca agccaatcaa gagcatatca tcaaggagct    840
tcatcacttc gcccacttca ccagctatga aatacccatg aatcattgta ttataagaaa    900
caacattagg tttagctcct gcacgtggca tcaaatcaaa gagttttcgg gcctctgtaa    960
cctttccttc tttgaatagc ttgtctatca ttgaattgaa cgtattgaca ttaggaggaa   1020
tgcctctatc catcatctca taaataatt cctcggcctt ctcccatttg ccatgcaaag    1080
caaaaccatg aattagagta ttgaatgtta tgatatcggg agacaatcca tcatcaatca   1140
tctgacagaa tcgggacatt gcatcgtcca gccggcctat cttgcaaagc ccatctataa   1200
ctgtggtgta ggcgactatg tctggcatga atccttgctg ctgcattttg ttaaaagtaa   1260
ggcttgcctc atctagcctt ccacatttac agtatgcata gatttctatg ttgaagacat   1320
gacggccagg tcgcattcca ttttgtacca ttagatcttt gacattgttc atatcaacaa   1380
gattgccttc ggtagcatac ccatgaagca gactgccata agtggaggca ttgggttttt   1440
gaccgctctg aatcatagaa ttaaagatct ctctagcttc tgcgtgcaat ccagatttac   1500
aaagacagtc tatgagcata ctgtaagtaa caacatttgg ccgttgccca tctctagaca   1560
tttctttgag aattctgact gcctccgtcc actgtcctga agagaggtat ccatggatca   1620
gactgttata tgtagtacaa ttaggcataa tatgctcgtc aatcatctgc tgaaggactg   1680
cctcggcctt gtccattgct tgaaccttgc ataggccatc aatgactgaa ttgcaggtca   1740
caacatttgg cgggatccca tgatcaagca ttttgcaaaa caggggtgtaa gctttcccta   1800 catctccctc tttaaagaat ccatggatta cagtggtata agacaccaca ttaggtgggc   1860
agttgtctcc atcttcagcc atcatgtgga tcagctcggc agcctcttca catttcttct   1920
cagcacaaag ccctttgaga agtgtggtgt aggagaagac atcggggtg cagccgagct    1980 caggcatccg cctgagcaca atattcattg cgtcactcgt cctcttctcg gcgcagaggg   2040
tcctgagcag gggcgtgaag gtgacggcct gtgccctcag tcccgtctta atgatttgcc   2100
ccaatgcagc gaagccgagg ttcaaacagc ccgcgtcgca acagcagctg atgaggatgc   2160
cgaaggtagc tatgtctgga gccaccttct tggcgcccgc tcgggccata cggttgaaca   2220
tggacacggc gagcgcaggg ccatcgcgca cagaggagga gacggggggcg cgagcgaccg   2280 tggtgagcag ctggttgagg gcgtaaatgg agccgggcct cgctcgctga agcaattcgt   2340
cgaacagatc gagtgcgtcc tcggggccga ggtcccccga gcggtaacac tctccgatga   2400
actgctccag ctcccaggaa cggcggcggt cggctctcca ccggcgcgcg gctgctgaag   2460
cggccggtgg tggggaacga tattggatcg atgggagcac ctcgttccag agttggcgcg   2520
cggcctcagc gctgaggctt cccgagcgga tgcgccgtcc aatgatccgc ttcagcttct   2580
tcaggcacgt ccggctcgac atggtcggcg ccgtcgctcc gattcggtgg caaatgctgc   2640
tcggcgctgg gatggagcca actgaggcag gagattggag atggtagtgg tggcggagct   2700
ggagttggga acgaatggag gtgcccttc gcgtgagcca gcagaggact gatcacgtgc    2760
ttggcatgtc gtcttcttcg ggctttgacc gagtataaat ctaatctgga gattttttt    2820 tttcttcaca aaataaaatt agttcgactg ccaaacaagt taccctacaa agaaaaatgt   2880
aacttgggtg cattctcggt aaaaaaaatg caaagtttaa ccaaataggt agataatatt   2940
attaatgttt ttgacacaat aaatatattt taaaaaatat cttatgaaaa atctaat     2997
```

```
<210> SEQ ID NO 13
<211> LENGTH: 1599
<212> TYPE: DNA
<213> ORGANISM: Sorghum bicolor
```

<400> SEQUENCE: 13

```
atggcccgag cgggcgccaa gaaggtggct ccagacatag ctaccttcgg catcctcatc      60
agctgctgtt gcgacgcggg ctgtttgaac ctcggcttcg ctgcattggg caaataatt     120
aagacgggac tgagggcaga tgccgtcgcc ttcacgcccc tgctcaggac cctctgcgcc    180
aagaaaagga cgagtgacgc aatgaatatt gtgctcaggc ggatgcctga acttggctgc    240
accccgatg tcttctccta cagcacactt ctcaaagggc tttgtgctga agaaaatgt      300
gaagaggctg ccgagctgat ccacatgatg gctgaagatg agacaactg cccacctgat     360
gtggtgtctt atagcactgt aatccatggg ttctttaaag agggagatgt agggaaagct    420
tacaccctgt tttgcaaaat gcttgatcat gggatccctc caaatgttgt gacctgcaat    480
tcagtcattg atggcctatg caaggttcaa gcaatggaca aggccgaggc agtccttcag    540
cagatgattg acgagcatat tatgcctaat tgtactacat ataacagtct gatccatgga    600
tacctctctt caggacagtg gacggaggca gtcagaattc tcaaagaaat gtctagagat    660
gggcaacggc caaatgttgt tacttacaat atgctgatag actgtctttg taaatctgga   720
tttcacgcag aagctagaga gatctttaat tctatgattc agagcggtcc aaagcccgat   780
gccaccactt atggaagtct gcttcatggg tatgctaccg aaggcaatct agttgaaatg   840
aacaatgtca agatttgat ggtacagaat ggaatgcgat ctaatcatca taccttcagc     900
atagagatct atgcatactg taaatgtgga aggttagatg aggccagcct tacttttatc    960
aaaatgcagc agcttggatt catgccagac atagtcacct acaccacagt tatagatggg   1020
ctttgcaaga taggccggct ggacgatgca atgtcccgat tctgtcagat gattgatgat   1080
ggattgtctc ccaatatcat aacatttacg accctaattc atgggttttc tatgtatggc   1140
aaatgggaaa aggctgagga actatttat gagatgatgg atagaggcat tcctcctgat   1200
gtcactatct tcactgcaat gatagatagg ctattcaaag aaggaaaggt tacggaggcc   1260
caaaaactct ttgatttgat gccacgtgca ggagctaaac ctaatgttgt ttcttataat   1320
acaatgattc atgggtattt catagctggt gaagtgggcg aagtgatgaa gctccttgat   1380
gatatgctct tgattggctt gaaacccact gctgttacct ttaatacttt acttgatggc   1440
atggtctcta tgggattgaa acctgatgtt gacacctgta agactttaat tgatagctgc   1500
tgtgaagatg gcaggataga ggatatatta actctgttcc gagaaatgtt gggcaaggct   1560
gataagactg acactatcac ggaaaatata aaactgtga                           1599
```

<210> SEQ ID NO 14
<211> LENGTH: 2866
<212> TYPE: DNA
<213> ORGANISM: Sorghum bicolor

<400> SEQUENCE: 14

```
tttttgcac aaaattaagg accttcccta ttgtatctaa cacaattcag ggatcactgc       60
tagtgccctt ttgctggcca tctccctcaa tacttgttcc tccagttttc ttgattggca    120
tccccttttt ggtgctagat gttgatggca atggcagtcc atcaattctg taaatgacac    180
tcacagtttt atattttccg tgatagtgtc agtcttatca gccttgccca acatttctcg    240
gaacagagtt aatatatcct ctatcctgcc atcttcacag cagctatcaa ttaaagtctt    300
acaggtgtca acatcaggtt tcaatcccat agagaccatg ccatcaagta agtattaaa    360
ggtaacagca gtgggtttca agccaatcaa gagcatatca tcaaggagct tcatcacttc    420
```

```
gcccacttca ccagctatga atacccatg  aatcattgta ttataagaaa caacattagg   480
tttagctcct gcacgtggca tcaaatcaaa gagttttgg  gcctccgtaa cctttccttc   540
tttgaatagc ctatctatca ttgcagtgaa gatagtgaca tcaggaggaa tgcctctatc   600
catcatctca taaaatagtt cctcagcctt ttcccatttg ccatacatag aaaacccatg   660
aattagggtc gtaaatgtta tgatattggg agacaatcca tcatcaatca tctgacagaa   720
tcgggacatt gcatcgtcca gccggcctat cttgcaaagc ccatctataa ctgtggtgta   780
ggtgactatg tctggcatga atccaagctg ctgcattttg ataaaagtaa ggctggcctc   840
atctaacctt ccacatttac agtatgcata gatctctatg ctgaaggtat gatgattaga   900
tcgcattcca ttctgtacca tcaaatcttt gacattgttc atttcaacta gattgccttc   960
ggtagcatac ccatgaagca gacttccata agtggtggca tcgggctttg gaccgctctg  1020
aatcatagaa ttaaagatct ctctagcttc tgcgtgaaat ccagatttac aaagacagtc  1080
tatcagcata ttgtaagtaa caacatttgg ccgttgccca tctctagaca tttctttgag  1140
aattctgact gcctccgtcc actgtcctga agagaggtat ccatggatca gactgttata  1200
tgtagtacaa ttaggcataa tatgctcgtc aatcatctgc tgaaggactg cctcggcctt  1260
gtccattgct tgaaccttgc ataggccatc aatgactgaa ttgcaggtca caacatttgg  1320
agggatccca tgatcaagca ttttgcaaaa cagggtgtaa gctttcccta catctccctc  1380
tttaaagaac ccatggatta cagtgctata agacaccaca tcaggtgggc agttgtctcc  1440
atcttcagcc atcatgtgga tcagctcggc agcctcttca catttcttct cagcacaaag  1500
ccctttgaga agtgtgctgt aggagaagac atcggggtg  cagccaagtt caggcatccg  1560
cctgagcaca atattcattg cgtcactcgt ccttttcttg gcgcagaggg tcctgagcag  1620
gggcgtgaag gcgacggcat ctgccctcag tcccgtctta attatttgcc ccaatgcagc  1680
gaagccgagg ttcaaacagc ccgcgtcgca acagcagctg atgaggatgc cgaaggtagc  1740
tatgtctgga gccaccttct tggcgcccgc tcgggccata ggttgaacat ggacacggcg  1800
agcgcagggc catcgcgcac agaggaggag acgggggcgc gagcgaccgt ggtgagcagc  1860
tggttgaggc gtaaatgga  gccgggcctc gctcggtgaa gcaattcgtc gaacagatcg  1920
agtgcgtcct cggggccgag gtcccccgag cggtaacact ctccgatgaa ctgctccagc  1980
tcccaggaag ggcggcggtc ggctctccac cggcgcgcgg ctgctgaagc ggccggtggt  2040
ggggaacgat attggatcga tgggagcacc tcgttgcaga gttggcgcgc ggcctcagcg  2100
ctgaggcttc ccgagcggat gcgccgtcca atgatccgct tcagcttctt caggcacgtc  2160
cggctcgaca tggtcggcgc cgtcgctccg attcggtggc aaatgctgct cggcgctggg  2220
atggagccaa ctgaggcagg agattggaga tggtagtggt ggcggagctg gagttgggaa  2280
cgaatggagg tgccccttcg cgtgagccag cagaggactg atcacgtgct ggcatgagt   2340 ataaatctaa tctggagatt ttttttttctt cacaaaatca aattagttcg actgccaaac  2400
aagttaccct acaaagaaaa atgtaacttg ggtgcattct cggtaaaaaa atgcaaagtt  2460
taaccaaata ggtagataaa tattattaat gttttgaca  caataaatat attttaaaaa  2520
atatcttatg aaaatctaaa tgatacttat tttatctcaa aactattcat atttttttat  2580
tcttaatata taattatgaa atttcagtc  tcgcaacttt ctgtccgcga tccgaaatca  2640
gctcaacttt ctgtctgcca atctatccat gatccggaat cagcccgtgg cttcaacgcc  2700 ggtgaaaag  aggaaaaata atagaaattt ttctcgggtt ttcaatacaa aatctcctat  2760
atacattaga gcacgttgaa aataataaaa gtacaaaggt aaatataaat agatatgtaa  2820
```

```
cattatgtca tcactttctt tgaccatttg atgtttctcc cacgtt              2866
```

<210> SEQ ID NO 15
<211> LENGTH: 1881
<212> TYPE: DNA
<213> ORGANISM: Sorghum bicolor

<400> SEQUENCE: 15

```
atgttctaca ccagaactct tcaaggcagc cggccggttc ggcagcgggg tcggaggtac    60
gaaaaccgcc cgtcctgcga gctggagcgc ttcatcggag agtgtttccg ctcgggagac   120
cttgaccccg aggacgcact cgatctgttc gacgagctgc ttccccaagc gaggcaaggc   180
tccgtttatg ccctcacccg gctcctcacc actgtcgctc gcgcccagt  ctcctccgcc   240
gtgcccaacg gccctgccct cgccgtgtcc atgttcaacc gcatggcccg agcgggctcc   300
aagaaggttg ctccgaccac agttacctac accatcctca tcagctgctg ctgctatgta   360
ggctgcttga acctcgcctt tgccgcattg ggccaaatca ttaagacggg actgagggca   420
aatgccatca gtttcacgcc tatacttagg accctctgtg ctgagaagag gacgagtgat   480
gcaatgaata ttgtgatcag atggacgcct aagcttggct gcaccccgga tgtcttctcc   540
tacaccgtac ttctcaaagg gctatgtgac gagaagaaat gtgaagaggc tgttgacctg   600
atccacatga tggctgagga tggagatcac tgcccaccta atgtggtgtc ttataccacc   660
gtaatccatg gcttctttaa agaggatgag gtggggaaag cttacaccct gttttgtgaa   720
atgcttgatc gtgggatccc gccggatgtt gtgacttgca actcaatcat tgatggccta   780
tgcaaggttc aagcaatgga caaggctgag gaggtccttc gacagatgtt tgacaaacat   840
attatgcctg actgcactac atataacagt ctggtccatg gatacctctc ttcgggacaa   900
ctgaaagagg cggtcagaat tctcaaacaa atgtcaagac atgggcaacc accaaatggt   960
gttacttaca gcatgctgat agactgtctt tgcaaatttg gagggcacac agaagctaga  1020
gaaattttga attctatgat tcagagccgt ggaaacccca atgttgccac ctacggaggt  1080
ctgcttcatg ggtacgctac caaaggagat cttgttgaaa tgaataatct catagatttg  1140
atggtacaga acggagtgcg acctgatcat catatcttca acatacagat ttatgcatac  1200
gtcaaatgtg gaaggttaga tgaggcaatg cttacttta acaaaatgcg gcagcaagga  1260
ttgatgccag acataatcag ctatgggacg atgatagatg ggctttgcaa gataggccgg  1320
ctggacgctg caatgtccca attctgtcag atgattgatg atggattgtc tccagatatt  1380
gtagtattta ctaatctaat acatggtttt tctatgtacg gcaaatggga gaaggctgag  1440
gaactatttt atgagatgat ggatagaggc attcgtccta ctgtcgttgt cttcactaca  1500
atgatagaca agctattcaa agaaggaaag gttaccgagg ccaaaacact ctttgatttg  1560
atgccaattg ctagtgtaaa acctaatgtg gtttcctaca atgcaatcat tcatggatat  1620
ttcttggctg gtaaactgga tgaagtgctg aagctccttg atgatatgct ctcagttggc  1680
ttgaaacccca atgctgttac tttttaatact ttacttgatg acatgctttc tatgggcttg  1740
aaacccgatg ttgctacctg taacactttg attgatagct gctgtgaaga cggtaggata  1800
gaagatgtat tgactctttt cagagaaatg ttgagcaagg cagctaagac tgacactgtc  1860
acggaaaata taatttcctg a                                             1881
```

<210> SEQ ID NO 16
<211> LENGTH: 2771
<212> TYPE: DNA

<213> ORGANISM: Sorghum bicolor

<400> SEQUENCE: 16

```
tttatccaac aagcgcaaca taacacgtcc tacttaagat taagaacctg tttccctcct      60
ttggtcatct tcaggttgag ttccatctta atgccagtcc ttccaatctg aaataacact     120
caggaaatta tattttccgt gacagtgtca gtcttagctg ccttgctcaa catttctctg     180
aaaagagtca atacatcttc tatcctaccg tcttcacagc agctatcaat caaagtgtta     240
caggtagcaa catcgggttt caagcccata gaaagcatgt catcaagtaa agtattaaaa     300
gtaacagcat tgggtttcaa gccaactgag agcatatcat caaggagctt cagcacttca     360
tccagtttac cagccaagaa atatccatga atgattgcat tgtaggaaac cacattaggt     420
tttacactag caattggcat caaatcaaag agtgttttgg cctcggtaac ctttccttct     480
ttgaatagct tgtctatcat tgtagtgaag acaacgacag taggacgaat gcctctatcc     540
atcatctcat aaaatagttc ctcagccttc tcccatttgc cgtacataga aaaccatgt      600
attagattag taaatactac aatatctgga gacaatccat catcaatcat ctgacagaat     660
tgggacattg cagcgtccag ccggcctatc ttgcaaagcc catctatcat cgtcccatag     720
ctgattatgt ctggcatcaa tccttgctgc cgcattttgt taaagtaag cattgcctca      780
tctaaccttc cacatttgac gtatgcataa atctgtatgt tgaagatatg atgatcaggt     840
cgcactccgt tctgtaccat caaatctatg agattattca tttcaacaag atctcctttg     900
gtagcgtacc catgaagcag acctccgtag gtggcaacat tggggtttcc acggctctga     960
atcatagaat tcaaaatttc tctagcttct gtgtgccctc caaatttgca agacagtct    1020
atcagcatgc tgtaagtaac accatttggt ggttgcccat gtcttgacat ttgtttgaga   1080
attctgaccg cctcttttcag ttgtcccgaa gagaggtatc catggaccag actgttatat   1140
gtagtgcagt caggcataat atgtttgtca acatctgtc gaaggacctc ctcagccttg    1200
tccattgctt gaaccttgca taggccatca atgattgagt tgcaagtcac aacatccggc   1260
gggatcccac gatcaagcat ttcacaaaac agggtgtaag ctttccccac ctcatcctct   1320
ttaaagaagc catggattac ggtggtataa gacaccacat taggtgggca gtgatctcca   1380
tcctcagcca tcatgtggat caggtcaaca gcctcttcac atttcttctc gtcacatagc   1440
cctttgagaa gtacggtgta ggagaagaca tccggggtgc agccaagctt aggcgtccat   1500
ctgatcacaa tattcattgc atcactcgtc ctcttctcag cacagagggt cctaagtata   1560
ggcgtgaaac tgatggcatt tgccctcagt cccgtcttaa tgatttggcc caatgcggca   1620
aaggcgaggt tcaagcagcc tacatagcag cagcagctga tgaggatggt gtaggtaact   1680
gtggtcggag caaccttctt ggagcccgct cgggccatgc ggttgaacat ggacacggcg   1740
agggcagggc cgttgggcac ggcggaggag actggggcgc gagcgacagt ggtgaggagc   1800
cgggtgaggg cataaacgga gccttgcctc gcttggggaa gcagctcgtc gaacagatcg   1860
agtgcgtcct cggggtcaag gtctcccgag cggaaacact ctccgatgaa gcgctccagc   1920
tcgcaggacg ggcggttttc gtacctccga ccccgctgcc gaaccggccg gctgtgggga   1980
acgcatttgg atcgacggga gcaccttgtc gcagagttgg cgcgcggcct aagcgctgag   2040
gcttcccgag cggaggcgcc gcccgatgat ccgcttcaac ttcttcagcc aagacgggcg   2100
cggccggttc gacatggtcg gcgccggcgg tgggatccac acgtctcgcg cctccgattc   2160
ggtggcaaat gcagatcgcg ctgggatggt ccgcactccg cacagcgcgg cggcggcgta   2220
cgctttctgt ggagtggtgg gggggaacga atagaagccg agtgttgggg ggctgaccac   2280
```

-continued

```
gtgcttgagt ggggcctggg aacgaatgga agctgcctac acgtatgcat cgtgtacaat    2340
gacgaatcta gaaaaatatt tagggaaagc ttctgctact taagataact tcagtccctt    2400
cttaaagagc atcaatgata aaaatttgta ggaggggcta aggaggggct acgtgggttc    2460
tacggccgta gggggctgga gccccacca gccccaccgt tggctccgtc gctgatcgtg    2520
tatttgtatt tgtatttgta tacacacacg aggtgatatg cactactaac ctgccttgaa    2580
gagttctggt gtagaacatg ttccgtagag gcttccaagt cgtctaacgc ttataatagt    2640
tttcttggat gcaaggaaaa aaaagaattc aatatcatca acgaaacatc gcattttgat    2700 ttttttttggt ttcaagtgat cgtgagaaga ttctcagtat tatggccttg ttcatttcgc    2760
gaaatttttt t                                                         2771
```

<210> SEQ ID NO 17
<211> LENGTH: 1692
<212> TYPE: PRT
<213> ORGANISM: Sorghum bicolor

<400> SEQUENCE: 17

```
Met Ser Thr Arg Ala Arg Pro Ala Trp Leu Asn Lys Leu Lys Arg Ile
1               5                   10                  15

Ile Gly Arg Arg Ile Arg Ser Gly Ser Leu Ser Ala Glu Ala Ala Arg
                20                  25                  30

Gln Leu Cys Asp Glu Val Leu Pro Ser Ile Gln Ser Arg Ser Pro Pro
            35                  40                  45

Pro Ala Ala Ser Ala Ala Ala Arg Arg Trp Arg Ala Asp Arg Arg Pro
        50                  55                  60

Ser Trp Glu Leu Glu Gln Phe Ile Gly Gln Cys Tyr Arg Ser Gly Asp
65                  70                  75                  80

Leu Ala Pro Glu Asp Ala Val Asp Leu Phe Asp Glu Leu Leu His Gln
                85                  90                  95

Ala Arg Pro Gly Ser Ile Tyr Ala Leu Asn Gln Leu Leu Thr Thr Val
            100                 105                 110

Ala Arg Ala Pro Val Ser Ser Thr Val Arg Asp Gly Pro Ala Arg Ala
        115                 120                 125

Val Ser Met Phe Asn Arg Met Ala Arg Ala Gly Ala Lys Lys Val Ala
    130                 135                 140

Pro Asp Ile Ala Thr Phe Gly Ile Leu Ile Ser Cys Cys Asn Ala
145                 150                 155                 160

Gly Cys Leu Asn Leu Gly Phe Ala Ala Leu Gly Gln Ile Ile Lys Thr
                165                 170                 175

Gly Val Arg Ala His Ala Val Thr Phe Thr Pro Leu Leu Arg Thr Leu
            180                 185                 190

Cys Ala Glu Lys Arg Thr Ser Asp Ala Met Asn Ile Val Leu Arg Arg
        195                 200                 205

Met Pro Glu Leu Gly Cys Thr Pro Asp Val Phe Ser Tyr Thr Thr Leu
    210                 215                 220

Leu Lys Gly Leu Cys Ala Glu Lys Cys Glu Glu Ala Ala Glu Leu
225                 230                 235                 240

Ile His Met Met Ala Glu Asp Gly Asp Asn Cys Pro Pro Asn Val Val
                245                 250                 255

Ser Tyr Ser Thr Val Ile His Gly Phe Phe Lys Glu Gly Glu Val Gly
            260                 265                 270

Lys Ala Tyr Thr Leu Phe Cys Lys Met Leu Asp His Gly Ile Pro Pro
```

```
              275                 280                 285
Asp Val Val Thr Cys Asn Ser Val Ile Asp Gly Leu Cys Lys Ala Gln
290                 295                 300

Ala Met Asp Lys Ala Glu Glu Val Leu Gln Gln Met Ile Asp Glu His
305                 310                 315                 320

Ile Met Pro Asp Cys Thr Thr Tyr Asn Ser Leu Ile His Gly Tyr Leu
                325                 330                 335

Ser Leu Gly Gln Trp Lys Glu Ala Val Gln Ile Leu Lys Glu Met Ser
                340                 345                 350

Arg Asp Gly Gln Gly Pro Asn Val Val Thr Tyr Ser Met Leu Ile Asn
                355                 360                 365

Cys Leu Cys Lys Ser Gly Leu Arg Ala Glu Ala Arg Glu Ile Phe Asn
370                 375                 380

Ser Met Ile Gln Ser Gly Gln Lys Pro Asn Ala Ala Thr Tyr Arg Ser
385                 390                 395                 400

Leu Leu His Gly Tyr Ala Thr Glu Gly Asn Leu Val Asp Met Asn Asn
                405                 410                 415

Val Lys Asp Leu Met Val Gln Asn Gly Met Arg Pro Asp Arg His Val
                420                 425                 430

Phe Asn Ile Glu Ile Tyr Ala Tyr Cys Lys Cys Gly Arg Leu Asp Glu
                435                 440                 445

Ala Ser Leu Thr Phe Asn Lys Met Gln Gln Leu Gly Phe Met Pro Asp
450                 455                 460

Ile Val Thr Tyr Thr Thr Val Ile Asp Gly Leu Cys Lys Ile Gly Arg
465                 470                 475                 480

Leu Asp Asp Ala Met Ser Arg Phe Cys Gln Met Ile Asp Asp Gly Leu
                485                 490                 495

Ser Pro Asn Ile Ile Thr Phe Thr Thr Leu Ile His Gly Phe Ser Met
                500                 505                 510

Tyr Gly Lys Trp Glu Lys Ala Glu Glu Leu Phe Tyr Glu Met Met Asp
                515                 520                 525

Arg Gly Ile Pro Pro Asn Val Asn Thr Phe Asn Ser Met Ile Asp Arg
                530                 535                 540

Leu Phe Lys Glu Gly Lys Val Thr Glu Ala Arg Lys Leu Phe Asp Leu
545                 550                 555                 560

Met Pro Arg Ala Gly Ala Lys Pro Asn Val Val Ser Tyr Asn Thr Met
                565                 570                 575

Ile His Gly Tyr Phe Ile Ala Gly Glu Val Gly Glu Val Met Lys Leu
                580                 585                 590

Leu Asp Asp Met Leu Leu Ile Gly Leu Lys Pro Asn Ala Val Asn Leu
                595                 600                 605

Asn Thr Leu Leu Asp Gly Met Leu Ser Ile Gly Leu Lys Pro Asn Val
                610                 615                 620

Asp Thr Cys Lys Thr Leu Ile Asp Ser Cys Cys Glu Asp Asp Arg Ile
625                 630                 635                 640

Glu Asp Ile Leu Thr Leu Phe Arg Glu Met Leu Ser Lys Ala Asp Lys
                645                 650                 655

Thr Asp Thr Ile Thr Glu Asn Ile Lys Leu Lys Cys Met Lys Lys Lys
                660                 665                 670

Asn Lys Val Trp Leu Asn Lys Leu Lys Arg Ile Ile Gly Arg Arg Ile
                675                 680                 685

Arg Ser Gly Ser Leu Ser Ala Glu Ala Ala Arg Gln Leu Cys Asp Asp
690                 695                 700
```

```
Val Ile Gln Arg Arg Pro Pro Pro Ala Val Ser Ala Ala Arg
705                 710             715                 720

Trp His Trp Asp Asp His Arg Pro Ser Trp Glu Leu Glu Arg Phe Ile
                725             730             735

Gly Val Cys Tyr Arg Ser Gly Asp Leu Gly Pro Glu Asp Ala Leu Gly
            740             745             750

Leu Phe Asp Glu Leu Leu Leu Gln Ala Arg Pro Gly Ser Val Tyr Ala
        755             760             765

Leu Asn Gln Leu Pro Thr Thr Ile Ala His Ala Pro Val Ser Ser Thr
    770             775             780

Val Asp Asp Gly Pro Ala Leu Ala Val Ser Leu Phe Ile Arg Met Ala
785             790             795             800

Arg Ala Gly Ala Lys Lys Val Ala Pro Asn Ile Ala Thr Tyr Asn Ile
                805             810             815

Val Ile Ser Cys Cys Cys His Ala Gly Cys Leu Asn Leu Ser Phe Ala
            820             825             830

Ala Leu Arg Gln Ile Ile Lys Thr Gly Leu Arg Thr Asp Ala Met Ile
        835             840             845

Phe Thr Pro Met Leu Arg Thr Leu Cys Ala Glu Lys Arg Thr Ser Asp
    850             855             860

Ala Met Asp Ile Val Val Arg Arg Met Pro Glu Leu Cys Ser Thr Pro
865             870             875             880

Asn Val Phe Ser Tyr Asn Thr Leu Leu Glu Gly Leu Cys Asp Glu Lys
                885             890             895

Lys Cys Asp Glu Ala Val Glu Leu Ile His Met Met Ala Glu Asp Gly
            900             905             910

Asp Asn Cys Pro Pro Asn Val Val Ser Tyr Thr Ile Val Ile His Gly
        915             920             925

Leu Phe Lys Glu His Glu Val Gly Lys Ala Phe Thr Leu Phe Cys Glu
    930             935             940

Met Leu Arg Arg Gly Ile Pro Pro Asp Val Met Ile Tyr Arg Ser Ile
945             950             955             960

Ile Asp Val Leu Cys Lys Val Gln Ala Met Asp Lys Ala Glu Lys Val
                965             970             975

Phe Arg Gln Met Leu Asp Asn His Ile Met Pro Asp Cys Thr Thr Tyr
            980             985             990

Thr Ser Leu Leu His Gly Tyr Leu Ser Leu Gly Gln Trp Lys Glu Ala
        995             1000            1005

Val Arg Ile Leu Lys Glu Met Ser Arg Asp Gly Gln Arg Pro Asp Val
    1010            1015            1020

Val Thr Tyr Ser Met Leu Ile Asn Cys Leu Cys Lys Ser Gly Gly His
1025            1030            1035            1040

Ala Glu Ala Arg Glu Ile Phe Asn Ser Met Ile Gln Asn Gly Glu Lys
            1045            1050            1055

Pro Asn Val Ser Thr Tyr Gly Ser Met Leu His Gly Tyr Ala Thr Lys
        1060            1065            1070

Gly Asp Leu Val Glu Met Asn Asn Leu Leu Asp Leu Met Val Gln Asn
    1075            1080            1085

Gly Val Gln Pro Asn His His Ile Phe Asn Ile Gln Ile Tyr Ala His
    1090            1095            1100

Cys Lys Cys Gly Arg Leu Asp Glu Ala Met Leu Thr Phe Asn Lys Met
1105            1110            1115            1120
```

```
Arg Gln Gln Gly Leu Val Pro Asp Ile Val Ser Tyr Gly Thr Val Ile
            1125                1130                1135

Asp Ala Leu Cys Arg Ile Ser Arg Leu Asp Asp Ala Met Val Gln Phe
            1140                1145                1150

Tyr Gln Met Ile Asp Tyr Gly Leu Ser Pro Asn Ile Ile Val Phe Thr
            1155                1160                1165

Thr Leu Ile His Gly Phe Ser Met His Gly Lys Trp Gly Lys Ala Glu
    1170                1175                1180

Glu Leu Phe Tyr Glu Met Met Asp Ser Gly Ile Arg Pro Thr Val Val
1185                1190                1195                1200

Val Phe Val Ala Met Ile Asp Lys Leu Phe Lys Glu Gly Lys Val Thr
            1205                1210                1215

Glu Ala Gln Lys Leu Phe Asp Leu Met Pro Tyr Val Gly Val Lys Pro
            1220                1225                1230

Asp Val Val Ser Tyr Ser Thr Met Ile His Gly Cys Phe Leu Thr Gly
            1235                1240                1245

Lys Pro Asp Glu Val Met Lys Leu Leu Asp Asp Met Leu Leu Ile Gly
            1250                1255                1260

Leu Lys Pro Asn Ala Val Asn Leu Asn Thr Leu Leu Asp Gly Met Leu
1265                1270                1275                1280

Ser Ile Gly Leu Lys Pro Asn Val Ala Thr Phe Trp Arg Ser Tyr Asn
            1285                1290                1295

Ile Val Ser Tyr Leu Pro Ser Ser Met Tyr Leu Ala Asn Thr Asp Arg
            1300                1305                1310

Ile Phe Cys Met Asn Leu Arg Tyr Glu Gln Leu Glu Leu Glu Gly Lys
            1315                1320                1325

Leu Leu Glu Ala Cys Pro Pro Asn Leu Ser Val Ile Phe Arg Ser Arg
            1330                1335                1340

Gly Asp Leu Asp Phe Ala Phe Glu Ser Ile Ser Ala Phe Ser Asp Asn
1345                1350                1355                1360

Gly Glu Asn Gln Gly Tyr Ile Phe Leu Leu Gly Ser Val Glu Asn Ile
            1365                1370                1375

Ser Gly Ser Lys Leu Ala Val Arg Val Gln Trp Gly Lys Lys Leu Met
            1380                1385                1390

Ser Thr Asp Glu Glu Ser Asp Cys Val Val Ile Cys Pro Pro Asn Arg
            1395                1400                1405

Asn Ser Asp His Glu Glu Val Asn Pro Tyr Ala Met Asn Ser His Met
            1410                1415                1420

Asp Thr Asn Gly Leu Glu Asp Val Ser Val Asn Pro Asp Leu Leu Lys
1425                1430                1435                1440

Leu Ile His Gln Gln Glu Ser Ser Val Thr Asn Ser Pro Ala Lys Pro
            1445                1450                1455

Val Ala Arg Gln Gln Gly Ser Ser His Thr Val Pro Glu Pro Cys Thr
            1460                1465                1470

Val Ala Pro Asp Arg Arg Ser Ser Arg Ala Gly Asn Cys Ala Pro Ile
            1475                1480                1485

Pro His Pro Thr Ser Ser Gly Glu Lys Asn Ser Asp Asn Ser Ser Ser
            1490                1495                1500

Ser Gln Arg Ser Met Ala Lys Lys Val Trp Gln Thr Glu Leu Thr Ser
1505                1510                1515                1520

Ile Val Phe Ser Cys Gly Ile Cys Thr Asn Tyr Pro Gly Leu Gly Leu
            1525                1530                1535

Leu Glu His Leu Glu Gly Lys Glu Cys Glu Asn Leu Gln Glu Pro Asn
```

```
                    1540                1545                1550
Ser Asn Gly Arg Ala Gly Lys Thr Lys Lys Thr Thr Val Ala Val Ala
            1555                1560                1565

Pro Thr Phe Val Cys Ala Asn Cys Ala Lys Lys Arg Gly Glu Phe Tyr
        1570                1575                1580

Thr Lys Leu Glu Glu Lys Arg Lys Ala Leu Glu Glu Glu Lys Leu Gln
1585                1590                1595                1600

Ala Glu Ala Arg Lys Arg Val Leu Glu Thr Ile Ser Thr Ala Ile Phe
                1605                1610                1615

Ile Ile Ser Ile Leu Leu Gly Ala Ser Asn Ser Cys Gln Val Thr Lys
            1620                1625                1630

Ile Asn Thr Asp Lys Glu Leu Cys Ser Asp Thr Pro Gln Gln Arg Glu
        1635                1640                1645

Glu Met Ala Val Gln Tyr Ala Ala Ser Cys Ile Ile Thr Thr Leu Gly
    1650                1655                1660

Thr Pro Lys Met Leu Ala Ala Arg His Asn Val Leu Gln Arg Gly Leu
1665                1670                1675                1680

Gln Arg Leu Asp Gln Leu Leu Asn Pro Gly Lys Thr
                1685                1690

<210> SEQ ID NO 18
<211> LENGTH: 959
<212> TYPE: PRT
<213> ORGANISM: Sorghum bicolor

<400> SEQUENCE: 18

Met Asp Glu Pro Pro Pro Arg Pro Ala Leu Asn Ser Ala Ala Ala
1               5                   10                  15

Thr Ser Trp Pro Glu Leu Leu Ala Pro Phe Asp Leu Ser Arg Leu Arg
            20                  25                  30

Ala Thr Leu Ser Ser His Pro Leu Thr Pro Arg Arg Leu Ala Arg Leu
        35                  40                  45

Leu Ala Leu Pro Leu Ser Pro Ala Thr Ser Leu Leu Leu Leu Asp Trp
    50                  55                  60

Tyr Ala Ser Ser His Pro Ala Leu Ser Leu Ser Ser Leu Pro Leu Arg
65                  70                  75                  80

Pro Ile Leu Ala Ser Val Gly Ala Ala Gly Asp Pro Asp Arg Ala Leu
                85                  90                  95

Ala Leu Leu Asp Ser Leu Pro Arg Ser Ser Arg Leu Pro Pro Leu Arg
            100                 105                 110

Glu Ser Leu Leu Leu Pro Leu Leu Arg Ser Leu Pro Pro Gly Arg Ala
        115                 120                 125

Leu His Leu Leu Asp Gln Met Pro Arg Arg Phe Ala Val Thr Pro Ser
    130                 135                 140

Phe Arg Ser Tyr Asn Ala Val Leu Ser Thr Leu Ala Arg Ala Asp Cys
145                 150                 155                 160

His Ala Asp Ala Leu Leu Leu Tyr Arg Arg Met Leu Arg Asp Arg Val
                165                 170                 175

Pro Pro Thr Thr Phe Thr Phe Gly Val Ala Ala Arg Ala Leu Cys Arg
            180                 185                 190

Leu Gly Arg Ala Arg Asp Ala Leu Ala Leu Arg Gly Met Ala Arg
        195                 200                 205

His Gly Cys Val Pro Asp Ala Val Leu Tyr Gln Thr Val Ile His Ala
    210                 215                 220
```

-continued

```
Leu Val Ala Gln Gly Gly Val Ala Glu Ala Ala Thr Leu Leu Asp Glu
225                 230                 235                 240

Met Leu Leu Met Gly Cys Ala Ala Asp Val Asn Thr Phe Asn Asp Val
            245                 250                 255

Val Leu Gly Leu Cys Gly Leu Gly His Val Arg Glu Ala Ala Arg Leu
        260                 265                 270

Val Asp Arg Met Met Met His Gly Cys Thr Pro Ser Val Val Thr Tyr
    275                 280                 285

Gly Phe Leu Leu Arg Gly Leu Cys Arg Thr Arg Gln Ala Asp Glu Ala
290                 295                 300

Tyr Ala Met Leu Gly Arg Val Pro Glu Val Asn Val Val Met Leu Asn
305                 310                 315                 320

Thr Val Ile Arg Gly Cys Leu Ala Glu Gly Lys Leu Ala Arg Ala Thr
            325                 330                 335

Glu Leu Tyr Glu Met Met Gly Ser Lys Gly Cys Pro Pro Asp Val His
        340                 345                 350

Thr Tyr Asn Ile Leu Met His Gly Leu Cys Lys Leu Gly Arg Cys Gly
    355                 360                 365

Ser Ala Val Arg Met Leu Asp Glu Met Glu Glu Lys Gly Cys Ala Pro
370                 375                 380

Asn Ile Val Thr Tyr Ser Thr Leu Leu His Ser Phe Cys Arg Asn Gly
385                 390                 395                 400

Met Trp Asp Asp Ala Arg Ala Met Leu Asp Gln Met Ser Ala Lys Gly
            405                 410                 415

Phe Ser Met Asn Ser Gln Gly Tyr Asn Gly Ile Ile Tyr Ala Leu Gly
        420                 425                 430

Lys Asp Gly Lys Leu Asp Glu Ala Met Arg Leu Val Gln Glu Met Lys
    435                 440                 445

Ser Gln Gly Cys Lys Pro Asp Ile Cys Thr Tyr Asn Thr Ile Ile Tyr
450                 455                 460

His Leu Cys Asn Asn Asp Gln Met Asp Glu Ala Glu His Ile Phe Gly
465                 470                 475                 480

Asn Leu Leu Glu Glu Gly Val Val Ala Asn Gly Ile Thr Tyr Asn Thr
            485                 490                 495

Leu Ile His Ala Leu Leu His Ser Gly Arg Trp Gln Glu Gly Leu Arg
        500                 505                 510

Leu Ala Asn Glu Met Val Leu His Gly Cys Pro Leu Asp Val Val Ser
    515                 520                 525

Tyr Asn Gly Leu Ile Lys Ala Leu Cys Lys Glu Gly Asn Val Asp Arg
530                 535                 540

Ser Met Met Leu Leu Glu Glu Met Met Thr Lys Gly Ile Lys Pro Asn
545                 550                 555                 560

Asn Phe Ser Tyr Asn Met Leu Ile Asn Glu Leu Cys Lys Ala Gly Lys
            565                 570                 575

Val Arg Asp Ala Leu Glu Leu Ser Lys Glu Met Leu Asn Gln Gly Leu
        580                 585                 590

Thr Pro Asp Ile Val Thr Tyr Asn Thr Leu Ile Asn Gly Leu Cys Lys
    595                 600                 605

Val Gly Trp Thr His Ala Ala Leu Asn Leu Leu Glu Lys Leu Pro Asn
610                 615                 620

Glu Asn Val His Pro Asp Ile Val Thr Tyr Asn Ile Leu Ile Ser Trp
625                 630                 635                 640

His Cys Lys Val Arg Leu Leu Asp Asp Ala Ser Met Leu Leu Asp Lys
```

645                 650                 655
Ala Val Ser Gly Gly Ile Val Pro Asn Glu Arg Thr Trp Gly Met Met
                660                 665                 670

Val Gln Asn Phe Val Arg Gln Pro Val Asn Pro Asp Ala Arg Cys Ala
                675                 680             685

Phe Thr Ser Ile Trp Val His Leu Thr Ser Ser Ile Val Thr Val Ala
            690                 695                 700

His Val Asp Leu Val Ser Asn Ile Arg Arg Asp Cys Glu Ile Ala Val
705                 710                 715                 720

Glu Ile Val Met Gly Ser Phe Met Gln Phe Asp Leu Leu Tyr Arg Phe
                725                 730                 735

Leu Gln Arg Cys Asp Leu Phe His Leu Val Thr Glu Ser Met Ala Ser
                740                 745                 750

Pro Leu Arg Leu Glu Tyr Tyr Ile Gln Tyr Tyr Leu Val Arg Leu Cys
                755                 760                 765

Gly Tyr Phe Gln Ser Val Glu Val Arg Phe His Val Ala Leu Ala Thr
            770                 775                 780

Cys Gln Ala Gln Gly Lys Ala Ser Asp Pro Ala Ala Ser Cys Val Ser
785                 790                 795                 800

Gly Ala Leu Pro Thr Ala Ser Asn Leu Gln Pro Gln Arg Pro Ala Cys
                805                 810                 815

Ala Ala Ala Arg Pro Gln Met His Asp Val Val Val Val Val Val Ala
                820                 825                 830

Ser Glu Ala Phe Pro Lys Ala Arg Cys Val His Gly His Gly Gln Gly
            835                 840                 845

Gly Arg Pro Tyr Glu Gly Leu Ser Asp Glu Val Ser Phe Ala Ala His
850                 855                 860

Thr Pro Arg Pro Gly Ala Ser Phe Arg Cys Thr Thr Thr Trp Pro Ala
865                 870                 875                 880

Trp Pro Ser Gln Tyr Tyr Glu Ser Thr Thr Ser Ala Ala Leu Gly Cys
                885                 890                 895

Pro His Gly Gln Trp Arg Trp Pro His Thr Ala Asp Gly Thr Val Thr
            900                 905                 910

Leu Ser Leu Val Val Leu Ser Val Lys Met Asp Val Pro Pro Leu
            915                 920                 925

Val Arg Ser Ala Leu Leu Gly Ala Gln Ala Ser Thr Cys Ser Val Leu
            930                 935                 940

Pro Met Leu Leu Gln Cys Ser Leu Gly Arg Leu Pro Gly Gly Asn
945                 950                 955

<210> SEQ ID NO 19
<211> LENGTH: 696
<212> TYPE: PRT
<213> ORGANISM: Sorghum bicolor

<400> SEQUENCE: 19

Met Ser Ser Arg Thr Cys Leu Lys Lys Leu Lys Arg Ile Ile Gly Arg
 1               5                  10                  15

Arg Ile Arg Ser Gly Ser Leu Ser Ala Glu Ala Ala Arg Gln Leu Trp
                20                  25                  30

Asn Glu Val Leu Pro Ser Ile Gln Tyr Arg Ser Pro Pro Ala Ala
            35                  40                  45

Ser Ala Ala Ala Arg Arg Trp Arg Ala Asp Arg Arg Ser Trp Glu
50                  55                  60

-continued

```
Leu Glu Gln Phe Ile Gly Glu Cys Tyr Arg Ser Gly Asp Leu Gly Pro
 65                  70                  75                  80

Glu Asp Ala Leu Asp Leu Phe Asp Glu Leu Leu Gln Arg Ala Arg Pro
                 85                  90                  95

Gly Ser Ile Tyr Ala Leu Asn Gln Leu Leu Thr Thr Val Ala Arg Ala
            100                 105                 110

Pro Val Ser Ser Val Arg Asp Gly Pro Ala Leu Ala Val Ser Met
        115                 120                 125

Phe Asn Arg Met Ala Arg Ala Gly Ala Lys Lys Val Ala Pro Asp Ile
130                 135                 140

Ala Thr Phe Gly Ile Leu Ile Ser Cys Cys Asp Ala Gly Cys Leu
145                 150                 155                 160

Asn Leu Gly Phe Ala Ala Leu Gly Gln Ile Ile Lys Thr Gly Leu Arg
                165                 170                 175

Ala Gln Ala Val Thr Phe Thr Pro Leu Leu Arg Thr Leu Cys Ala Glu
            180                 185                 190

Lys Arg Thr Ser Asp Ala Met Asn Ile Val Leu Arg Arg Met Pro Glu
        195                 200                 205

Leu Gly Cys Thr Pro Asp Val Phe Ser Tyr Thr Thr Leu Leu Lys Gly
210                 215                 220

Leu Cys Ala Glu Lys Lys Cys Glu Glu Ala Ala Glu Leu Ile His Met
225                 230                 235                 240

Met Ala Glu Asp Gly Asp Asn Cys Pro Pro Asn Val Val Ser Tyr Thr
                245                 250                 255

Thr Val Ile His Gly Phe Phe Lys Glu Gly Asp Val Gly Lys Ala Tyr
            260                 265                 270

Thr Leu Phe Cys Lys Met Leu Asp His Gly Ile Pro Pro Asn Val Val
        275                 280                 285

Thr Cys Asn Ser Val Ile Asp Gly Leu Cys Lys Val Gln Ala Met Asp
290                 295                 300

Lys Ala Glu Ala Val Leu Gln Gln Met Ile Asp Glu His Ile Met Pro
305                 310                 315                 320

Asn Cys Thr Thr Tyr Asn Ser Leu Ile His Gly Tyr Leu Ser Ser Gly
                325                 330                 335

Gln Trp Thr Glu Ala Val Arg Ile Leu Lys Glu Met Ser Arg Asp Gly
            340                 345                 350

Gln Arg Pro Asn Val Val Thr Tyr Ser Met Leu Ile Asp Cys Leu Cys
        355                 360                 365

Lys Ser Gly Leu His Ala Glu Ala Arg Glu Ile Phe Asn Ser Met Ile
370                 375                 380

Gln Ser Gly Gln Lys Pro Asn Ala Ser Thr Tyr Gly Ser Leu Leu His
385                 390                 395                 400

Gly Tyr Ala Thr Glu Gly Asn Leu Val Asp Met Asn Asn Val Lys Asp
                405                 410                 415

Leu Met Val Gln Asn Gly Met Arg Pro Gly Arg His Val Phe Asn Ile
            420                 425                 430

Glu Ile Tyr Ala Tyr Cys Lys Cys Gly Arg Leu Asp Glu Ala Ser Leu
        435                 440                 445

Thr Phe Asn Lys Met Gln Gln Gly Phe Met Pro Asp Ile Val Ala
450                 455                 460

Tyr Thr Thr Val Ile Asp Gly Leu Cys Lys Ile Gly Arg Leu Asp Asp
465                 470                 475                 480

Ala Met Ser Arg Phe Cys Gln Met Ile Asp Asp Gly Leu Ser Pro Asp
```

```
                485                 490                 495
Ile Ile Thr Phe Asn Thr Leu Ile His Gly Phe Ala Leu His Gly Lys
                500                 505                 510

Trp Glu Lys Ala Glu Glu Leu Phe Tyr Glu Met Met Asp Arg Gly Ile
                515                 520                 525

Pro Pro Asn Val Asn Thr Phe Asn Ser Met Ile Asp Lys Leu Phe Lys
                530                 535                 540

Glu Gly Lys Val Thr Glu Ala Arg Lys Leu Phe Asp Leu Met Pro Arg
545                 550                 555                 560

Ala Gly Ala Lys Pro Asn Val Val Ser Tyr Asn Thr Met Ile His Gly
                565                 570                 575

Tyr Phe Ile Ala Gly Glu Val Gly Glu Val Met Lys Leu Leu Asp Asp
                580                 585                 590

Met Leu Leu Ile Gly Leu Lys Pro Thr Ala Val Thr Phe Asn Thr Leu
                595                 600                 605

Leu Asp Gly Met Val Ser Met Gly Leu Lys Pro Asp Val Val Thr Cys
                610                 615                 620

Lys Thr Leu Ile Asp Ser Cys Cys Glu Asp Gly Arg Ile Glu Asp Ile
625                 630                 635                 640

Leu Thr Leu Phe Arg Glu Met Leu Gly Lys Ala Asp Lys Thr Asp Thr
                645                 650                 655

Ile Thr Glu Asn Ile Lys Leu Arg Gly Val Thr Val Lys Ala Ser Tyr
                660                 665                 670

His Cys Ser Ser Val Val Ile Ser Leu Lys Ala Leu Glu Val Val Thr
                675                 680                 685

Gln Ala Gly Ala Ile Ser Cys Ile
                690                 695

<210> SEQ ID NO 20
<211> LENGTH: 532
<212> TYPE: PRT
<213> ORGANISM: Sorghum bicolor

<400> SEQUENCE: 20

Met Ala Arg Ala Gly Ala Lys Lys Val Ala Pro Asp Ile Ala Thr Phe
1               5                   10                  15

Gly Ile Leu Ile Ser Cys Cys Asp Ala Gly Cys Leu Asn Leu Gly
                20                  25                  30

Phe Ala Ala Leu Gly Gln Ile Ile Lys Thr Gly Leu Arg Ala Asp Ala
                35                  40                  45

Val Ala Phe Thr Pro Leu Leu Arg Thr Leu Cys Ala Lys Lys Arg Thr
                50                  55                  60

Ser Asp Ala Met Asn Ile Val Leu Arg Arg Met Pro Glu Leu Gly Cys
65                  70                  75                  80

Thr Pro Asp Val Phe Ser Tyr Ser Thr Leu Leu Lys Gly Leu Cys Ala
                85                  90                  95

Glu Lys Lys Cys Glu Glu Ala Ala Glu Leu Ile His Met Met Ala Glu
                100                 105                 110

Asp Gly Asp Asn Cys Pro Pro Asp Val Val Ser Tyr Ser Thr Val Ile
                115                 120                 125

His Gly Phe Phe Lys Glu Gly Asp Val Gly Lys Ala Tyr Thr Leu Phe
                130                 135                 140

Cys Lys Met Leu Asp His Gly Ile Pro Pro Asn Val Val Thr Cys Asn
145                 150                 155                 160
```

```
Ser Val Ile Asp Gly Leu Cys Lys Val Gln Ala Met Asp Lys Ala Glu
            165                 170                 175

Ala Val Leu Gln Gln Met Ile Asp Glu His Ile Met Pro Asn Cys Thr
        180                 185                 190

Thr Tyr Asn Ser Leu Ile His Gly Tyr Leu Ser Ser Gly Gln Trp Thr
    195                 200                 205

Glu Ala Val Arg Ile Leu Lys Glu Met Ser Arg Asp Gly Gln Arg Pro
210                 215                 220

Asn Val Val Thr Tyr Asn Met Leu Ile Asp Cys Leu Cys Lys Ser Gly
225                 230                 235                 240

Phe His Ala Glu Ala Arg Glu Ile Phe Asn Ser Met Ile Gln Ser Gly
                245                 250                 255

Pro Lys Pro Asp Ala Thr Thr Tyr Gly Ser Leu Leu His Gly Tyr Ala
            260                 265                 270

Thr Glu Gly Asn Leu Val Glu Met Asn Asn Val Lys Asp Leu Met Val
        275                 280                 285

Gln Asn Gly Met Arg Ser Asn His His Thr Phe Ser Ile Glu Ile Tyr
    290                 295                 300

Ala Tyr Cys Lys Cys Gly Arg Leu Asp Glu Ala Ser Leu Thr Phe Ile
305                 310                 315                 320

Lys Met Gln Gln Leu Gly Phe Met Pro Asp Ile Val Thr Tyr Thr Thr
                325                 330                 335

Val Ile Asp Gly Leu Cys Lys Ile Gly Arg Leu Asp Asp Ala Met Ser
            340                 345                 350

Arg Phe Cys Gln Met Ile Asp Asp Gly Leu Ser Pro Asn Ile Ile Thr
        355                 360                 365

Phe Thr Thr Leu Ile His Gly Phe Ser Met Tyr Gly Lys Trp Glu Lys
    370                 375                 380

Ala Glu Glu Leu Phe Tyr Glu Met Met Asp Arg Gly Ile Pro Pro Asp
385                 390                 395                 400

Val Thr Ile Phe Thr Ala Met Ile Asp Arg Leu Phe Lys Glu Gly Lys
                405                 410                 415

Val Thr Glu Ala Gln Lys Leu Phe Asp Leu Met Pro Arg Ala Gly Ala
            420                 425                 430

Lys Pro Asn Val Val Ser Tyr Asn Thr Met Ile His Gly Tyr Phe Ile
        435                 440                 445

Ala Gly Glu Val Gly Glu Val Met Lys Leu Leu Asp Asp Met Leu Leu
    450                 455                 460

Ile Gly Leu Lys Pro Thr Ala Val Thr Phe Asn Thr Leu Leu Asp Gly
465                 470                 475                 480

Met Val Ser Met Gly Leu Lys Pro Asp Val Asp Thr Cys Lys Thr Leu
                485                 490                 495

Ile Asp Ser Cys Cys Glu Asp Gly Arg Ile Glu Asp Ile Leu Thr Leu
            500                 505                 510

Phe Arg Glu Met Leu Gly Lys Ala Asp Lys Thr Asp Thr Ile Thr Glu
        515                 520                 525

Asn Ile Lys Leu
    530

<210> SEQ ID NO 21
<211> LENGTH: 626
<212> TYPE: PRT
<213> ORGANISM: Sorghum bicolor

<400> SEQUENCE: 21
```

-continued

```
Met Phe Tyr Thr Arg Thr Leu Gln Gly Ser Arg Pro Val Arg Gln Arg
 1               5                  10                  15

Gly Arg Arg Tyr Glu Asn Arg Pro Ser Cys Glu Leu Glu Arg Phe Ile
                20                  25                  30

Gly Glu Cys Phe Arg Ser Gly Asp Leu Asp Pro Glu Asp Ala Leu Asp
            35                  40                  45

Leu Phe Asp Glu Leu Leu Pro Gln Ala Arg Gln Gly Ser Val Tyr Ala
        50                  55                  60

Leu Thr Arg Leu Leu Thr Thr Val Ala Arg Ala Pro Val Ser Ser Ala
65                  70                  75                  80

Val Pro Asn Gly Pro Ala Leu Ala Val Ser Met Phe Asn Arg Met Ala
                85                  90                  95

Arg Ala Gly Ser Lys Lys Val Ala Pro Thr Thr Val Thr Tyr Thr Ile
               100                 105                 110

Leu Ile Ser Cys Cys Cys Tyr Val Gly Cys Leu Asn Leu Ala Phe Ala
           115                 120                 125

Ala Leu Gly Gln Ile Ile Lys Thr Gly Leu Arg Ala Asn Ala Ile Ser
       130                 135                 140

Phe Thr Pro Ile Leu Arg Thr Leu Cys Ala Glu Lys Arg Thr Ser Asp
145                 150                 155                 160

Ala Met Asn Ile Val Ile Arg Trp Thr Pro Lys Leu Gly Cys Thr Pro
               165                 170                 175

Asp Val Phe Ser Tyr Thr Val Leu Leu Lys Gly Leu Cys Asp Glu Lys
           180                 185                 190

Lys Cys Glu Glu Ala Val Asp Leu Ile His Met Met Ala Glu Asp Gly
       195                 200                 205

Asp His Cys Pro Pro Asn Val Val Ser Tyr Thr Thr Val Ile His Gly
210                 215                 220

Phe Phe Lys Glu Asp Glu Val Gly Lys Ala Tyr Thr Leu Phe Cys Glu
225                 230                 235                 240

Met Leu Asp Arg Gly Ile Pro Pro Asp Val Val Thr Cys Asn Ser Ile
               245                 250                 255

Ile Asp Gly Leu Cys Lys Val Gln Ala Met Asp Lys Ala Glu Glu Val
           260                 265                 270

Leu Arg Gln Met Phe Asp Lys His Ile Met Pro Asp Cys Thr Thr Tyr
       275                 280                 285

Asn Ser Leu Val His Gly Tyr Leu Ser Ser Gly Gln Leu Lys Glu Ala
290                 295                 300

Val Arg Ile Leu Lys Gln Met Ser Arg His Gly Gln Pro Pro Asn Gly
305                 310                 315                 320

Val Thr Tyr Ser Met Leu Ile Asp Cys Leu Cys Lys Phe Gly Gly His
               325                 330                 335

Thr Glu Ala Arg Glu Ile Leu Asn Ser Met Ile Gln Ser Arg Gly Asn
           340                 345                 350

Pro Asn Val Ala Thr Tyr Gly Gly Leu Leu His Gly Tyr Ala Thr Lys
       355                 360                 365

Gly Asp Leu Val Glu Met Asn Asn Leu Ile Asp Leu Met Val Gln Asn
370                 375                 380

Gly Val Arg Pro Asp His His Ile Phe Asn Ile Gln Ile Tyr Ala Tyr
385                 390                 395                 400

Val Lys Cys Gly Arg Leu Asp Glu Ala Met Leu Thr Phe Asn Lys Met
               405                 410                 415
```

Arg Gln Gln Gly Leu Met Pro Asp Ile Ile Ser Tyr Gly Thr Met Ile
                420                 425                 430

Asp Gly Leu Cys Lys Ile Gly Arg Leu Asp Ala Ala Met Ser Gln Phe
            435                 440                 445

Cys Gln Met Ile Asp Asp Gly Leu Ser Pro Asp Ile Val Val Phe Thr
        450                 455                 460

Asn Leu Ile His Gly Phe Ser Met Tyr Gly Lys Trp Glu Lys Ala Glu
465                 470                 475                 480

Glu Leu Phe Tyr Glu Met Met Asp Arg Gly Ile Arg Pro Thr Val Val
                485                 490                 495

Val Phe Thr Thr Met Ile Asp Lys Leu Phe Lys Glu Gly Lys Val Thr
            500                 505                 510

Glu Ala Lys Thr Leu Phe Asp Leu Met Pro Ile Ala Ser Val Lys Pro
        515                 520                 525

Asn Val Val Ser Tyr Asn Ala Ile Ile His Gly Tyr Phe Leu Ala Gly
530                 535                 540

Lys Leu Asp Glu Val Leu Lys Leu Leu Asp Asp Met Leu Ser Val Gly
545                 550                 555                 560

Leu Lys Pro Asn Ala Val Thr Phe Asn Thr Leu Leu Asp Asp Met Leu
                565                 570                 575

Ser Met Gly Leu Lys Pro Asp Val Ala Thr Cys Asn Thr Leu Ile Asp
            580                 585                 590

Ser Cys Cys Glu Asp Gly Arg Ile Glu Asp Val Leu Thr Leu Phe Arg
        595                 600                 605

Glu Met Leu Ser Lys Ala Ala Lys Thr Asp Thr Val Thr Glu Asn Ile
610                 615                 620

Ile Ser
625

<210> SEQ ID NO 22
<211> LENGTH: 650
<212> TYPE: DNA
<213> ORGANISM: Sorghum bicolor

<400> SEQUENCE: 22
gaaggctaga tgaggcaagc cttactttta acaaaatgca gcagctagga ttcatgccag      60
acatagtcac ctacaccacg gttatagatg ggctttgcaa gataggccgg ctggacgatg     120
caatgtcccg attctgtcag atgattgatg atggattgtc tcccaatatc ataacattta     180
cgaccctgat tcatgggttt tctatgtatg gcaaatggga gaaggctgag gaactatttt     240
atgagatgat ggatagaggc attcctcctg atgtcactat cttcagtgca atgatagata     300
ggctattcaa agaaggaaag gttacagagg cccaaaaact ctttgatttg atgccacgtg     360
caggagctaa acctgatgtt gtttcttata atataatgat tcatgggtat ttcatagctg     420
gtgaagtggg cgaagtgatg aagctccttg atgagatgct cttgattggc ttgaaacccg     480
atgctgttat ttttgctact ttatttgatg gcatggtctc taagggattg aatcctgatg     540
ttgacacatg taagactttg attgatagct gctgtgaaga tgacaggata gaggatatat     600
taactctgtt ccgagaaatg ttgagcaagg ctgataagac tgacactatc               650

<210> SEQ ID NO 23
<211> LENGTH: 650
<212> TYPE: DNA
<213> ORGANISM: Sorghum bicolor

<400> SEQUENCE: 23

```
gaaggctaga tgaggcaagc cttactttta acaaaatgca gcagctagga ttcatgccag      60
acatagtcac ctacaccacg gttatagatg ggctttgcaa gataggccgg ctggacgatg     120
caatgtcccg attctgtcag atgattgatg atggattgtc tcccaatatc ataacattta     180
cgaccctgat tcatgggttt tctatgtatg gcaaatggga gaaggctgag gaactatttt     240
atgagatgat ggatagaggc attcctcctg atgtcactat cttcagtgca atgatagata     300
ggctattcaa agaaggaaag gttacggagg cccgaaaact ctttgatttg atgccacgtg     360
caggagctaa acctaatgtt gtttcttata atacaatgat tcatgggtat ttcatagctg     420
gtgaagtggg cgaagtgatg aagctccttg atgagatgct cttgattggc ttgaaacccg     480
atgctgtttt ttttgctact ttatttgatg gcatggtctc taagggattg aatcctgatg     540
ttgacacatg taagactttg attgatagct gctgtgaaga tgacaggata gaggatatat     600
taactctgtt ccgagaaatg ttgagcaagg ctgataagac tgacactatc                650
```

<210> SEQ ID NO 24
<211> LENGTH: 650
<212> TYPE: DNA
<213> ORGANISM: Sorghum bicolor

<400> SEQUENCE: 24

```
gaaggctaga tgaggcaagc cttactttta acaaaatgca gcagctagga ttcatgccag      60
acatagtcac ctacaccacg gttatagatg ggctttgcaa gataggccgg ctggacgatg     120
caatgtcccg attctgtcag atgattgatg atggattgtc tcccaatatc ataacattta     180
cgaccctgat tcatgggttt tctatgtatg gcaaatggga gaaggctgag gaactatttt     240
atgagatgat ggatagaggc attcctccta atgtcaatac gttcaattca atgatagata     300
ggctattcaa agaaggaaag gttacggagg cccgaaaact ctttgatttg atgccacgtg     360
caggagctaa acctaatgtt gtttcttata atacaatgat tcatgggtat ttcatagctg     420
gtgaagtggg cgaagtgatg aagctccttg atgatatgct cttgattggc ttgaaaccca     480
atgctgttaa ccttaatact ttacttgatg gcatgctctc tattggcttg aaaccaaatg     540
ttgacacatg taagactttg attgatagct gctgtgaaga tgacaggata gaggatatat     600
taactctgtt ccgagaaatg ttgagcaagg ctgataagac tgacactatc                650
```

<210> SEQ ID NO 25
<211> LENGTH: 650
<212> TYPE: DNA
<213> ORGANISM: Sorghum bicolor

<400> SEQUENCE: 25

```
gaaggctaga tgaggcaagc cttactttta acaaaatgca gcagctagga ttcatgccag      60
acatagtcac ctacaccacg gttatagatg ggctttgcaa gataggccgg ctggacgatg     120
caatgtcccg attctgtcag atgattgatg atggattgtc tcccaatatc ataacattta     180
cgaccctgat tcatgggttt tctatgtatg gcaaatggga gaaggctgag gaactatttt     240
atgagatgat ggatagaggc attcctcctg atgtcactat cttcagtgca atgatagata     300
ggctattcaa agaaggaaag gttacagagg cccaaaaact cttttatttg atgccacgtg     360
caggagctaa acctaatgtt gtttcttata atacaatgat tcatgggtat ttcatagctg     420
gtgaagtggg cgaagtgatg aagctccttg atgagatgct cttgattggc ttgaaacccg     480
atgctgtttt ttttgctact ttatttgatg gcatggtctc taagggattg aatcctgatg     540
```

```
ttgacacatg taagactttg attgatagct gctgtgaaga tgacaggata gaggatatat    600
taactctgtt ccgagaaatg ttgagcaagg ctgataagac tgacactatc              650
```

<210> SEQ ID NO 26
<211> LENGTH: 27
<212> TYPE: DNA
<213> ORGANISM: Artificial Sequence
<220> FEATURE:
<223> OTHER INFORMATION: primer

<400> SEQUENCE: 26

```
cattcctcct gatgtcacta tcttcag                                        27
```

<210> SEQ ID NO 27
<211> LENGTH: 25
<212> TYPE: DNA
<213> ORGANISM: Artificial Sequence
<220> FEATURE:
<223> OTHER INFORMATION: primer

<400> SEQUENCE: 27

```
tctctattga acccttttgg ccatc                                          25
```

<210> SEQ ID NO 28
<211> LENGTH: 17
<212> TYPE: DNA
<213> ORGANISM: Artificial Sequence
<220> FEATURE:
<223> OTHER INFORMATION: probe

<400> SEQUENCE: 28

```
tcaacatttg gtttcaa                                                   17
```

<210> SEQ ID NO 29
<211> LENGTH: 16
<212> TYPE: DNA
<213> ORGANISM: Artificial Sequence
<220> FEATURE:
<223> OTHER INFORMATION: probe

<400> SEQUENCE: 29

```
caacatcagg attcaa                                                    16
```

<210> SEQ ID NO 30
<211> LENGTH: 25
<212> TYPE: DNA
<213> ORGANISM: Artificial Sequence
<220> FEATURE:
<223> OTHER INFORMATION: primer

<400> SEQUENCE: 30

```
ggcgaagtga tgaagctcct tgatg                                          25
```

<210> SEQ ID NO 31
<211> LENGTH: 26
<212> TYPE: DNA
<213> ORGANISM: Artificial Sequence
<220> FEATURE:
<223> OTHER INFORMATION: primer

<400> SEQUENCE: 31

```
agcagctatc aatcaaagtc ttacat                                         26
```

<210> SEQ ID NO 32
<211> LENGTH: 16

```
<212> TYPE: DNA
<213> ORGANISM: Artificial Sequence
<220> FEATURE:
<223> OTHER INFORMATION: probe

<400> SEQUENCE: 32
caacatcagg tttagc                                                    16

<210> SEQ ID NO 33
<211> LENGTH: 18
<212> TYPE: DNA
<213> ORGANISM: Artificial Sequence
<220> FEATURE:
<223> OTHER INFORMATION: probe

<400> SEQUENCE: 33
caacattagg tttagctc                                                  18

<210> SEQ ID NO 34
<211> LENGTH: 29
<212> TYPE: DNA
<213> ORGANISM: Artificial Sequence
<220> FEATURE:
<223> OTHER INFORMATION: primer

<400> SEQUENCE: 34
gataggctat tcaaagaagg aaaggttac                                      29

<210> SEQ ID NO 35
<211> LENGTH: 25
<212> TYPE: DNA
<213> ORGANISM: Artificial Sequence
<220> FEATURE:
<223> OTHER INFORMATION: primer

<400> SEQUENCE: 35
gggtttcaag ccaatcaaga gcatc                                          25

<210> SEQ ID NO 36
<211> LENGTH: 22
<212> TYPE: DNA
<213> ORGANISM: Artificial Sequence
<220> FEATURE:
<223> OTHER INFORMATION: primer

<400> SEQUENCE: 36
gcctcaagcc tcctagccaa at                                             22

<210> SEQ ID NO 37
<211> LENGTH: 22
<212> TYPE: DNA
<213> ORGANISM: Artificial Sequence
<220> FEATURE:
<223> OTHER INFORMATION: primer

<400> SEQUENCE: 37
catttcgtgg aactctgtcg gg                                             22

<210> SEQ ID NO 38
<211> LENGTH: 332
<212> TYPE: DNA
<213> ORGANISM: Sorghum bicolor

<400> SEQUENCE: 38
cctcgaggga tcgtcactgt gggtttgaac ccacccgcgt cgctgatgtc atgtcccccc    60
```

```
accgtcatgc tcaagcctc ctagccaaat ctggcgccac acactcttga aggaaaagag    120
agatgacaat ccacccatgg agaaaatcaa ccgaggagag agagagagag agagagagag    180
agagagagag agagagagag agatttggga ttcacccgtt gccccgacag agttccacga    240
aatgtggcta tggccactaa atccgggccc tctagatgcg ccgcatgca taagcttgag     300 ttatttctat agtgtccacc caattagctt gg                                  332
```

```
<210> SEQ ID NO 39
<211> LENGTH: 22
<212> TYPE: DNA
<213> ORGANISM: Artificial Sequence
<220> FEATURE:
<223> OTHER INFORMATION: primer

<400> SEQUENCE: 39
cgccacacac tcttgaagga aa                                              22

<210> SEQ ID NO 40
<211> LENGTH: 20
<212> TYPE: DNA
<213> ORGANISM: Artificial Sequence
<220> FEATURE:
<223> OTHER INFORMATION: primer

<400> SEQUENCE: 40
gtggactctg tcgggcact                                                  20

<210> SEQ ID NO 41
<211> LENGTH: 342
<212> TYPE: DNA
<213> ORGANISM: Sorghum bicolor
<220> FEATURE:
<221> NAME/KEY: misc_feature
<222> LOCATION: 3, 44, 48, 56, 66, 75, 80, 82, 94, 98, 103, 145, 147,
      173, 263, 283, 298
<223> OTHER INFORMATION: n = A,T,C or G

<400> SEQUENCE: 41
```

```
gcntcgcgac tcgaatcgtc gactcgaggg atccaaccat ggancccntc gtgganccca     60
accgcntcgc tgatntcttn tnccctcacc gtcntgcntc aancctccta gccaaatctg    120
gcgccacaca ctcttgaagg aaaananaga tgacaatcca accatggaga aantccccga    180
aggagagaga gagagagaga gagagagaga gagagagaga gagagagaga ttggggattc    240
ccagtgcccc gacagagtcc acnaatgtgg ctatggccac tanatccggg ccctctanat    300
gcggccgcat gcataagctt gaattattct atagtgtccc ta                       342
```

```
<210> SEQ ID NO 42
<211> LENGTH: 22
<212> TYPE: DNA
<213> ORGANISM: Artificial Sequence
<220> FEATURE:
<223> OTHER INFORMATION: primer

<400> SEQUENCE: 42
atggatgagc aagacacgat gc                                              22

<210> SEQ ID NO 43
<211> LENGTH: 22
<212> TYPE: DNA
<213> ORGANISM: Artificial Sequence
<220> FEATURE:
<223> OTHER INFORMATION: primer
```

<400> SEQUENCE: 43
gtcctcccac aagacaaccc ac                                          22

<210> SEQ ID NO 44
<211> LENGTH: 417
<212> TYPE: DNA
<213> ORGANISM: Sorghum bicolor
<220> FEATURE:
<221> NAME/KEY: misc_feature
<222> LOCATION: 17, 35, 43, 45, 61, 66, 128, 133, 151, 212, 232, 243,
      247, 287, 313, 318, 356, 374, 393, 409
<223> OTHER INFORMATION: n = A,T,C or G

<400> SEQUENCE: 44
cattggcaat cggcgantcg attcgtcgac tcganggatc tananggagg gagggaggaa   60
ncaaancaaa gccagcaggc gatatggatg agcaagacac gatgcctcct gtgccctata  120
tatggaanat tanggaacag ggagggcgta nctagcccaa tttcctctga ccttcggcgc  180
tgtcgtcgtc gtctatggtg gaattgaaag angtttgtgg aggaagcaac anaaggatac  240
ccnaaanaag agggagagag agagagagag agagagagag gattatncct gaatggggac  300 aggggggag ganaaaangt gtttggtgtg ggttgtcttg tgggaggaca gtgcanctga  360
tccgggccct ctanatgcgg ccgcatgcat aancttgagt attctatant gtccta      417

<210> SEQ ID NO 45
<211> LENGTH: 26
<212> TYPE: DNA
<213> ORGANISM: Artificial Sequence
<220> FEATURE:
<223> OTHER INFORMATION: primer

<400> SEQUENCE: 45
gacccatatg tggtttagtc gcaaag                                      26

<210> SEQ ID NO 46
<211> LENGTH: 26
<212> TYPE: DNA
<213> ORGANISM: Artificial Sequence
<220> FEATURE:
<223> OTHER INFORMATION: primer

<400> SEQUENCE: 46
gcacaatctt cgcctaaatc aacaat                                      26

<210> SEQ ID NO 47
<211> LENGTH: 22
<212> TYPE: DNA
<213> ORGANISM: Artificial Sequence
<220> FEATURE:
<223> OTHER INFORMATION: primer

<400> SEQUENCE: 47
tcgtggattt gcattccttg aa                                          22

<210> SEQ ID NO 48
<211> LENGTH: 22
<212> TYPE: DNA
<213> ORGANISM: Artificial Sequence
<220> FEATURE:
<223> OTHER INFORMATION: primer

<400> SEQUENCE: 48
gaatgtgcct tgtttctgtg cg                                          22

<210> SEQ ID NO 49
<211> LENGTH: 682
<212> TYPE: DNA
<213> ORGANISM: Sorghum bicolor
<220> FEATURE:
<221> NAME/KEY: misc_feature
<222> LOCATION: 403, 427, 473, 476, 517, 550, 566, 628, 647, 660, 663, 668
<223> OTHER INFORMATION: n = A,T,C or G

<400> SEQUENCE: 49

```
ggcaagtcgg ccgagctcga attcgtcgac tcgagggatc atgaaactac tactcaaaat      60
tggagttgag aacattgatg ttgttaccct tctggctgac tctaataatc caggatataa     120
tcgtggattt gcattccttg aactggagac ttataaagat gcacagatag catacaaaaa     180
gctttcaagg aaagatgttt ttggcaaggg tttaaatata acagttgcat gggccgaacc     240
attgaatggt cgagatgaaa aacagatgca gaaggtctct ctctctctct ctctctctct     300
ctcacacaca cacacacaca ccacacgcac gcacagaaac aaggcacatt catggacgaa     360
cacatacata ggctgtttgt gatctaatga agctgaatat tcntcgcaat gcttgcatat     420
agattanccc tttgcacgtg caggggaaca caacaatcaa gaggaattag cangcnatgt     480
tttttgaaat ctgcaaccaa tttacctgca cctacanagt acaattgtgc tgactccagg     540
gctaaagccn ccatattaca tgcgantggc agccggtatt ttttgtgata atagtggcaa     600
aatgagaagc tagatccggg ccctctanat gccgccgcct gcataanctt gaattttctn     660
tantgtcncc taaatcgctt gg                                              682
```

<210> SEQ ID NO 50
<211> LENGTH: 18
<212> TYPE: DNA
<213> ORGANISM: Artificial Sequence
<220> FEATURE:
<223> OTHER INFORMATION: primer

<400> SEQUENCE: 50

```
acataaaagc ccctcttc                                                    18
```

<210> SEQ ID NO 51
<211> LENGTH: 19
<212> TYPE: DNA
<213> ORGANISM: Artificial Sequence
<220> FEATURE:
<223> OTHER INFORMATION: primer

<400> SEQUENCE: 51

```
ctttcacacc ctttattca                                                   19
```

<210> SEQ ID NO 52
<211> LENGTH: 22
<212> TYPE: DNA
<213> ORGANISM: Artificial Sequence
<220> FEATURE:
<223> OTHER INFORMATION: primer

<400> SEQUENCE: 52

```
gcaggagagc tgcgtatcat tg                                               22
```

<210> SEQ ID NO 53
<211> LENGTH: 20
<212> TYPE: DNA
<213> ORGANISM: Artificial Sequence
<220> FEATURE:

<223> OTHER INFORMATION: primer

<400> SEQUENCE: 53
ggtcggtcgg tcgttgtttc                                        20

<210> SEQ ID NO 54
<211> LENGTH: 624
<212> TYPE: DNA
<213> ORGANISM: Sorghum bicolor
<220> FEATURE:
<221> NAME/KEY: misc_feature
<222> LOCATION: 159, 318, 347, 372, 386, 396, 420, 421, 426, 433, 439,
      447, 481, 501, 537, 574, 580, 582, 588, 592, 602, 604, 610, 619
<223> OTHER INFORMATION: n = A,T,C or G

<400> SEQUENCE: 54
ggcaatcggc cgagctcgaa ttcgtcgact cgaggatcca tgtttgtctg cttttattac      60
attaaataaa taaataaggg gggaatggac tttcagaaca aagtgactgt ctaacttcga     120
accaaaacat aatgcaacct aaaatgatgc agcacatang aaatgttgcc ttgttcttct     180
tcctcgaagt atggagagca tgtttcttca tggcatggga ctattgcctt gtccttcttc     240
ctcatagtat ccttgttcta cttcctcata atagtctttt tttttctcga acacgcagga    300
gagctgcgta tcattgtntt aaaagaagga agaggagtct aacatanacc cacacacaca    360
cactcacaca cnatcagaca aacacnctct cccacncaca tttctacgcc aaccttgatn    420
nctaanactt aancaccana atctgangaa acaacgaccg accgaccgtg agcaaggaga    480
naaccttttg ctcctgacca ncaccaccag tggggcttca tttctaacca tacttanggg    540
ctgcgccatg tttggatccg ggcctctaaa tgcngccgcn tncctaanct tnaattattc    600
tntnctgtcn cctaaatanc ttgg                                          624

<210> SEQ ID NO 55
<211> LENGTH: 22
<212> TYPE: DNA
<213> ORGANISM: Artificial Sequence
<220> FEATURE:
<223> OTHER INFORMATION: primer

<400> SEQUENCE: 55
agagtgcaag aagcatgagc ca                                       22

<210> SEQ ID NO 56
<211> LENGTH: 22
<212> TYPE: DNA
<213> ORGANISM: Artificial Sequence
<220> FEATURE:
<223> OTHER INFORMATION: primer

<400> SEQUENCE: 56
agtagtccag caaaacggct gc                                       22

<210> SEQ ID NO 57
<211> LENGTH: 874
<212> TYPE: DNA
<213> ORGANISM: Sorghum bicolor

<400> SEQUENCE: 57
ctgcagcatg tatattatgg tcacacaaaa gtagcgggat actacaatga cattccagct      60
gagtttattc tgtatcatca taatgttcat gatctatgaa caggcacagg cctgaggatc     120
ttcctcgaat tcagcgggct gacggtggtg gggtgggcgg gcaacagtta tcgccgcagc     180

-continued

| | |
|---|---|
| aggcgtggcc acaggtcacc ttcggatgct gcaccagcca gcagcattgg catgctgaaa | 240 |
| tgaaatgaaa tgcatccatg atcaggatca ggaaaaagct gtgaggtgat gccaacatgc | 300 |
| taacagcaga tgagcatgac tgatggccta actgcctgca aggccgtcgg gtacactcta | 360 |
| ctgatgagaa tatcttaaca gcatctttgg tggcatgtct aagtcctatg ataccaaga | 420 |
| aatgaatcag tcgatctaaa gcgaaaagaa tattttgcag gacttacaga gtgaggctgt | 480 |
| cgccattgtg atgaagagtg caagaagcat gagccatgcg acaagggcga gggcagtgtt | 540 |
| cttcatgcgg ctcatgcctc cctttgtgtt gaatcttcag atgtcttctt gtgagcagct | 600 |
| gagatggtaa tgttgctatg tgctgtgtgt gtgtgtgtgt gtctatatat agaggtgacc | 660 |
| gcctattcaa attgtgataa gatgcagccg ttttgctgga ctactgtagt tattggactg | 720 |
| ttgacgccat ctagatctct ctgtgttgac tcttgagatg gtggttttga taatttgttt | 780 |
| cctagctgac gtttcttcga atacaacttc cattgtgatg tggccaggtg gattaaccag | 840 |
| ttacaaaatt tactacacac cgaatttcct gcag | 874 |

<210> SEQ ID NO 58
<211> LENGTH: 23
<212> TYPE: DNA
<213> ORGANISM: Artificial Sequence
<220> FEATURE:
<223> OTHER INFORMATION: primer

<400> SEQUENCE: 58
gcatgtgtca gatgatctgg tga    23

<210> SEQ ID NO 59
<211> LENGTH: 26
<212> TYPE: DNA
<213> ORGANISM: Artificial Sequence
<220> FEATURE:
<223> OTHER INFORMATION: primer

<400> SEQUENCE: 59
gctgttagct tcttctaatc gtcggt    26

<210> SEQ ID NO 60
<211> LENGTH: 23
<212> TYPE: DNA
<213> ORGANISM: Artificial Sequence
<220> FEATURE:
<223> OTHER INFORMATION: primer

<400> SEQUENCE: 60
tcgagggatc aaactttcaa tcg    23

<210> SEQ ID NO 61
<211> LENGTH: 22
<212> TYPE: DNA
<213> ORGANISM: Artificial Sequence
<220> FEATURE:
<223> OTHER INFORMATION: primer

<400> SEQUENCE: 61
cgtctgctcc gtgactctcc at    22

<210> SEQ ID NO 62
<211> LENGTH: 285
<212> TYPE: DNA
<213> ORGANISM: Sorghum bicolor
<220> FEATURE:
<221> NAME/KEY: misc_feature

```
<222> LOCATION: 12, 18, 19, 20, 23, 29, 30, 131, 160, 179, 186, 197,
      226, 263, 268, 271, 273, 276, 281, 282
<223> OTHER INFORMATION: n = A,T,C or G

<400> SEQUENCE: 62
cccctctccc cnttttttnnn tcnctcaann cggccgaccc cgaattcgtc gacctcgagg      60
gatcaaactt tcaatcggtt ccagacgggg agagacagag aaggggggg gggagagaga      120 gagggtccat ngagagatgg agagtcacgg agcagacggn gtgggaggga aagacgang      180 gtagangacg actcgtncag gagagagagg gagatacagt tacagngcat ggagacatag      240
agagcagaga gagagacggc gangtcgnag ncncantcat nnctc                     285

<210> SEQ ID NO 63
<211> LENGTH: 22
<212> TYPE: DNA
<213> ORGANISM: Artificial Sequence
<220> FEATURE:
<223> OTHER INFORMATION: primer

<400> SEQUENCE: 63
tggggaaaaa gaaagccatc ag                                              22

<210> SEQ ID NO 64
<211> LENGTH: 22
<212> TYPE: DNA
<213> ORGANISM: Artificial Sequence
<220> FEATURE:
<223> OTHER INFORMATION: primer

<400> SEQUENCE: 64
cgcttcagtt aggtgtggct ca                                              22

<210> SEQ ID NO 65
<211> LENGTH: 776
<212> TYPE: DNA
<213> ORGANISM: Sorghum bicolor

<400> SEQUENCE: 65
ctgcaggtgt ggcggcatgc agcactggtg cgagacagcg ggacgactgc catgacgacg      60
ctctgcattg catgtactac agtagtacta accagccatg gggaaaaaga aagccatcag     120
agtaaagggc aaggcaacaa gagacccgga cggagagtgc aatgccatga ggatgcggat     180
gcggatgcgg atgcggcctt ggaaacgtac tacgggagga gtaaatgccg tcccggctct     240
cgctcgcgct tgcagatttt gtagggcgcc attgacatct tccttccctg ctttctcggc     300
actgccctgc tagctgcttc atgcgtgcat gagccacacc taactgaagc gctgtagtaa     360
aaaagaaaca gccagggcgc tcgatctcat gcaagccatg acctcctcat gatggttgat     420
ggaaaggttc agctctttcg accggccgtt gcatgcatga gtgctccagt tgaggcagca     480
tgtgaatgat aaaatactgc tgaatcagta agccctatac acacatacat atatatccta     540
gagactttgg ggaactactt cataaaacca ctcaaaaaat tcagtgcatg caggtgcatg     600
gagaaggaac acatgcatgc atggttgaat tgaacgctgg ttgtttactg aagaaagctt     660
caatgagaca cggtcaatgc aaaggagaga gagacagatc gagagggaaa gagattagag     720
acagaaaaaa caatgtagta ggagcatact cagagtgatg gaattgaatg ctgcag         776

<210> SEQ ID NO 66
<211> LENGTH: 17
<212> TYPE: DNA
<213> ORGANISM: Artificial Sequence
```

```
<220> FEATURE:
<223> OTHER INFORMATION: primer

<400> SEQUENCE: 66
agcagcagca gcaacag                                                17

<210> SEQ ID NO 67
<211> LENGTH: 18
<212> TYPE: DNA
<213> ORGANISM: Artificial Sequence
<220> FEATURE:
<223> OTHER INFORMATION: primer

<400> SEQUENCE: 67
gcgtggtctt tgtggttc                                               18

<210> SEQ ID NO 68
<211> LENGTH: 22
<212> TYPE: DNA
<213> ORGANISM: Artificial Sequence
<220> FEATURE:
<223> OTHER INFORMATION: primer

<400> SEQUENCE: 68
acggacggga acagagaaag aa                                          22

<210> SEQ ID NO 69
<211> LENGTH: 22
<212> TYPE: DNA
<213> ORGANISM: Artificial Sequence
<220> FEATURE:
<223> OTHER INFORMATION: primer

<400> SEQUENCE: 69
acgaggacga gtgcatgatg ag                                          22

<210> SEQ ID NO 70
<211> LENGTH: 811
<212> TYPE: DNA
<213> ORGANISM: Sorghum bicolor

<400> SEQUENCE: 70
ctgcagtgtg taagtggatt ttatttcctt ttatattaat taatagaaag ccaggaaaga    60
agtttacgat cggttcatgg attcgctgtg atcagcacac atgattgatg aacaggtgca   120
agaaattgac gggatctttt gagaagagca agagctcgat ccggtcgtgc gggaacgaac   180
tggcagagat agatcgatac gtactgcacg acgttgtaac tgtgacgaat ccaatgcagc   240
atgcatgcac attgaatttc atgcatgcgt ttgtaagttt ggtgaataaa tactgaaacg   300
aagttcatgc atgcgttctg aagtttggtg catgatactg aaactttgcg ttctgaagtt   360
tggtggataa tacttgaact tttctgaatg cgtacataca tgcatagaat gaaacaacaa   420
acaagaaatc ctcgagatga acaacaagc aagaaatcct cgagctagga tggatagatc   480
gatcgatgga tcactactgt gacatgggac aaaaaaagaa aaatcgaaac tgttattatt   540
gacacgcagg taacgcgcca tgcacagtgt tcacacgcca cggacgggaa cagagaaaga   600
acacgacgag cacggagcaa cgcatgtcgt atatatatat atatatagcc taggatatag   660
ataggagagg gatgatgatg gatcagttgt ggtgctgctg ggtgtagatg tagtcggtgt   720
gcgcgttcag cgtgcgcctc atcatgcact cgtcctcgtc gttggcgccc tcgcacccgc   780
cttccgtttc cgccgatccc tgcttctgca g                                 811
```

```
<210> SEQ ID NO 71
<211> LENGTH: 22
<212> TYPE: DNA
<213> ORGANISM: Artificial Sequence
<220> FEATURE:
<223> OTHER INFORMATION: primer

<400> SEQUENCE: 71
tccaaacagc ctcttggtac gc                                              22

<210> SEQ ID NO 72
<211> LENGTH: 22
<212> TYPE: DNA
<213> ORGANISM: Artificial Sequence
<220> FEATURE:
<223> OTHER INFORMATION: primer

<400> SEQUENCE: 72
aacaagggaa ttttgtcgtc cg                                              22

<210> SEQ ID NO 73
<211> LENGTH: 563
<212> TYPE: DNA
<213> ORGANISM: Sorghum bicolor
<220> FEATURE:
<221> NAME/KEY: misc_feature
<222> LOCATION: 12, 540
<223> OTHER INFORMATION: n = A,T,C or G

<400> SEQUENCE: 73
cgtcgactcg anggatcttg gcgtcaatta atccaaacag cctcttggta cgcatcaatt      60
attggttaga tatattttaa gctgcccata tgtttcttca tcaggtcaca acacacacac     120
acacacacac aaaaaaaaaa acttggcctg caatcagcat caccatgaac gggaatagga     180
actcttgctg ccaagtggat ggtctgtctt tgcggacgac aaaattccct tgttcttaga     240
atatgtagta ataatatatt aagagtatgt ttagatccct ataaagaata ttataatttt     300
ttcaggatcc gggccctcta gatcggcgca tgcataagct tgagtatcta tatgtcccta     360
aatactggct atcaggtcaa gcgttctgtg tgaatgtatc gctccatcac cacatacagc     420
cgaactaatt aaccgggtct atatgacacc ctatgctgcc ccgccgctca tcggaacgtc     480
tcacgctata tcgcacccgg aagcgtggtt ggccctcctc cccatacccg cccgctcgcn     540
cgcacgacac cccaaggtac gtc                                             563

<210> SEQ ID NO 74
<211> LENGTH: 21
<212> TYPE: DNA
<213> ORGANISM: Artificial Sequence
<220> FEATURE:
<223> OTHER INFORMATION: primer

<400> SEQUENCE: 74
cgacgaacga acgagcaaaa g                                               21

<210> SEQ ID NO 75
<211> LENGTH: 22
<212> TYPE: DNA
<213> ORGANISM: Artificial Sequence
<220> FEATURE:
<223> OTHER INFORMATION: primer

<400> SEQUENCE: 75
cgtgtggacg acgaattgag tt                                              22
```

```
<210> SEQ ID NO 76
<211> LENGTH: 455
<212> TYPE: DNA
<213> ORGANISM: Sorghum bicolor

<400> SEQUENCE: 76
gcacgaggat catctctagc tcgtcttgtt cgtcctcctt ggaaggaagc agcaatttgt      60
tgctcacctc cacacggcct gcttattatt tttagcaaaa agcaggcaca ggcaggagaa     120
gagaggagag ggggcgacga gggcaacgca tcaaatcgat agatcaatca ctgctgctcc     180
tgctcgtcgt ggtcagccgc cagcgacgaa cgaacgagca aaaggccggc tgatttgctc     240
tctctctctc tctctctctc tctctctctc tgctctgcta gtggcgccga atcaatcaat     300
caatttcaat cacaaagtta agttggaatt ttgattgctc catatataaa ctcaattcgt     360
cgtccacacg acattaattg gatcggaatc ggaatcggac cacccaccat cagaaagcaa     420
agcagaggaa ggcagtccat tcaagattgg aaggc                                455
```